US011760987B2

(12) United States Patent
Hammond et al.

(10) Patent No.: US 11,760,987 B2
(45) Date of Patent: Sep. 19, 2023

(54) COMPOSITIONS AND METHODS FOR THE TREATMENT OR PREVENTION OF HEART FAILURE

(71) Applicants: The Regents of the University of California, Oakland, CA (US); The United States of America as Represented by The Department of Veterans Affairs, Washington, DC (US)

(72) Inventors: H. Kirk Hammond, La Jolla, CA (US); Mei Hua Gao, San Diego, CA (US); Ngai Chin Lai, La Jolla, CA (US)

(73) Assignees: THE REGENTS OF THE UNIVERSITY OF CALIFORNIA, Oakland, CA (US); THE UNITED STATES OF AMERICA AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 1322 days.

(21) Appl. No.: 16/124,482

(22) Filed: Sep. 7, 2018

(65) Prior Publication Data
US 2019/0264189 A1 Aug. 29, 2019

Related U.S. Application Data

(60) Provisional application No. 62/555,471, filed on Sep. 7, 2017.

(51) Int. Cl.
*C12N 9/88* (2006.01)
*A61P 9/04* (2006.01)
*A61K 48/00* (2006.01)
*A01K 67/027* (2006.01)
*C12N 15/86* (2006.01)
*C12N 5/10* (2006.01)
*C12N 15/85* (2006.01)

(52) U.S. Cl.
CPC ............ *C12N 9/88* (2013.01); *A01K 67/0275* (2013.01); *A61K 48/00* (2013.01); *A61P 9/04* (2018.01); *C12N 5/10* (2013.01); *C12N 15/85* (2013.01); *C12N 15/86* (2013.01); *C12Y 406/01001* (2013.01); *A01K 2227/105* (2013.01); *C07K 2319/00* (2013.01)

(58) Field of Classification Search
CPC . C12N 9/88; C12N 5/10; C12N 15/85; C12N 15/86; C07K 2319/00; C12Y 406/01001; A61K 48/00; A61K 9/04
USPC ..................... 435/232, 320.1, 325
See application file for complete search history.

(56) References Cited

FOREIGN PATENT DOCUMENTS

| WO | 2013123094 A2 | 8/2013 |
|----|---------------|--------|
| WO | 2014197624 A1 | 12/2014 |
| WO | 2015150914 A2 | 10/2015 |

OTHER PUBLICATIONS

Scholich et al. (1997) PNAS, vol. 942, 915-2920 Tang et al. (1995) Science, vol. 268 (5218), 1769-1772.*
Tang et al. (1995) Science, vol. 268 (5218), 1769-1772.*
Yu et al. (2015) Biotech. Adv., vol. 33, 155-164.*
Chen et al. (2013) Adv. Drug Deliv. Rev., vol. 65(1), 1357-1369. doi:10.1016/j.addr. 2012.09.039.,pp. 1-32.*
Lin et al. (2002) J. Biol. Chem., vol. 277(18), 15721-15728.*
Rincon et al. (2015) Cardiovascular Research, vol. 108, 4-20, doi:10.1093/cvr/cvv205, pp. 1-17.*
Matkar et al. (2016) Gene Therapy, vol. 23, 635-648, doi:10.1038/gt.2016.43.*
Lai et al. (2004) Circulation, vol. 110, 330-336.*
Roth et al. (2004) Am. J. Physiol. Heart Circ. Physiol., vol. 287, H172-H177, pp. 1-6.*
Hammond et al. (2016) JAMA Cardiol., vol. 1(2), 163-171, doi:10.1001/jamacardio.2016.0008., pp. 1-19.*
Gao et al., "Preserved Cardiac Function despite Marked Impairment of cAMP Generation" PLOS One, Sep. 2013, vol. 8, No. 9, p. 1-8.
Hammond et al., "Intracoronary Gene Transfer of Adenylyl Cyclase 6 in Patients With Heart Failure a Randomized Clinical Trial" JAMA Cardiology, May 2016, vol. 1, No. 2, p. 163-171.
Thangavel et al., "The C1 and C2 domains target human type 6 adenylyl cyclase to lipid rafts and caveolae" Cell Signal, Feb. 2009, vol. 21, No. 2, p. 301-308.
Sunahara et al., "Interaction of Gsa with the Cytosolic Domains of Mammalian Adenylyl Cyclase" The Journal of Biological Chemistry, Aug. 1997, vol. 272, No. 35, p. 22265-22271.
Liu et al., "Catalytic mechanism of the adenylyl and guanylyl cyclases: Modeling and mutational analysis" Proc. Natl. Acad. Sci. Dec. 1997, vol. 94, p. 13414-13419.
Tang et al., "Catalytic Mechanism and Regulation of Mammalian Adenylyl Cyclases" Molecular Pharmacology, 1998, vol. 54, p. 231-240.

* cited by examiner

*Primary Examiner* — Anne Marie S Wehbe
(74) *Attorney, Agent, or Firm* — Greer, Burns & Crain, LTD.; Gregory P. Einhorn

(57) ABSTRACT

In alternative embodiments, provided are compositions, including products of manufacture and kits, and methods, for treating a heart failure in a subject in need thereof comprising administering to the subject an isolated or recombinant nucleic acid, an isolated or recombinant or chimeric polypeptide, or an engineered cell, as provided herein, thereby treating the subject. In alternative embodiments, the administration reduces left ventricular (LV) hypertrophy, increases LV peak pressure development, reduced cAMP production and/or improves LV peak pressure decay in a pressure-overload in the subject. In alternative embodiments, provided are compositions and methods for: treating, ameliorating, or slowing the progress of, or protecting (preventing) an individual or a patient against heart failure; or, reducing LV hypertrophy, increasing LV peak pressure development, and/or improving LV peak pressure decay in a pressure-overload in an individual in need thereof.

11 Claims, 25 Drawing Sheets

Specification includes a Sequence Listing.

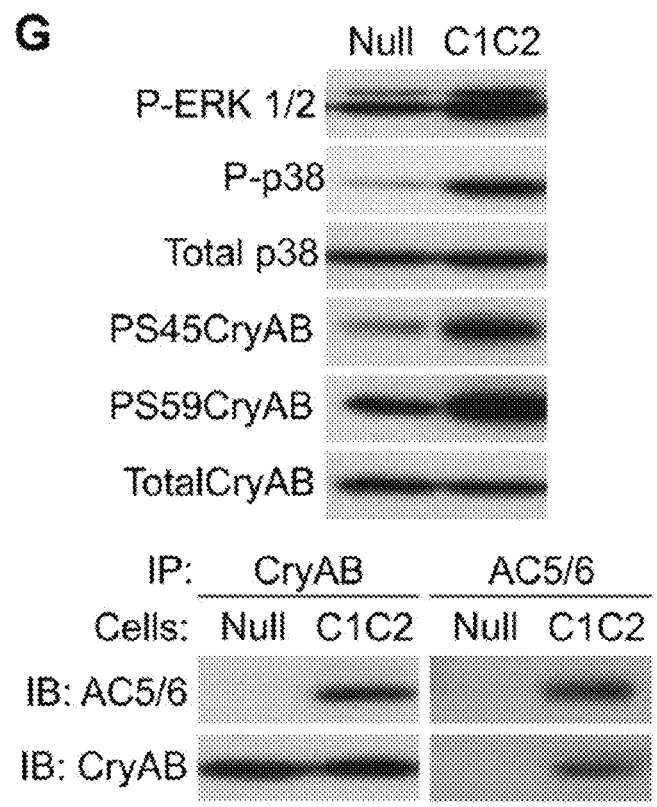
FIG. 1G
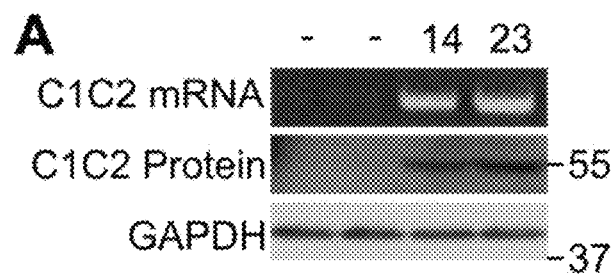
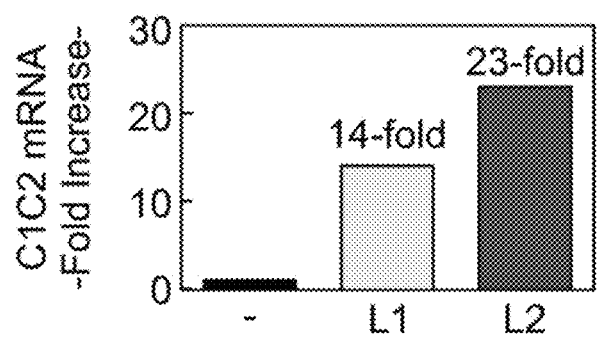
FIG. 2A

SEQ ID NO: 1
MEMKEDINTKKED MMFHKIYIQK HDNVSILFAD IEGFTSLASQ
CTAQELVMTL NELFARFDKL AAENHCLRIK ILGDCYYCVS GLPEARADHA
HCCVEMGVDM IEAISLVREV TGVNVNMRVG IHSGRVHCGV LGLRKWQFDV
WSNDVTLANH MEAGGRAGRI HITRATLQYL NGDYEVEPGR GGERNAYLKE
QCIETFLILG ASQKRKEEKA MLAKLQRT

SEQ ID NO: 2
IPPAAAMYNR RLLHNILPKD VAAHFLARER RNDELYYQSC ECVAVMFASI ANFSEFYVEL
EANNEGVECL RLLNEIIADF DEIISEERFR QLEKIKTIGS TYMAASGLNA
STYDQVGRSH ITALADYAMR LMEQMKHINE HSFNNFQMKI GLNMGPVVAG
VIGARKPQYD IWGNTVNVSS RMDSTGVPDR IQVTTDLYQV LAAKGYQLEC
RGVVKVKGKG EMTTY

SEQ ID NO: 3 Linker- RANSMEGAAAGG

SEQ ID NO:6 (encoding SEQ ID NO:1)

GAGATGAAAGAAGACATCAACACAAAAAAAGA GGACATGATGTTCCATAAGATCTAC
ATCCAGAAGCATGATAATGTCAGCATCCTGTTTGCGGACATTGAGGGCTTCACCAGCC
TGGCCTCCCAGTGCACTGCACAGGAACTGGTCATGACCTTGAATGAGCTCTTTGCCCG
GTTTGACAAGCTGGCTGCGGAGAATCACTGTCTGAGGATCAAGATCTTAGGAGACTGT
TACTACTGCGTGTCAGGGCTGCCCGAGGCCCGGGCAGATCACGCCCACTGCTGTGTG
GAGATGGGGGTAGACATGATCGAAGCCATCTCGCTGGTGCGTGAGGTAACAGGTGTG
AACGTGAACATGCGTGTGGGCATCCACAGCGGACGTGTGCATTGCGGCGTCCTTGGC
CTACGGAAATGGCAGTTTGATGTCTGGTCAAACGATGTGACCCTGGCTAACCACATGG
AGGCCGGGGCCGGGCCGGCCGCATCCACATCACTCGGGCTACACTGCAGTACTTG
AACGGGGACTATGAGGTGGAGCCAGGCCGTGGTGGTGAACGCAATGCGTACCTCAAG
GAGCAGTGCATTGAGACCTTCCTCATACTTGGCGCCAGCCAAAAACGGAAAGAGGAG
AAAGCCATGCTGGCCAAGCTTCAGCGGACACGGGCCAACTCCATGGAAGGA

SEQ ID NO:7 (encoding SEQ ID NO:2)

TACAACCGGAGGTTGCTGCATAACATTCTTCCCAAGGACGTGGCCGCCCACTTCCTGG
CCCGGGAACGCCGCAACGATGAGCTGTACTACCAGTCGTGTGAATGTGTGGCTGTCA
TGTTTGCCTCCATCGCCAATTTCTCGGAGTTCTACGTGGAGCTCGAGGCAAACAACGA
GGGCGTGGAGTGCCTGCGGCTGCTCAATGAGATCATCGCAGACTTTGACGAGATCAT
CAGTGAGGAGAGATTCCGGCAGTTGGAGAAGATCAAGACCATCGGTAGCACCTACAT
GGCCGCCTCTGGGCTAAATGCCAGCACCTATGACCAGGTCGGCCGCTCACACATCAC
GGCGCTGGCTGACTATGCCATGCGGCTCATGGAGCAGATGAAACACATCAATGAACA
CTCTTTCAACAATTTCCAGATGAAGATCGGGTTGAACATGGGTCCGGTTGTAGCAGGC
GTCATTGGGGCCCGAAAGCCACAGTATGACATCTGGGGAAATACCGTGAATGTTTCCA
GTCGTATGGACAGCACTGGAGTTCCTGACCGAATACAGGTGACTACGGACCTATACCA
GGTTCTAGCTGCCAAGGGCTACCAGCTGGAGTGTCGAGGGGTGGTCAAGGTGAAGG
GAAAGGGGGAGATGACCACCTAC

FIG. 6A

C1-linker-C2 DNA sequence (SEQ ID NO: 4)

BOLD: 5' untranslated region
Italics: C1 start
UNDERLINE: Linker between C1 and C2 domains
BOLD/ITALICS: AU1 tag

GTCTCTCCTCCCAGCACGTTGCC
*ATG*
GAGATGAAAGAAGACATCAACACAAAAAAAGA GGACATGATGTTCCATAAGATCTAC
ATCCAGAAGCATGATAATGTCAGCATCCTGTTTGCGGACATTGAGGGCTTCACCAGCCTGG
CCTCCCAGTGCACTGCACAGGAACTGGTCATGACCTTGAATGAGCTCTTTGCCCGGTTTGA
CAAGCTGGCTGCGGAGAATCACTGTCTGAGGATCAAGATCTTAGGAGACTGTTACTACTGC
GTGTCAGGGCTGCCCGAGGCCCGGGCAGATCACGCCCACTGCTGTGTGGAGATGGGGGTAG
ACATGATCGAAGCCATCTCGCTGGTGCGTGAGGTAACAGGTGTGAACGTGAACATGCGTGT
GGGCATCCACAGCGGACGTGTGCATTGCGGCGTCCTTGGCCTACGGAAATGGCAGTTTGAT
GTCTGGTCAAACGATGTGACCCTGGCTAACCACATGGAGGCCGGGGGCCGGGCCGGCCGCA
TCCACATCACTCGGGCTACACTGCAGTACTTGAACGGGGACTATGAGGTGGAGCCAGGCCG
TGGTGGTGAACGCAATGCGTACCTCAAGGAGCAGTGCATTGAGACCTTCCTCATACTTGGC
GCCAGCCAAAAACGGAAAGAGGAGAAAGCCATGCTGGCCAAGCTTCAGCGGACACGGGCCA
ACTCCATGGAAGGA
GCTGCAGCGGGTGGAATTCCTCCTGCGGCGGCAATG
TACAACCGGAGGTTGCTGCATAACATTCTTCCCAAGGACGTGGCCGCCCACTTCCTGGCC
CGGGAACGCCGCAACGATGAGCTGTACTACCAGTCGTGTGAATGTGTGGCTGTCATGTTTG
CCTCCATCGCCAATTTCTCGGAGTTCTACGTGGAGCTCGAGGCAAACAACGAGGGCGTGGA
GTGCCTGCGGCTGCTCAATGAGATCATCGCAGACTTTGACGAGATCATCAGTGAGGAGAGA
TTCCGGCAGTTGGAGAAGATCAAGACCATCGGTAGCACCTACATGGCCGCCTCTGGGCTAA
ATGCCAGCACCTATGACCAGGTCGGCCGCTCACACATCACGGGCTGGCTGACTATGCCAT
GCGGCTCATGGAGCAGATGAAACACATCAATGAACACTCTTTCAACAATTCCAGATGAAG
ATCGGGTTGAACATGGGTCCGGTTGTAGCAGGCGTCATTGGGGCCCGAAAGCCACAGTATG
ACATCTGGGGAAATACCGTGAATGTTTCCAGTCGTATGGACAGCACTGGAGTTCCTGACCG
AATACAGGTGACTACGGACCTATACCAGGTTCTAGCTGCCAAGGGCTACCAGCTGGAGTGT
CGAGGGGTGGTCAAGGTGAAGGGAAAGGGGGAGATGACCACCTAC
*GACACTTACCGGTACATT*

C1-linker-C2 Amino Acid Sequence (SEQ ID NO:5)

```
  1 LSSQHVAMEM EDINTKKED RMFHKIYIQK HDNVSILFAD IEGFTSLASQ
 51 CTAQELVMTL NELFARFDKL AAENHCLRIK ILGDCYYCVS GLPEARADHA
101 HCCVEMGVDM IEAISLVREV TGVNVNMRVG IHSGRVHCGV LGLRKWQFDV
151 WSNDVTLANH MEAGGKAGRI HITRATLQYL NGDYEVEPGR GGERNAYLKE
201 QCIETFLILS ASQKRKEEKA MLAKLQRTRA NSMEGAAASG IPPAAAMYRR
251 RLLHNILPKD VAAHFLAPER RNDELYYQSC ECVAVMFASI ANFSEFYVEL
301 EANNEGVECL RLLNEIIADF DEIISEERFR QLEKIKTIGS TYMAASGLNA
351 STYDQVGRSH ITALADYAMR LMEQMKHINE HSFNNFQMKI GLNMGPVVAG
401 VIGARKPQYD IWGNTVNVSS RMDSTGVPDR IQVTTDLYQV LAAKGYQLEC
451 RGVVKVKGKG EMTTYDTYRY I
```

FIG. 6B

SEQUENCE LISTING

```
<160> NUMBER OF SEQ ID NOS: 15

<210> SEQ ID NO 1
<211> LENGTH: 221
<212> TYPE: PRT
<213> ORGANISM: artificial sequence
<220> FEATURE:
<223> OTHER INFORMATION: synthetic peptide

<400> SEQUENCE: 1

Met Glu Met Lys Glu Asp Ile Asn Thr Lys Lys Glu Asp Met Met Phe
1               5                   10                  15

His Lys Ile Tyr Ile Gln Lys His Asp Asn Val Ser Ile Leu Phe Ala
            20                  25                  30

Asp Ile Glu Gly Phe Thr Ser Leu Ala Ser Gln Cys Thr Ala Gln Glu
        35                  40                  45

Leu Val Met Thr Leu Asn Glu Leu Phe Ala Arg Phe Asp Lys Leu Ala
    50                  55                  60

Ala Glu Asn His Cys Leu Arg Ile Lys Ile Leu Gly Asp Cys Tyr Tyr
65                  70                  75                  80

Cys Val Ser Gly Leu Pro Glu Ala Arg Ala Asp His Ala His Cys Cys
                85                  90                  95

Val Glu Met Gly Val Asp Met Ile Glu Ala Ile Ser Leu Val Arg Glu
            100                 105                 110

Val Thr Gly Val Asn Val Asn Met Arg Val Gly Ile His Ser Gly Arg
        115                 120                 125

Val His Cys Gly Val Leu Gly Leu Arg Lys Trp Gln Phe Asp Val Trp
    130                 135                 140

Ser Asn Asp Val Thr Leu Ala Asn His Met Glu Ala Gly Gly Arg Ala
```

```
                145                 150                 155                 160
Gly Arg Ile His Ile Thr Arg Ala Thr Leu Gln Tyr Leu Asn Gly Asp
                    165                 170                 175

Tyr Glu Val Glu Pro Gly Arg Gly Glu Arg Asn Ala Tyr Leu Lys
                180                 185                 190

Glu Gln Cys Ile Glu Thr Phe Leu Ile Leu Gly Ala Ser Gln Lys Arg
            195                 200                 205

Lys Glu Glu Lys Ala Met Leu Ala Lys Leu Gln Arg Thr
    210                 215                 220

<210> SEQ ID NO 2
<211> LENGTH: 225
<212> TYPE: PRT
<213> ORGANISM: artificial sequence
<220> FEATURE:
<223> OTHER INFORMATION: synthetic peptide

<400> SEQUENCE: 2

Ile Pro Pro Ala Ala Met Tyr Asn Arg Arg Leu Leu His Asn Ile
1               5                   10                  15

Leu Pro Lys Asp Val Ala Ala His Phe Leu Ala Arg Glu Arg Arg Asn
            20                  25                  30

Asp Glu Leu Tyr Tyr Gln Ser Cys Glu Cys Val Ala Val Met Phe Ala
        35                  40                  45

Ser Ile Ala Asn Phe Ser Glu Phe Tyr Val Glu Leu Glu Ala Asn Asn
    50                  55                  60

Glu Gly Val Glu Cys Leu Arg Leu Leu Asn Glu Ile Ile Ala Asp Phe
65                  70                  75                  80

Asp Glu Ile Ile Ser Glu Glu Arg Phe Arg Gln Leu Glu Lys Ile Lys
                85                  90                  95

Thr Ile Gly Ser Thr Tyr Met Ala Ala Ser Gly Leu Asn Ala Ser Thr
            100                 105                 110

Tyr Asp Gln Val Gly Arg Ser His Ile Thr Ala Leu Ala Asp Tyr Ala
        115                 120                 125

Met Arg Leu Met Glu Gln Met Lys His Ile Asn Glu His Ser Phe Asn
    130                 135                 140

Asn Phe Gln Met Lys Ile Gly Leu Asn Met Gly Pro Val Val Ala Gly
145                 150                 155                 160

Val Ile Gly Ala Arg Lys Pro Gln Tyr Asp Ile Trp Gly Asn Thr Val
                165                 170                 175

Asn Val Ser Ser Arg Met Asp Ser Thr Gly Val Pro Asp Arg Ile Gln
            180                 185                 190

Val Thr Thr Asp Leu Tyr Gln Val Leu Ala Ala Lys Gly Tyr Gln Leu
        195                 200                 205

Glu Cys Arg Gly Val Val Lys Val Lys Gly Lys Gly Glu Met Thr Thr
    210                 215                 220

Tyr
225

<210> SEQ ID NO 3
<211> LENGTH: 12
<212> TYPE: PRT
<213> ORGANISM: artificial sequence
<220> FEATURE:
<223> OTHER INFORMATION: synthetic peptide

<400> SEQUENCE: 3
```

Arg Ala Asn Ser Met Glu Gly Ala Ala Ala Gly Gly
1               5                   10

<210> SEQ ID NO 4
<211> LENGTH: 1415
<212> TYPE: DNA
<213> ORGANISM: artificial sequence
<220> FEATURE:
<223> OTHER INFORMATION: synthetic polynucleotide

<400> SEQUENCE: 4

```
gtctctcctc ccagcacgtt gccatggaga tgaaagaaga catcaacaca aaaaaagagg      60
acatgatgtt ccataagatc tacatccaga agcatgataa tgtcagcatc ctgtttgcgg     120
acattgaggg cttcaccagc ctggcctccc agtgcactgc acaggaactg gtcatgacct     180
tgaatgagct ctttgcccgg tttgacaagc tggctgcgga gaatcactgt ctgaggatca     240
agatcttagg agactgttac tactgcgtgt cagggctgcc cgaggcccgg gcagatcacg     300
cccactgctg tgtggagatg gggtagaca tgatcgaagc catctcgctg gtgcgtgagg      360
taacaggtgt gaacgtgaac atgcgtgtgg gcatccacag cggacgtgtg cattgcggcg     420
tccttggcct acggaaatgg cagtttgatg tctggtcaaa cgatgtgacc ctggctaacc     480
acatggaggc cggggggccgg gccggccgca tccacatcac tcgggctaca ctgcagtact    540
tgaacgggga ctatgaggtg gagccaggcc gtggtggtga acgcaatgcg tacctcaagg     600
agcagtgcat tgagaccttc ctcatacttg gcgccagcca aaaacggaaa gaggagaaag     660
ccatgctggc caagcttcag cggacacggg ccaactccat ggaaggagct gcagcgggtg     720
gaattcctcc tgcggcggca atgtacaacc ggaggttgct gcataacatt cttcccaagg     780
acgtggccgc ccacttcctg gcccgggaac gccgcaacga tgagctgtac taccagtcgt     840
gtgaatgtgt ggctgtcatg tttgcctcca tcgccaattt ctcggagttc tacgtggagc     900
tcgaggcaaa caacgagggc gtggagtgcc tgcggctgct caatgagatc atcgcagact     960
tgacgagat catcagtgag gagagattcc ggcagttgga agagatcaag accatcggta    1020
gcacctacat ggccgcctct gggctaaatg ccagcaccta tgaccaggtc ggccgctcac    1080
acatcacggc gctggctgac tatgccatgc ggctcatgga gcagatgaaa cacatcaatg    1140
aacactcttt caacaatttc cagatgaaga tcgggttgaa catgggtccg gttgtagcag    1200
gcgtcattgg ggcccgaaag ccacagtatg acatctgggg aaataccgtg aatgttccca    1260
gtcgtatgga cagcactgga gttcctgacc gaatacaggt gactacggac ctataccagg    1320
ttctagctgc caagggctac cagctggagt gtcgagggg ggtcaaggtg aagggaaagg    1380
gggagatgac cacctacgac acttaccggt acatt                               1415
```

<210> SEQ ID NO 5
<211> LENGTH: 471
<212> TYPE: PRT
<213> ORGANISM: artificial sequence
<220> FEATURE:
<223> OTHER INFORMATION: synthetic polypeptide

<400> SEQUENCE: 5

Leu Ser Ser Gln His Val Ala Met Glu Met Lys Glu Asp Ile Asn Thr
1               5                   10                  15

Lys Lys Glu Asp Met Met Phe His Lys Ile Tyr Ile Gln Lys His Asp
                20                  25                  30

Asn Val Ser Ile Leu Phe Ala Asp Ile Glu Gly Phe Thr Ser Leu Ala
            35                  40                  45

```
Ser Gln Cys Thr Ala Gln Glu Leu Val Met Thr Leu Asn Glu Leu Phe
    50                  55                  60
Ala Arg Phe Asp Lys Leu Ala Ala Glu Asn His Cys Leu Arg Ile Lys
65                  70                  75                  80
Ile Leu Gly Asp Cys Tyr Tyr Cys Val Ser Gly Leu Pro Glu Ala Arg
                85                  90                  95
Ala Asp His Ala His Cys Cys Val Glu Met Gly Val Asp Met Ile Glu
            100                 105                 110
Ala Ile Ser Leu Val Arg Glu Val Thr Gly Val Asn Val Asn Met Arg
        115                 120                 125
Val Gly Ile His Ser Gly Arg Val His Cys Gly Val Leu Gly Leu Arg
    130                 135                 140
Lys Trp Gln Phe Asp Val Trp Ser Asn Asp Val Thr Leu Ala Asn His
145                 150                 155                 160
Met Glu Ala Gly Gly Arg Ala Gly Arg Ile His Ile Thr Arg Ala Thr
                165                 170                 175
Leu Gln Tyr Leu Asn Gly Asp Tyr Glu Val Glu Pro Gly Arg Gly Gly
            180                 185                 190
Glu Arg Asn Ala Tyr Leu Lys Glu Gln Cys Ile Glu Thr Phe Leu Ile
        195                 200                 205
Leu Gly Ala Ser Gln Lys Arg Lys Glu Lys Ala Met Leu Ala Lys
    210                 215                 220
Leu Gln Arg Thr Arg Ala Asn Ser Met Glu Gly Ala Ala Ala Gly Gly
225                 230                 235                 240
Ile Pro Pro Ala Ala Ala Met Tyr Asn Arg Arg Leu Leu His Asn Ile
                245                 250                 255
Leu Pro Lys Asp Val Ala Ala His Phe Leu Ala Arg Glu Arg Arg Asn
            260                 265                 270
Asp Glu Leu Tyr Tyr Gln Ser Cys Glu Cys Val Ala Val Met Phe Ala
        275                 280                 285
Ser Ile Ala Asn Phe Ser Glu Phe Tyr Val Glu Leu Glu Ala Asn Asn
    290                 295                 300
Glu Gly Val Glu Cys Leu Arg Leu Leu Asn Glu Ile Ile Ala Asp Phe
305                 310                 315                 320
Asp Glu Ile Ile Ser Glu Glu Arg Phe Arg Gln Leu Glu Lys Ile Lys
                325                 330                 335
Thr Ile Gly Ser Thr Tyr Met Ala Ala Ser Gly Leu Asn Ala Ser Thr
            340                 345                 350
Tyr Asp Gln Val Gly Arg Ser His Ile Thr Ala Leu Ala Asp Tyr Ala
        355                 360                 365
Met Arg Leu Met Glu Gln Met Lys His Ile Asn Glu His Ser Phe Asn
    370                 375                 380
Asn Phe Gln Met Lys Ile Gly Leu Asn Met Gly Pro Val Val Ala Gly
385                 390                 395                 400
Val Ile Gly Ala Arg Lys Pro Gln Tyr Asp Ile Trp Gly Asn Thr Val
                405                 410                 415
Asn Val Ser Ser Arg Met Asp Ser Thr Gly Val Pro Asp Arg Ile Gln
            420                 425                 430
Val Thr Thr Asp Leu Tyr Gln Val Leu Ala Ala Lys Gly Tyr Gln Leu
        435                 440                 445
Glu Cys Arg Gly Val Val Lys Val Lys Gly Lys Gly Glu Met Thr Thr
    450                 455                 460
```

Tyr Asp Thr Tyr Arg Tyr Ile
465                 470

<210> SEQ ID NO 6
<211> LENGTH: 681
<212> TYPE: DNA
<213> ORGANISM: artificial sequence
<220> FEATURE:
<223> OTHER INFORMATION: synthetic polynucleotide

<400> SEQUENCE: 6

| gagatgaaag aagacatcaa cacaaaaaaa gaggacatga tgttccataa gatctacatc | 60 |
| cagaagcatg ataatgtcag catcctgttt gcggacattg agggcttcac cagcctggcc | 120 |
| tcccagtgca ctgcacagga actggtcatg accttgaatg agctctttgc ccggtttgac | 180 |
| aagctggctg cggagaatca ctgtctgagg atcaagatct taggagactg ttactactgc | 240 |
| gtgtcagggc tgcccgaggc ccgggcagat cacgcccact gctgtgtgga gatgggggta | 300 |
| gacatgatcg aagccatctc gctggtgcgt gaggtaacag gtgtgaacgt gaacatgcgt | 360 |
| gtgggcatcc acagcggacg tgtgcattgc ggcgtccttg cctacggaa atggcagttt | 420 |
| gatgtctggt caaacgatgt gaccctggct aaccacatgg aggccggggg ccgggccggc | 480 |
| cgcatccaca tcactcgggc tacactgcag tacttgaacg gggactatga ggtggagcca | 540 |
| ggccgtggtg gtgaacgcaa tgcgtacctc aaggagcagt gcattgagac cttcctcata | 600 |
| cttggcgcca gccaaaaacg gaaagaggag aaagccatgc tggccaagct tcagcggaca | 660 |
| cgggccaact ccatggaagg a | 681 |

<210> SEQ ID NO 7
<211> LENGTH: 654
<212> TYPE: DNA
<213> ORGANISM: artificial sequence
<220> FEATURE:
<223> OTHER INFORMATION: synthetic polynucleotide

<400> SEQUENCE: 7

| tacaaccgga ggttgctgca taacattctt cccaaggacg tggccgccca cttcctggcc | 60 |
| cgggaacgcc gcaacgatga gctgtactac cagtcgtgtg aatgtgtggc tgtcatgttt | 120 |
| gcctccatcg ccaatttctc ggagttctac gtggagctcg aggcaaacaa cgagggcgtg | 180 |
| gagtgcctgc ggctgctcaa tgagatcatc gcagactttg acgagatcat cagtgaggag | 240 |
| agattccggc agttggagaa gatcaagacc atcggtagca cctacatggc cgcctctggg | 300 |
| ctaaatgcca gcacctatga ccaggtcggc cgctcacaca tcacggcgct ggctgactat | 360 |
| gccatgcggc tcatggagca gatgaaacac atcaatgaac actctttcaa caatttccag | 420 |
| atgaagatcg ggttgaacat gggtccggtt gtagcaggcg tcattgggc ccgaaagcca | 480 |
| cagtatgaca tctggggaaa taccgtgaat gtttccagtc gtatggacag cactggagtt | 540 |
| cctgaccgaa tacaggtgac tacgaccta taccaggttc tagctgccaa gggctaccag | 600 |
| ctggagtgtc gaggggtggt caaggtgaag ggaaagggg agatgaccac ctac | 654 |

<210> SEQ ID NO 8
<211> LENGTH: 12
<212> TYPE: PRT
<213> ORGANISM: artificial sequence
<220> FEATURE:
<223> OTHER INFORMATION: synthetic peptide

<400> SEQUENCE: 8

```
Ala Ala Ala Gly Gly Ile Pro Pro Ala Ala Ala Met
1               5                   10
```

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

```
Asp Thr Tyr Arg Tyr Ile
1               5
```

<210> SEQ ID NO 10
<211> LENGTH: 23
<212> TYPE: DNA
<213> ORGANISM: artificial sequence
<220> FEATURE:
<223> OTHER INFORMATION: synthetic oligonucleotide

<400> SEQUENCE: 10
cacatagaag cctagcccac acc                                              23

<210> SEQ ID NO 11
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 11
gttagccagg gtcacatcgt                                                  20

<210> SEQ ID NO 12
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 12
tgggcctctc tactctgcat                                                  20

<210> SEQ ID NO 13
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 13
tggatgtaac ctcgggtctc                                                  20

<210> SEQ ID NO 14
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 14
atcatgtgca gcagtggtgt                                                  20

<210> SEQ ID NO 15
<211> LENGTH: 20

```
<212> TYPE: DNA
<213> ORGANISM: artificial sequence
<220> FEATURE:
<223> OTHER INFORMATION: synthetic oligonucleotide

<400> SEQUENCE: 15
ccttggagct gactgaggag                                          20
```

COMPOSITIONS AND METHODS FOR THE TREATMENT OR PREVENTION OF HEART FAILURE

RELATED APPLICATIONS

This application claims the benefit of priority to U.S. Provisional Patent Application Ser. No. 62/555,471, filed Sep. 7, 2017. The aforementioned application is expressly incorporated herein by reference in its entirety and for all purposes.

STATEMENT AS TO FEDERALLY SPONSORED RESEARCH

This invention was made with government support under NIH, NHLBI grant no. P01HL066941; and Department of Veteran's Affairs grants: 1I01 BX001515 and 1I01 BX003774. The government has certain rights in the invention.

TECHNICAL FIELD

This invention generally relates to gene therapy and medicine. In alternative embodiments, provided are compositions, including products of manufacture and kits, and methods, for treating a heart failure in a subject in need thereof comprising administering to the subject an isolated or recombinant nucleic acid, an isolated or recombinant or chimeric polypeptide, or an engineered cell, as provided herein, thereby treating the subject. In alternative embodiments, the administration reduces left ventricular (LV) hypertrophy, increases LV peak pressure development, reduced cAMP production and/or improves LV peak pressure decay in a pressure-overload in the subject. In alternative embodiments, provided are compositions and methods for: treating, ameliorating, or slowing the progress of, or protecting (preventing) an individual or a patient against heart failure; or, reducing LV hypertrophy, increasing LV peak pressure development, and/or improving LV peak pressure decay in a pressure-overload in an individual in need thereof.

BACKGROUND

Adenylyl cyclase (AC) is a transmembrane protein in cardiac myocytes and other cells, the effector molecule for β-adrenergic receptor (bAR) and other G protein-coupled receptors, which regulates the conversion of adenosine triphosphate (ATP) to 30,50-cyclic adenosine monophosphate (cAMP) and thereby initiates a variety of intracellular signaling cascades that influence heart function and additional physiological events.

There are 9 membrane-bound isoforms of mammalian ACs, each consisting of 2 transmembrane domains and 2 cytoplasmic domains (C1 and C2). The C1 and C2 domains form the catalytic core of AC (FIG. 1A). When expressed as a fusion protein, C1C2 is soluble and retains forskolin-stimulated catalytic activity (1).

C1C2 contains binding sites for Gas, Gai, forskolin, ATP, $Mg^{2+}$, the regulator of G protein signaling (RGAS2), protein associated with Myc (PAM), Snapin, Ric8a, A-kinase-anchoring protein (AKAP79), protein kinase C, PH domain leucine-rich protein phosphatase 2 (PHLPP2) and phosphorylation and dephosphorylation sites for protein kinase A. Interactions of these factors alters the conformation of C1C2 and regulates AC activity (2).

Increased cardiac expression of AC type 6 (AC6), a dominant AC isoform expressed in mammalian cardiac myocytes (3), has protean beneficial effects on the failing left ventricle (LV), including: 1) increased survival in genetically-induced cardiomyopathy (4) and in acute myocardial infarction (5); 2) reduced action potential duration (6), facilitated atrioventricular (AV) conduction (7), and reduced AV block (5); 3) reductions in both LV dilation and pathological hypertrophy (4,8); 4) beneficial effects on $Ca^{2+}$ handling via altered activity of SERCA2a and phospholamban (PLB) (9,10); and 5) increased cardiac troponin I phosphorylation (11).

These beneficial effects, consistent in several species and models, appear in large part to not depend upon increased cAMP generation. A phase 2 randomized clinical trial in patients with symptomatic heart failure (HF) and reduced ejection fractions showed that intracoronary AC6 gene transfer appears to be safe and potentially effective, and not associated with increased cardiac arrhythmias (12). Even so, there may be advantages in selecting a transgene that attenuates bAR responsiveness when treating HF.

We generated a catalytically inactive AC6 mutant (AC6mut) molecule by replacing Ala with Asp at position 426 in AC6's catalytic core. This AC6mut is catalytically inactive (does not generate cAMP) but retains the cellular distribution pattern and favorable signaling effects associated with normal AC6, thereby providing compelling evidence that the beneficial effects of AC6 do not require increased cAMP generation (13). AC6mut seemed an ideal candidate for the treatment of HF, retaining the beneficial effects of the parent AC6 while circumventing the potential deleterious effects of sustained cAMP generation. However, a shortcoming of both AC6mut and AC6 is that the molecules are too large to insert into an adeno-associated virus (AAV) with regulated expression, therefore only constitutive expression would be possible, a potential limitation.

Pharmacological inotropes, which increase LV function, for example, dobutamine, dopamine, milrinone, have consistently failed to enhance calcium handling in cardiac myocytes because of adverse effects of increased cardiac cAMP levels.

SUMMARY

In alternative embodiments, provided are isolated or recombinant, or chimeric, polypeptides comprising a first peptide sequence and a second peptide sequence, wherein the first peptide sequence comprises or consists of a sequence as set forth in SEQ ID NO:1 and the second peptide sequence comprises or consists of a sequence as set forth in SEQ ID NO:2, wherein the first peptide sequence and the second peptide sequence are operably linked. In alternative embodiments, of the isolated or recombinant, or chimeric, polypeptides, the first peptide sequence and the second peptide sequence are operably linked via a fusion or a linker peptide, or amino acid sequence.

In alternative embodiments, provided are isolated or recombinant nucleic acids (polynucleotides) or nucleic acid sequences encoding an isolated or recombinant, or chimeric, polypeptide as provided herein.

In alternative embodiments, provided are isolated or recombinant nucleic acids or nucleic acid sequences encoding the first peptide sequence as provided herein, or an isolated or recombinant nucleic acid nucleic acid encoding an amino acid sequence as set forth in SEQ ID NO:1, wherein optionally the first peptide is encoded by a nucleic acid sequence comprising or consisting of a sequence as set forth in SEQ ID NO:6, or having a sequence as set forth in SEQ ID NO:6.

In alternative embodiments, provided are isolated or recombinant nucleic acids or nucleic acid sequences encoding the second peptide sequence as provided herein, or an isolated or recombinant nucleic acid nucleic acid encoding an amino acid sequence as set forth in SEQ ID NO:2, wherein optionally the first peptide is encoded by a nucleic acid sequence comprising or consisting of a sequence as set forth in SEQ ID NO:7, or having a sequence as set forth in SEQ ID NO:7.

In alternative embodiments of an isolated or recombinant nucleic acid or nucleic acid sequence as provided herein:
the linker sequence comprises or consists of a nucleic acid sequence as set forth in SEQ ID NO:3, or has a sequence as set forth in SEQ ID NO:3; and/or
the nucleic acid sequence comprises or consists of a sequence as set forth in SEQ ID NO:4, or having a sequence as set forth in SEQ ID NO:4, or the nucleic acid sequence encodes a polypeptide having a sequence as set forth in SEQ ID NO:5.

In alternative embodiments, provided are vectors or expression constructs (e.g., recombinant viruses) comprising or having contained therein an isolated or recombinant nucleic acid, or nucleic acid sequence, as provided herein. In alternative embodiments, the vector is selected from the group consisting of an adeno-associated virus (AAV), a lentivirus, an adenovirus, and a plasmid. In alternative embodiments, the AAV is selected from the group consisting of AAV1, AAV2, AAV3, AAV4, AAV5, AAV6, AAV7, AAV8, AAV9, AAV10 AAV11, AAV12, pseudotyped AAV, a rhesus-derived AAV, AAVrh8, AAVrh10 and AAV-DJan AAV capsid mutant, an AAV hybrid serotype, an organtropic AAV, a cardiotropic AAV, and a cardiotropic AAVM41 mutant.

In alternative embodiments, provided are isolated, recombinant or engineered cells or host cells comprising a vector or expression construct as provided herein, or an isolated or recombinant nucleic acid, or nucleic acid sequence, as provided herein, wherein optionally the isolated, recombinant or engineered cell or host cell is or is derived from a mammalian, a human, a non-human primate, a monkey, a mouse, a rat, a guinea pig, a rabbit, a hamster, a goat, a bovine, an equine, an ovine, a canine or a feline cell.

In alternative embodiments, provided are non-human transgenic animals comprising or having contained therein the host cell as provided herein, or as a heterologous sequence, the non-human transgenic animal comprises or has contained therein an isolated or recombinant nucleic acid, or nucleic acid sequence, as provided herein.

In alternative embodiments, provided are methods for:
treating, ameliorating, slowing the progress of, or preventing a heart failure in a subject in need thereof,
reducing left ventricular (LV) hypertrophy in a subject in need thereof,
increasing LV peak pressure development in a subject in need thereof, and/or
reducing cAMP production and/or improving LV peak pressure decay in a pressure-overload in a subject in need thereof,
the method comprising:
(a) administering to the subject:
(i) an isolated or recombinant nucleic acid, or nucleic acid sequence, of as provided herein,
(ii) a vector or expression construct as provided herein,
(iii) a host cell as provided herein, or
(iv) an isolated or recombinant, or chimeric, polypeptide as provided herein, or
(b) (i) providing or having provided a therapeutic composition comprising:
(1) an isolated or recombinant nucleic acid, or nucleic acid sequence, as provided herein,
(2) a vector or expression construct as provided herein,
(3) a host cell as provided herein, or
(4) an isolated or recombinant, or chimeric, polypeptide as provided herein; and
(ii) administering or having administered to the subject in need thereof a therapeutically effective amount of the therapeutic composition,
thereby:
treating, ameliorating, slowing the progress of, or preventing a heart failure in the subject in need thereof,
reducing left ventricular (LV) hypertrophy in the subject in need thereof,
increasing LV peak pressure development in the subject in need thereof, and/or
reducing cAMP production and/or improving LV peak pressure decay in a pressure-overload in the subject in need thereof, In alternative embodiments of methods as provided herein the administration to the subject in need thereof:
reduces left ventricular (LV) hypertrophy, wherein the administration to the subject in need thereof increases LV peak pressure development;
reduces cAMP production and/or improves LV peak pressure decay in a pressure-overload in the subject; and/or
comprises use or administration of: a vector or expression construct as provided herein, or a host cell as provided herein.

In alternative embodiments, provided are methods for enhancing calcium handling in a cardiac myocyte without increasing cAMP generation, comprising administering to or implanting or transfecting into to the myocyte: an isolated or recombinant nucleic acid, or nucleic acid sequence, as provided herein, a vector or expression construct as provided herein, or an isolated or recombinant, or chimeric, polypeptide as provided herein, wherein expression of the nucleic acid sequence enhances calcium handling. In alternative embodiments, calcium handling is measured by uptake and release of calcium.

In alternative embodiments of methods as provided herein, administration is by intravenous (IV) injection, intra-arterial (IA) injection, or intracoronary injection.

In alternative embodiments, provided are methods the isolated or recombinant nucleic acid, or isolated or recombinant or chimeric polypeptide, is formulated in a liquid, a gel, a hydrogel, a vesicle, a liposome, a nanoparticle, a nanolipid particle, a powder or an aqueous or a saline formulation and wherein the nucleic acid is optionally in a vector or an expression construct.

In alternative embodiments of methods as provided herein, the cardiac myocyte is selected, derived from or isolated from a mammalian, a human, a non-human primate, a monkey, a mouse, a rat, a guinea pig, a rabbit, a hamster, a goat, a bovine, an equine, an ovine, a canine or a feline subject or host.

In alternative embodiments, provided are uses of:
an isolated or recombinant nucleic acid, or nucleic acid sequence, of as provided herein,
a vector or expression construct as provided herein,
a host cell as provided herein, or an isolated or recombinant, or chimeric, polypeptide as provided herein;

in the manufacture of a medicament for treating, ameliorating or protecting (preventing) an individual or a patient against heart failure, or reducing left ventricular (LV) hypertrophy, increasing LV peak pressure development, and/or increasing that rate of LV peak pressure decay in an individual in need thereof.

In alternative embodiments, provided are isolated or recombinant nucleic acids, or nucleic acid sequences as provided herein, for use in treating, ameliorating or protecting (preventing) an individual or a patient against heart failure, or reducing left ventricular (LV) hypertrophy, increasing LV peak pressure development, and/or increasing that rate of LV peak pressure decay in an individual in need thereof.

In alternative embodiments, provided are vectors or expression constructs as provided herein, or a host cell as provided herein, for use in treating, ameliorating or protecting (preventing) an individual or a patient against heart failure, or reducing left ventricular (LV) hypertrophy, increasing LV peak pressure development, and/or increasing that rate of LV peak pressure decay in an individual in need thereof.

In alternative embodiments, provided are isolated or recombinant, or chimeric, polypeptides as provided herein, for use in treating, ameliorating or protecting (preventing) an individual or a patient against heart failure, or reducing left ventricular (LV) hypertrophy, increasing LV peak pressure development, and/or increasing that rate of LV peak pressure decay in an individual in need thereof.

The details of one or more exemplary embodiments as provided herein are set forth in the accompanying drawings and the description below. Other features, objects, and advantages of the invention will be apparent from the description and drawings, and from the claims.

All publications, patents, patent applications cited herein are hereby expressly incorporated by reference for all purposes.

DESCRIPTION OF DRAWINGS

The drawings set forth herein are illustrative of exemplary embodiments provided herein and are not meant to limit the scope of the invention as encompassed by the claims.

FIG. 1A-G:

FIG. 1A schematically illustrates an exemplary C1C2 construct that forms the catalytic core; M1 and M2, transmembrane domains of AC6; C1 and C2, cytoplasmic domains of AC6; Linker, 12 amino acids;

FIG. 1B illustrates an immunoblotting gel showing how C1C2 protein was detected using an anti-AU1 tag antibody in NRCM after gene transfer with Ad5.C1C2 (200 vp/cell);

FIG. 1C illustrates and image of double-immunofluorescence staining of C1C2 protein in NRCM using anti-AU1 antibody (red); anti-caveolin 3 (Cav-3) antibody (green); yellow indicates co-localization of C1C2 with caveolin;

FIG. 1D-E illustrates data showing how NRCM underwent Ad5.C1C2 gene transfer and the amount of cAMP production in response to NKH477, a forskolin analog (FIG. 1D) or 10 mM Iso (10 min) (FIG. 1E); cardiac myocytes expressing C1C2 showed increased catalytic activity in a dose-dependent manner after stimulation with NKH477 (FIG. 1D) (activates AC) but reduced cAMP activity in response to bAR (Iso) stimulation (FIG. 1E); results were confirmed in 3 separate experiments; a representative experiment is shown with triplicate samples; bars denote mean±SE; p values are from Student's t-test (unpaired, 2-tailed);

FIG. 1F illustrates an image of co-immunoprecipitation and immunoblotting to immunodetect molecules in the Akt signaling pathway to indicate that C1C2 and AC6 expression were associated with similar increases in phosphorylation of Akt, GSK3a/b, MDM2, and p70S6k, suggesting that the effect does not require AC6-mediated cAMP production;

FIG. 1G illustrates an image of immunoprecipitation and immunoblotting data showing C1C2 expression was associated with phosphorylation of ERK1/2, p38 MAPK, and aB-crystallin (CryAB, upper), interaction of CryAB and C1C2 detected by co-immunoprecipitation and immunoblotting (lower), in FIG. 1A-E Con denotes transgene negative mice. Iso ¼ isoproterenol; NRCM ¼ neonatal rat cardiac myocytes, as described in detail in Example 1, below.

FIG. 2A-E:

FIG. 2A illustrates a Northern blot image of RNA levels showing that increased C1C2 mRNA and protein were documented from 2 founder lines (L1, L2) that showed different expression levels of mRNA, but similar levels of protein;

FIG. 2B graphically illustrates data of studies where transmural LV samples underwent stimulation with Iso (10 mM, 10 min) or NKH477 (AC activator; 10 mM, 10 min); Net Iso cAMP production was reduced in LV from C1C2 mice; Basal and AC-dependent cAMP showed no group differences;

FIG. 2C graphically illustrates data of studies where PKA activity was unchanged by increased C1C2 expression;

FIG. 2D graphically illustrates data of studies showing that despite diminished Iso-stimulated cAMP production in LV from C1C2 mice, there were no group differences (C1C2 vs. Con) in LV peak +dP/dt, LV peak –dP/dt, HR, or LVP through a wide range of Iso doses;

FIG. 2E graphically illustrates data of histological inspection of transmural LV samples stained with H&E and Masson's trichrome showed normal cardiac histology without fibrosis in C1C2 mice at 8 months of age. (B to E) Con denotes transgenic negative mice. H&E, hematoxylin and eosin; HR ¼ heart rate; Iso ¼ isoproterenol; LV ¼ left ventricle; LVP ¼ LV developed pressure, as described in detail in Example 1, below.

FIG. 3A-B graphically illustrate data showing: in Con, 7 days of continuous Iso infusion tended to reduce LV peak +dP/dt (A) and LV peak –dP/dt (B). In contrast, in C1C2 mice, 7 days of Iso infusion increased LV peak +dP/dt (p ¼ 0.026) (FIG. 3A) and peak –dP/dt (p ¼ 0.006) (FIG. 3B); no between-group differences were seen in pre-Iso LV +dP/dt (p ¼ 0.22) or LV–dP/dt (p ¼ 0.27);

FIG. 3C graphically illustrates data showing that similarly, continuous Iso infusion was associated with reduced LV developed pressure in Con mice (p ¼ 0.012) but with increased LV developed pressure in C1C2 mice (p ¼ 0.016);

FIG. 3D graphically illustrates data showing that heart rate showed no group differences within or between groups;

FIG. 3E graphically illustrates (as the upper image) data showing histological analysis of fixed transmural LV samples stained with Picro Sirius red (the histological image is shown as the lower image) showed increased LV fibrosis after 7 days (7 d) of continuous Iso infusion in Con mice only (p ¼ 0.02), but a between-group difference in fibrosis at 7 days was not seen; Bars ¼ mean values; SE ¼ error bars; values in bars ¼ numbers of mice; Two-way ANOVA showed significant interaction of C1C2 on LV peak +dP/dt (p ¼ 0.012), LV peak –dP/dt (p ¼ 0.0009), and LVP (p ¼ 0.0003); numbers above bars indicate p values from within-group post hoc comparisons (Student t-test, unpaired, 2-tailed, Bonferroni correction); Con ¼ transgene negative mice; other abbreviations as in FIGS. 1 and 2, as described in detail in Example 1, below.

FIG. 4A-B graphically illustrate data showing representative Indo-1 $Ca^{2+}$ recordings from cardiac myocytes from C1C2 and Con mice showing unstimulated (FIG. 4A) and briefIso-stimulated $Ca^{2+}$ transients (Iso; 10 mM) (FIG. 4B);

FIG. 4C graphically illustrates data showing summary data of unstimulated (basal) and Iso-stimulated $Ca^{2+}$ release (systolic-diastolic $Ca^{2+}$) show no group difference before stimulation; however, $Ca^{2+}$ release in the presence of Iso was increased in cardiac myocytes from both groups and was higher in cardiac myocytes from C1C2 than Con mice (p ¼ 0.02);

FIG. 4D graphically illustrates data showing time to peak $Ca^{2+}$ release in the presence of Iso was decreased in cardiac myocytes from both groups and was lower in cardiac myocytes from C1C2 than in Con mice before (p ¼ 0.025) and after (p ¼ 0.047) brief Iso stimulation;

FIG. 4E graphically illustrates data showing that Tau was reduced by Iso in both groups, but no between-group differences were seen;

FIG. 4F illustrates images showing LV expression and phosphorylation of signaling proteins that modulate $Ca^{2+}$ handling (PKA, PLB, TnI, S100A1) showed no group differences (see FIG. 4C-E), bars ¼ mean values; error bars ¼ SE; numbers in bars ¼ number of cardiac myocytes, values above bars ¼ p values from Student's t-test (unpaired, 2-tailed); abbreviations as in FIGS. 1 to 3, as described in detail in Example 1, below.

FIG. 5A-D illustrate $Ca^{2+}$ transients: FIG. 5A graphically illustrates representative Indo-1 $Ca^{2+}$ recordings from cardiac myocytes from C1C2 and Con mice after 7 days of Iso infusion; FIG. 5B graphically illustrates basal $Ca^{2+}$ release (systolic-diastolic $Ca^{2+}$) show increased $Ca^{2+}$ release in C1C2 cardiac myocytes (p ¼ 0.02); FIG. 5C graphically illustrates time to peak $Ca^{2+}$ transient was reduced in C1C2 cardiac myocytes (p ¼ 0.002); FIG. 5D graphically illustrates time to $Ca^{2+}$ decline (Tau) was reduced in cardiac myocytes from C1C2 mice (p ¼ 0.04);

FIG. 5E graphically illustrates LV SERCA2a content was 2.6-fold greater in C1C2 than in Con mice after 7 days of Iso infusion (p ¼ 0.002; immunoblot below bar graph), although before Iso infusion, the fold difference (C1C2 vs. Con) was not significant (p ¼ 0.29);

FIG. 5F graphically illustrates cardiac-directed C1C2 expression was associated with an 11.5-fold increase in LV P-Rex2 mRNA before (p ¼ 0.001) and 7.5-fold after 7 days of Iso infusion (p ¼ 0.002) vs. Con;

FIG. 5G graphically illustrates data showing that no group differences in expression of PKA, PLB, S100A1, or vinculin were seen; Phosphorylation of PKA, PLB, and TnI also showed no group differences;

Bars ¼ mean values; SE ¼ error bars; number in bars ¼ numbers of cells (B to D) or mice (E, F); numbers above bars ¼ p values from Student t-test (unpaired, 2-tailed); Abbreviations as in FIGS. 1 to 5.

FIG. 6A-B illustrate exemplary nucleic acid and amino acid sequences as provided herein.

Figure 7A:
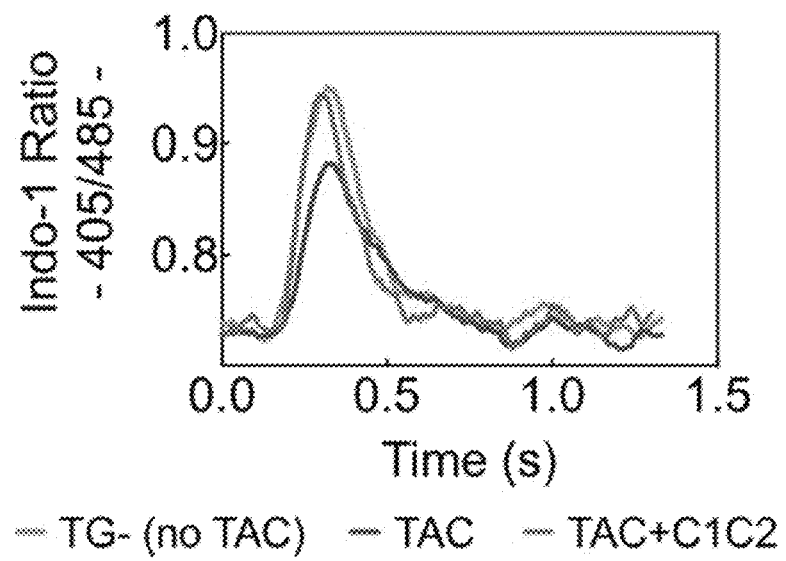
Figure 7B:
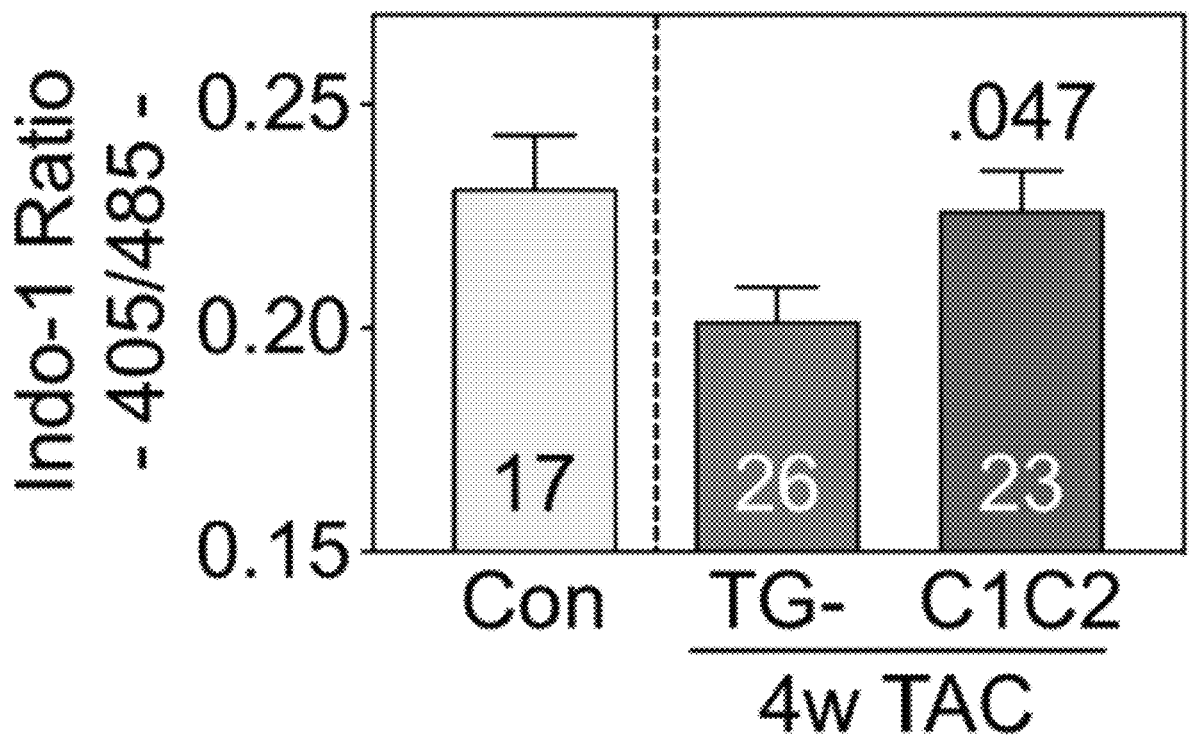
Figure 7C:
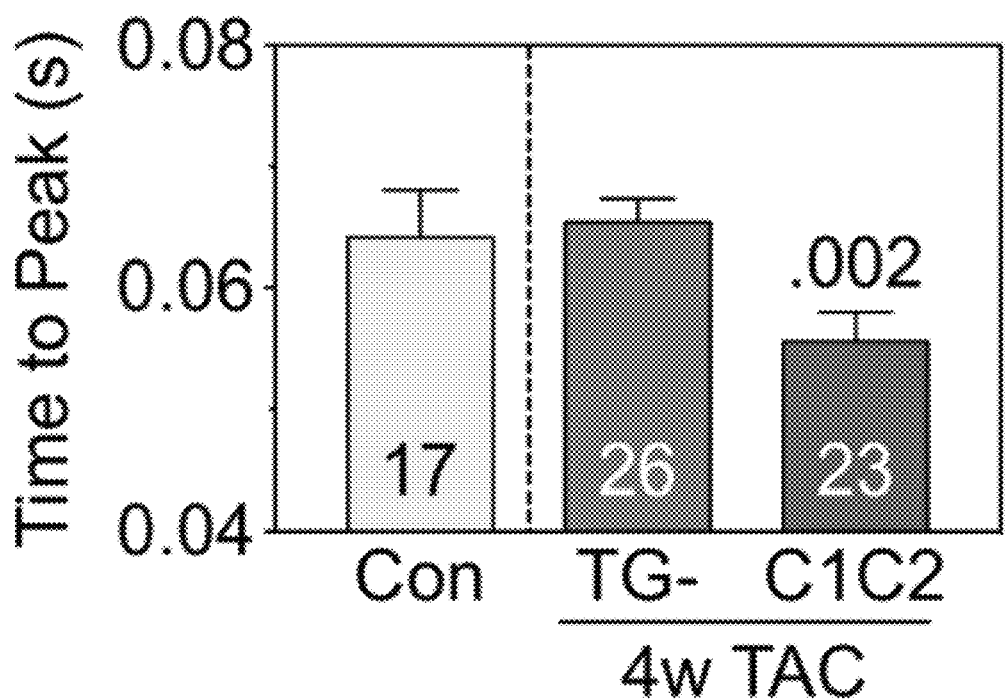
Figure 7D:
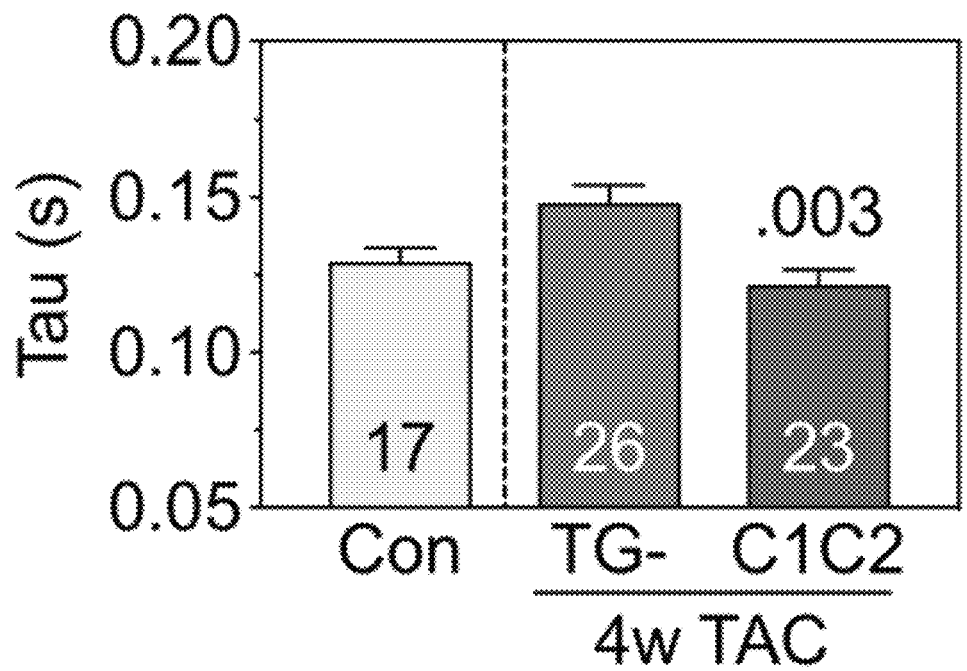

FIG. 7A-D illustrate studies where cardiomyocytes were isolated from control mice (Con: TG–, no TAC) and from transgene negative (TG–) and C1C2 mice four weeks (4 w) after TAC; and cytosolic Ca2+ transients were measured with a fluorescence microscope using the Ca2+ indicator, Indo-1 AM:

FIG. 7A graphically illustrates representative Indo-1 Ca2+ transient recordings from cardiomyocytes of the 3 groups;

FIG. 7B graphically illustrates Ca2+ transient amplitude was higher (p=0.047) in cardiac myocytes from C1C2 mice vs TG– mice 4 w after TAC;

FIG. 7C graphically illustrates time to peak Ca2+ transient was more rapid (p=0.002) in cardiac myocytes from C1C2 mice vs TG– mice 4 w after TAC;

FIG. 7D graphically illustrates data showing that the time constant of cytosolic Ca2+ decline (Tau) was more rapid (p=0.003) in cardiac myocytes from C1C2 mice vs TG– mice 4 w after TAC;

Data are mean +SE. Numbers in bars denote the number of cardiomyocytes per group, obtained from 6 mice per group (2-5 cells per animal, blinded to group identity); P values are from Student's t-test (unpaired, two tails) comparing TG– vs C1C2 4 w after TAC;

as discussed in detail in Example 3, below.

Figure 8A:
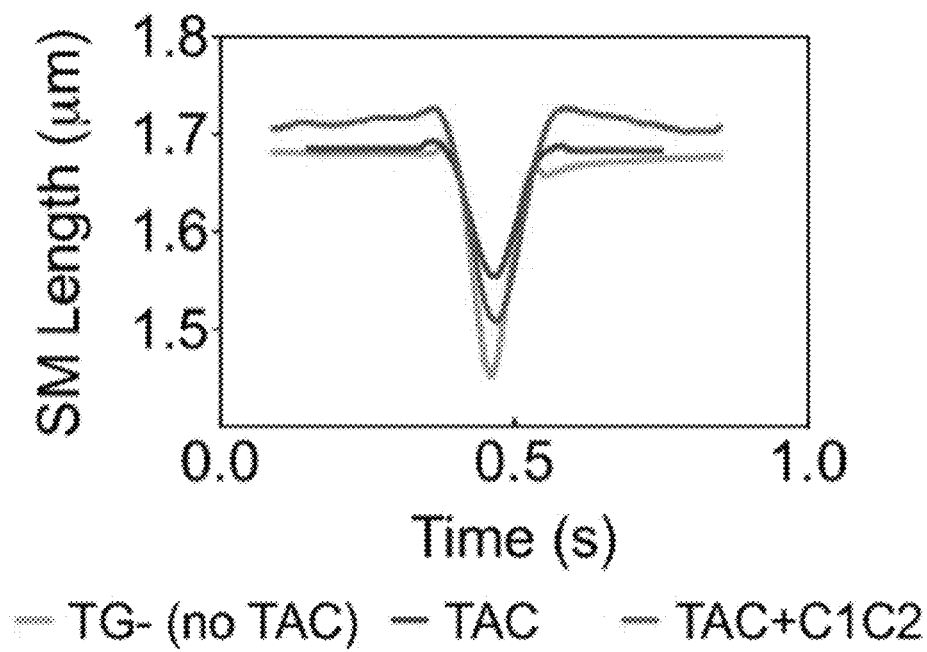
Figure 8B:
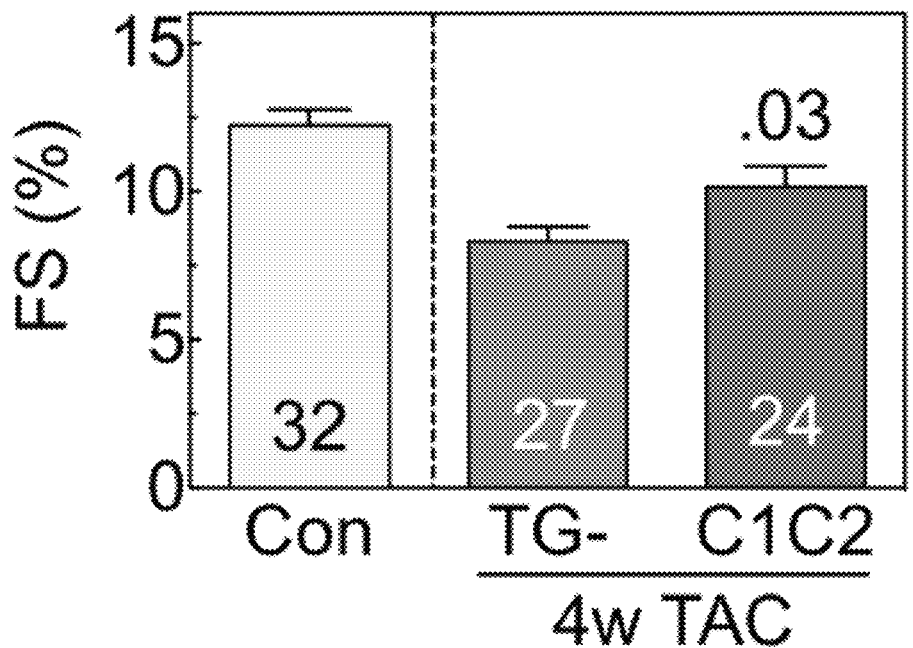
Figure 8C:
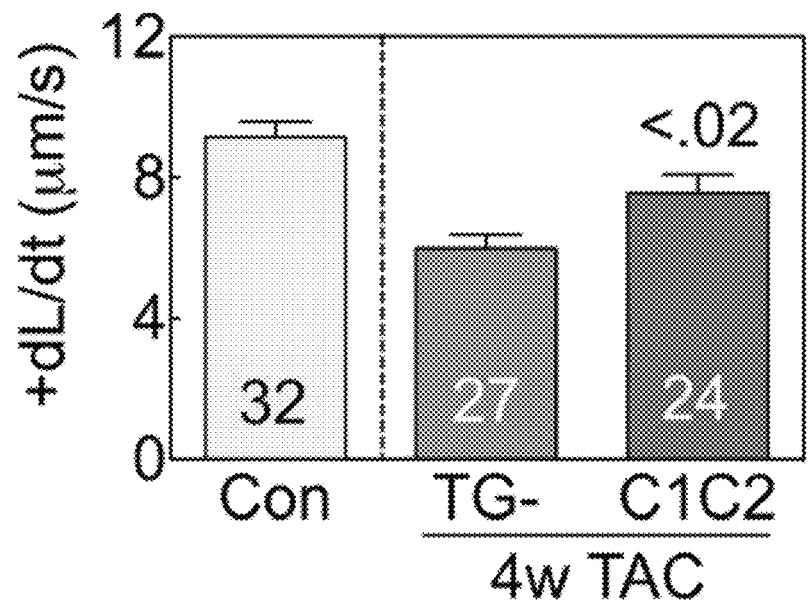
Figure 8D:
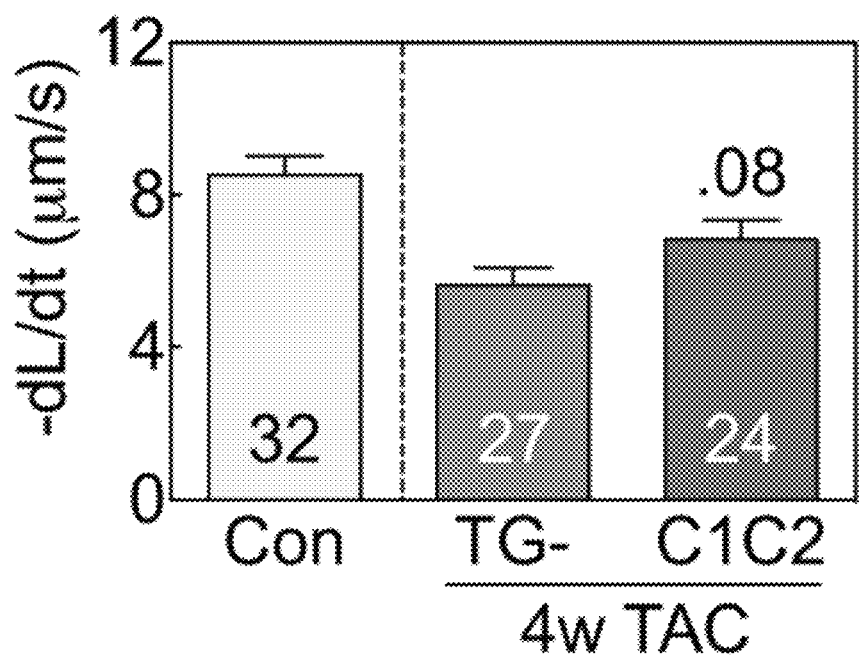

FIG. 8A-D: illustrate sarcomere shortening, where cardiomyocytes were isolated from control mice (Con: no TAC or C1C2 expression) and from transgene negative (TG–) and C1C2 mice four weeks (4 w) after TAC; sarcomere length and shortening were measured using edge detection:

FIG. 8A graphically illustrates representative sarcomere shortening traces recorded from cardiomyocytes from control (Con) mice (No TAC, TG–), and C1C2 and TG– mice 4 w after TAC;

FIG. 8A graphically illustrates fractional shortening (FS) was higher (p=0.03) in cardiac myocytes from C1C2 mice vs TG– mice 4 w after TAC;

FIG. 8C graphically illustrates peak rate of sarcomere shortening (+dL/dt) was higher in cardiac myocytes from mice with C1C2 expression vs TG– mice 4 w after TAC (p<0.02);

FIG. 8D graphically illustrates peak rate of sarcomere relaxation (–dL/dt) tended to be more rapid in cardiac myocytes from C1C2 mice vs TG– mice 4 w after TAC (p=0.08);

Data are mean +SE. Numbers in bars denote the number of cardiomyocytes, obtained from 6 mice per group (4-6 cells per mouse, blinded to group identity); P values are from Student's t-test (unpaired, two tails) comparing TG– vs C1C2 4 w after TAC;

as discussed in detail in Example 3, below.

Figure 9A:
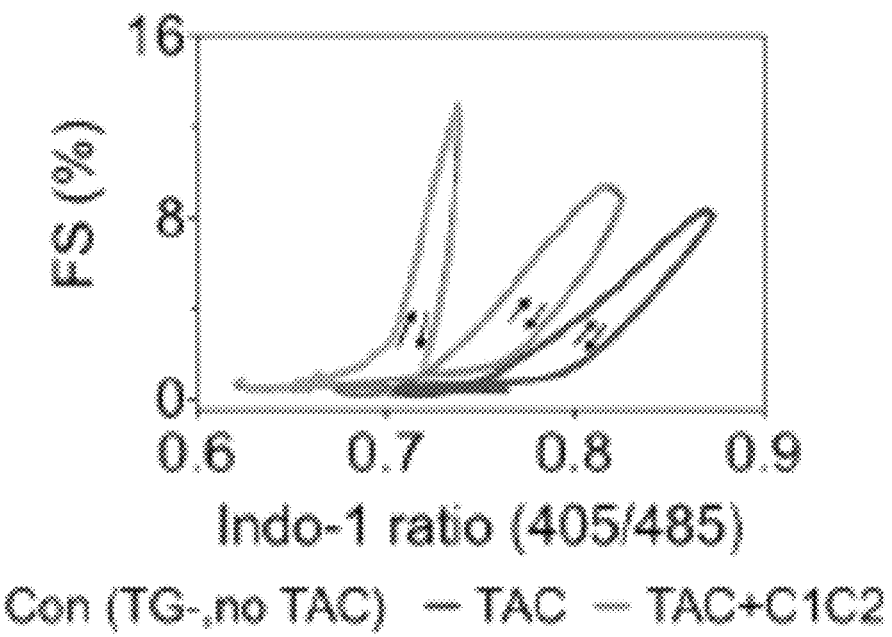
Figure 9B:
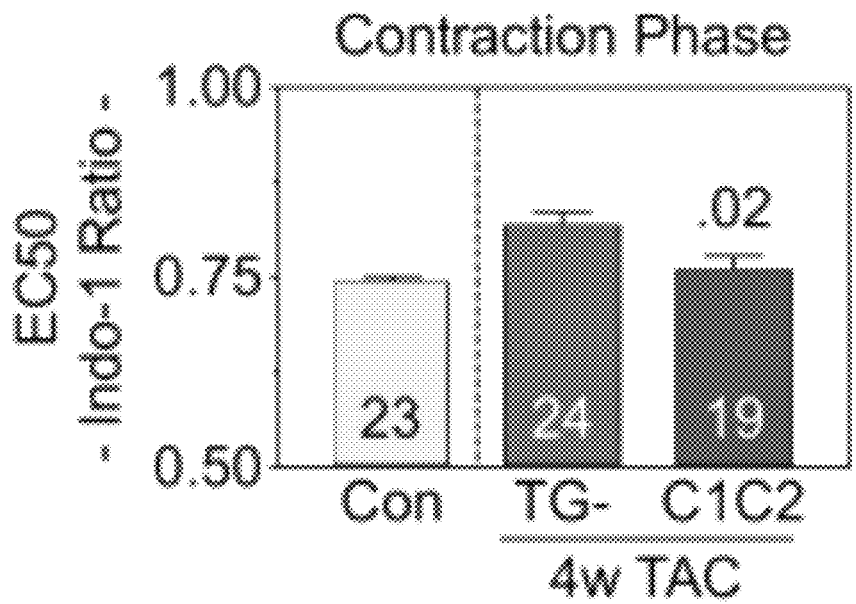
Figure 9C:
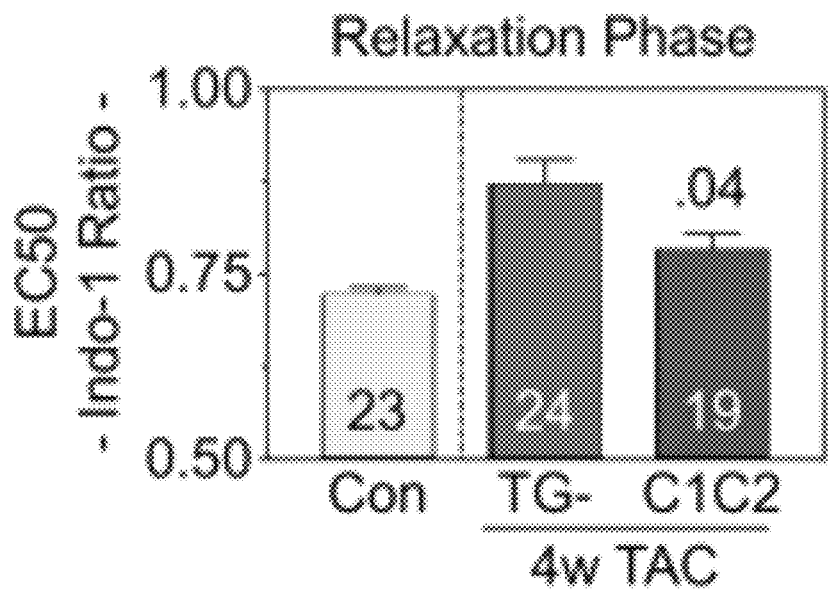

FIG. 9A-C illustrate myofilament sensitivity, where myofilament sensitivity to Ca2+ was analyzed based on Ca2+ transients and simultaneous sarcomere shortening in cardiomyocytes from Control (Con) mice (TG–, no TAC), and TG negative mice and C11C2 mice 4 weeks after TAC:

FIG. 9A graphically illustrates mean phase loops from cardiomyocytes from each group. Arrows indicate loop direction. The loop from cardiac myocytes isolated from C1C2 mice 4 w after TAC shows a leftward shift vs the TG negative group, indicating increased myofilament sensitivity to cytosolic Ca2+;

FIG. 9B graphically illustrates data showing that during contraction, EC50 for cytosolic Ca2+(Indo-1 ratio) was reduced in C1C2 group (p=0.02) confirming increased myofilament Ca2+ sensitivity;

FIG. 9C graphically illustrates that curing relaxation, EC50 was lower in cardiac myocytes from the C1C2 mice (p=0.04), which indicates increased myofilament Ca2+ sensitivity in diastole;

Error bars denote mean±SE from 19-24 cardiomyocytes per group, isolated from 6 mice per group (3-4 cells per mouse, blinded to group identity); P value is from Student's t-test (unpaired, two-tailed);

as discussed in detail in Example 3, below.

Figure 10A:
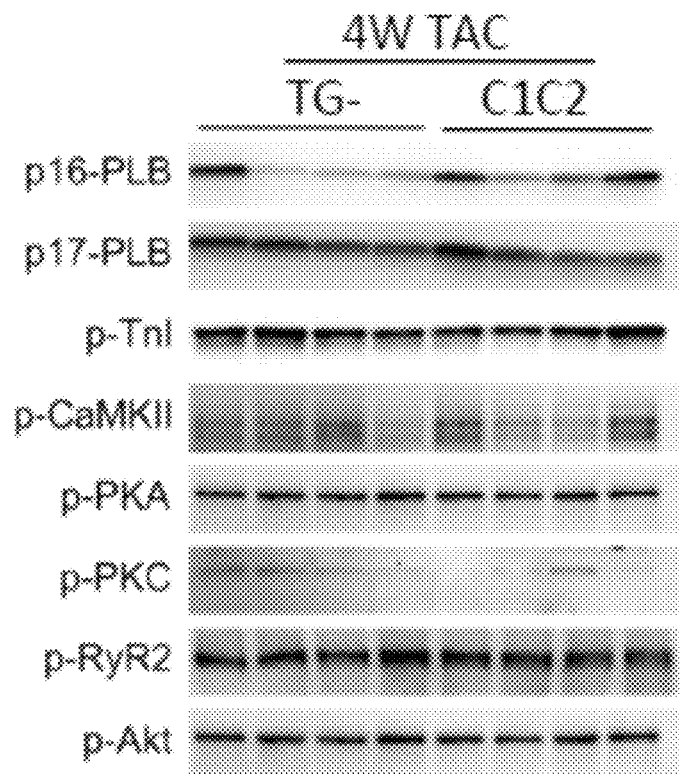
Figure 10B:
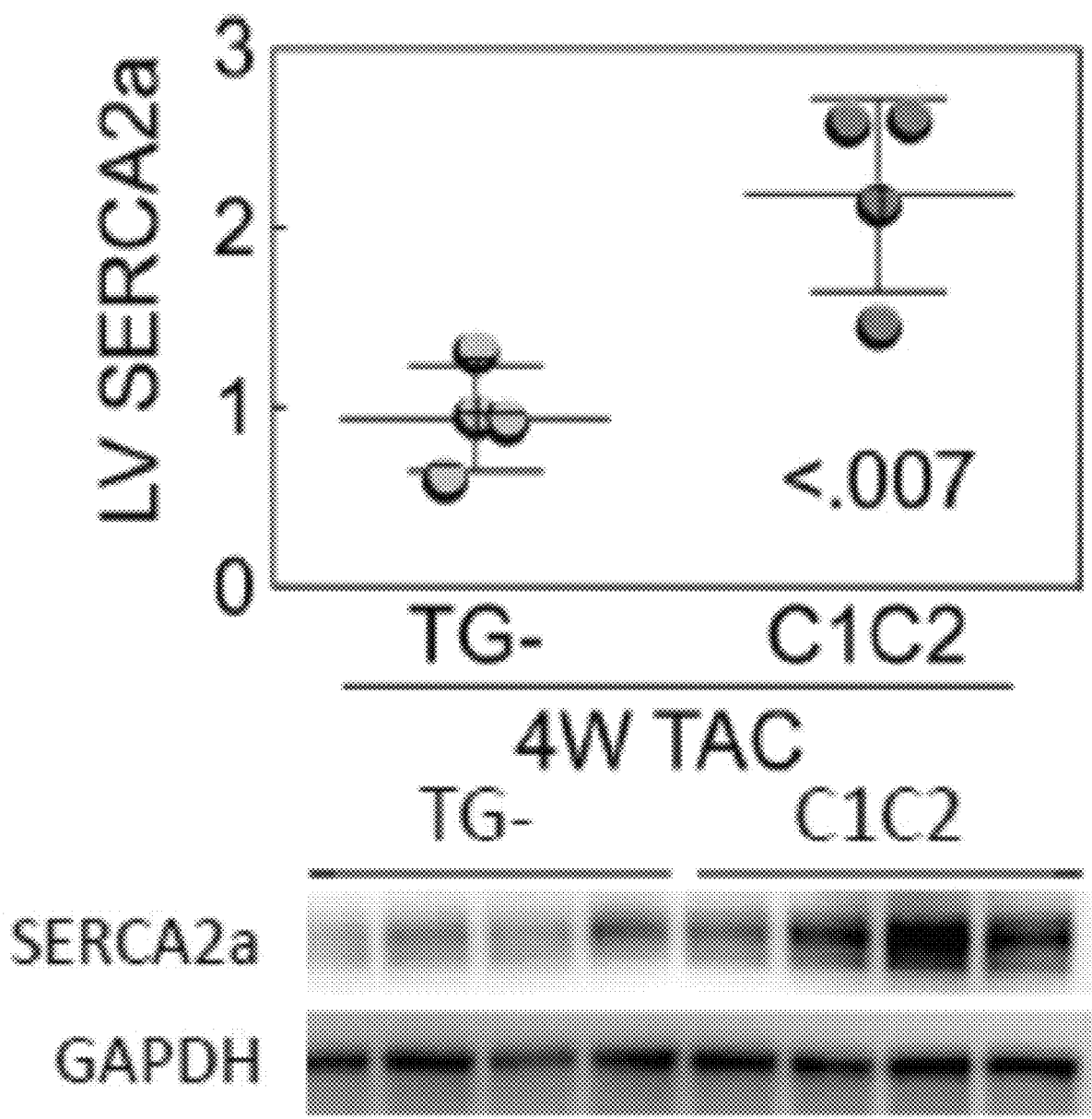

FIG. 10A-B illustrate an immunoblotting study:

FIG. 10A graphically illustrates data showing no group differences in LV phosphorylated PLB (p16 or p17), TnI, CaMKII, PKA, PKC, RyR2 or Akt were seen 4 w after TAC;

FIG. 10A illustrates images of gel data showing that LV SERCA2a content was 2.3-fold higher in C1C2 4 weeks after TAC (p<0.007);

FIG. 10B: the graphically shown data in FIG. 10B are standardized to GAPDH and show relative group differences, error bars denote mean±SE. P value is from Student's t-test (unpaired, two-tailed);

as discussed in detail in Example 3, below.

Figure 11A:
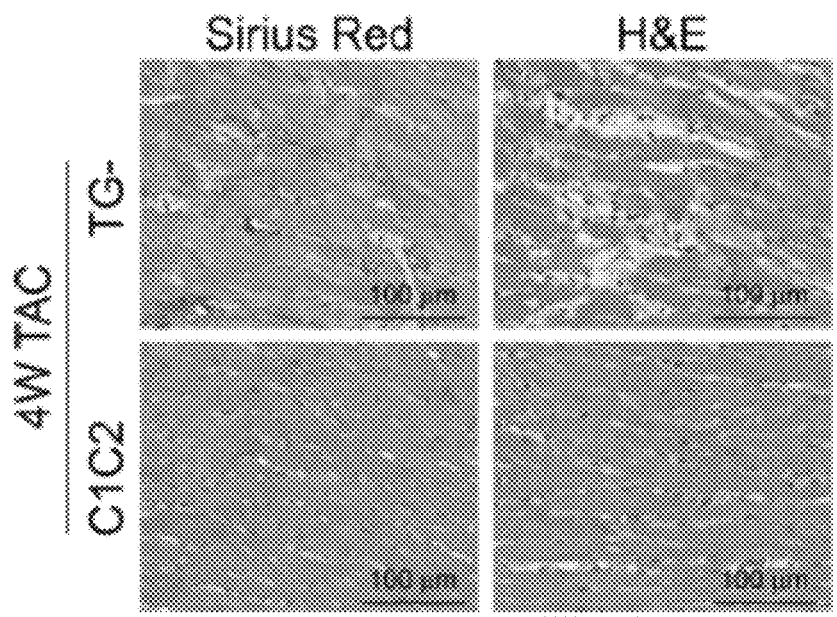
Figure 11B:
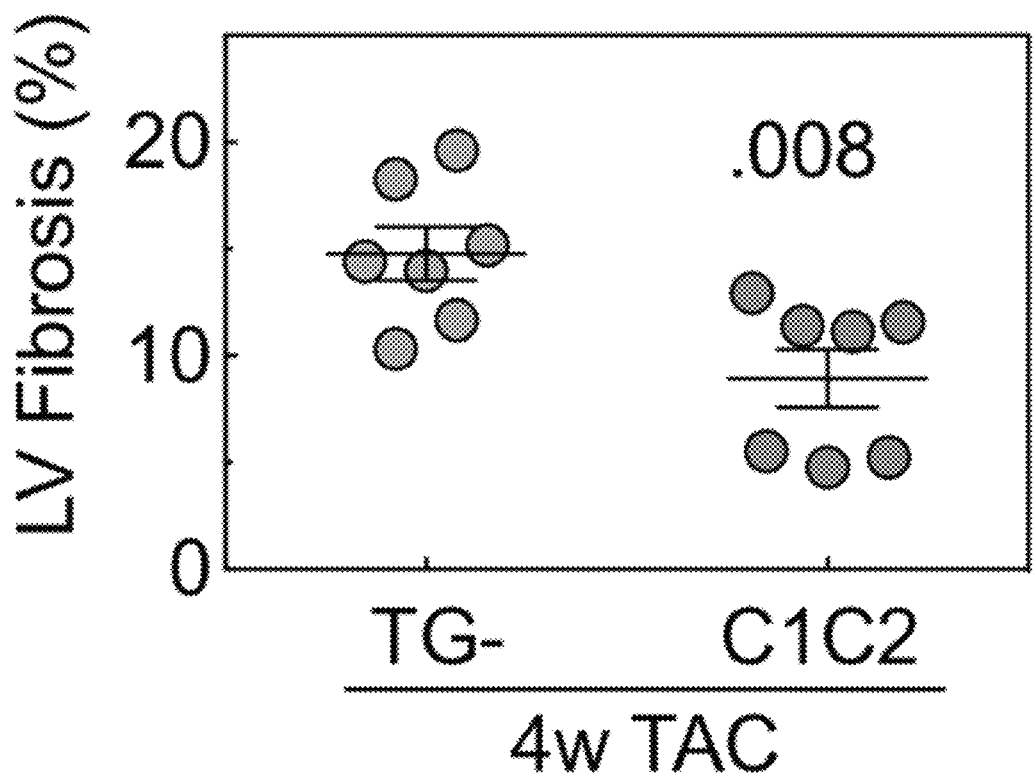

FIG. 11A-B illustrate LV fibrosis:

FIG. 11A illustrates representative images of transmural LV samples stained with picrosirius red and hematoxylin and eosin (H&E), 4 w after TAC (10× magnification);

FIG. 11B graphically illustrates evaluation of fibrosis using ImageJ™ showed less fibrosis in LV from C1C2 mice (p=0.008), error bars denote mean±SE. P value is from Student's t-test (unpaired, two-tailed);

as discussed in detail in Example 3, below.

Like reference symbols in the various drawings indicate like elements.

DETAILED DESCRIPTION

In alternative embodiments, provided are compositions, including products of manufacture and kits, and methods, for treating a heart failure in a subject in need thereof comprising administering to the subject a nucleic acid sequence as provided herein, thereby treating the subject. In alternative embodiments, the administration reduces left ventricular (LV) hypertrophy, increases LV peak pressure development, reduced cAMP production and/or improves LV peak pressure decay in a pressure-overload in the subject. In alternative embodiments, provided are compositions and methods for: treating, ameliorating or protecting (preventing) an individual or a patient against heart failure; or, reducing LV hypertrophy, increasing LV peak pressure development, and/or improving LV peak pressure decay in a pressure-overload in an individual in need thereof.

In alternative embodiments, provided are compositions, including products of manufacture and kits, and methods, for altering intracellular signaling in a manner that enhances calcium ($Ca^{2+}$) handling in cardiac myocytes, and does so without being linked to cell surface beta-adrenergic receptors. In alternative embodiments, provided are compositions, including products of manufacture and kits, and methods, for treating, ameliorating or protecting (preventing) an individual or a patient against heart failure. In alternative embodiments, provided are chimeric or synthetic polypeptide comprising: a C1 and a C2 domain of an adenylyl cylase (AC), and lacking all AC transmembrane domains, and the C1 and the C2 domains have an AC catalytic activity, and nucleic acids encoding them, and expression vehicles, vectors, recombinant viruses, or equivalents expressing them, and engineered or recombinant expressing them.

Figure 1A:
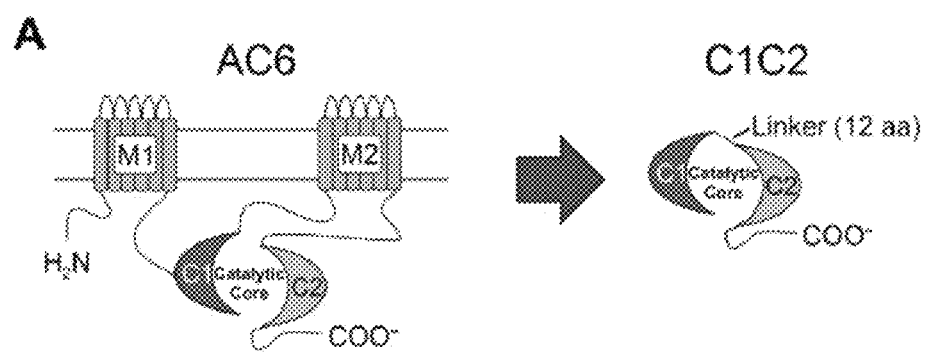

In alternative embodiments, provided are truncated AC6 polypeptides made by eliminating the amino terminus and the 2 trans-membrane domains of AC6 and subsequently fusing the 2 cytoplasmic domains (C1 and C2) with a 12-amino acid linker yields a C1C2 protein (FIG. 1A). C1C2 has an intact catalytic domain but is disengaged from membrane-associated bARs and is therefore less responsive to bAR stimulation in intact cells. C1C2 is sufficiently small to be inserted in an AAV vector with a regulated expression cassette, enabling turning off transgene expression when desired. Many of the beneficial effects of AC6 that we have described are independent of cAMP generation and appear, instead, to involve intracellular AC6-protein interactions (10,13).

We speculated that elimination of the trans-membrane regions of AC6 (FIG. 1A) would facilitate intracellular distribution and would include the region of the AC6 molecule (C1C2) most likely engaged in protein-protein interactions (14). Initial tests using adenovirus-mediated C1C2 gene transfer in cultured cardiac myocytes confirmed our speculations vis-á-vis C1C2's beneficial effects on signaling and reduced cAMP generation, setting the stage for development of gene transfer of C1C2 as a potential therapy for HF. The goal of the current study was to perform mechanistic and translational studies of C1C2. Our hypothesis was that cardiac-directed expression of the cytoplasmic domains of AC6 would have beneficial effects on the heart.

Eliminating the two transmembrane domains of AC6 yields a protein with an intact catalytic domain that is disengaged from membrane-associated J3-adrenergic receptor stimulation, but with enhanced propensity for intracellular interactions with other proteins, which, ultimately, enhance Ca2+ handling and thus systolic and diastolic heart function. Transgenic mice with cardiac-directed expression of C1C2 exhibit resistance to sustained adrenergic stimulation compared with TG negative (control) siblings (JACC Basic & Translational Science 2016; 1:617-629). C1C2 gene transfer promotes enhanced Ca2+ handling, which is not offset by the potentially deleterious effects of increased cAMP levels. C1C2 molecule is sufficiently small that its coding sequence can be expresses in an adeno-associated virus vector, unlike AC6 or AC6 mutant.

Transgenic mice with cardiac-directed C1C2, a fusion protein of the intracellular C1 and C2 segments of adenylyl cyclase type 6, had normal left ventricular (LV) function, but diminished cAMP generation. Cardiac myocytes from C1C2 mice showed increased Ca2+ release. Mice underwent continuous isoproterenol infusion to stress the heart. In C1C2 mice, sustained isoproterenol infusion increased rather than decreased LV function. LV SERCA2a and Ca2+ release was increased. Reduced cAMP generation and resistance to catecholamine cardiomyopathy are attractive features of this potential heart failure therapeutic.

In alternative embodiments, a virus vector encoding C1C2 (AAV9.C1C2) as provided herein is suitable to use either intravenously or by intra-coronary infusion in patients with heart failure. In alternative embodiments, C1C2 gene transfer has beneficial effects on the failing human heart, and is effective regardless of ejection fraction (preserved or reduced). Thus, this embodiment can be used to treat individuals with heart failure, including the 6 million patients with heart failure in US, with 400,000 new cases diagnosed each year.

Generating and Manipulating Nucleic Acids

In alternative embodiments, provided are nucleic acids encoding polypeptides comprising a first peptide sequence and a second peptide sequence, wherein the first peptide sequence comprises or consists of a sequence as set forth in SEQ ID NO:1 and the second peptide sequence comprises or consists of a sequence as set forth in SEQ ID NO:2, wherein the first peptide sequence and the second peptide sequence are operably linked. In alternative embodiments, the isolated or recombinant nucleic acid or nucleic acid sequence encodes a first peptide sequence, and optionally the first peptide is encoded by a nucleic acid sequence comprising or consisting of a sequence as set forth in SEQ ID NO:6. In alternative embodiments, the isolated or recombinant nucleic acid or nucleic acid sequence encodes a second peptide, or an isolated or recombinant nucleic acid nucleic acid encoding an amino acid sequence as set forth in SEQ ID NO:2, wherein optionally the first peptide is encoded by a nucleic acid sequence comprising SEQ ID NO:7.

```
                                                SEQ ID NO: 1
MEMKEDINTKKED MMFHKIYIQK HDNVSILFAD IEGFTSLASQ

CTAQELVMTL NELFARFDKL AAENHCLRIK ILGDCYYCVS

GLPEARADHA HCCVEMGVDM IEAISLVREV TGVNVNMRVG

IHSGRVHCGV LGLRKWQFDV WSNDVTLANH MEAGGRAGRI

HITRATLQYL NGDYEVEPGR GGERNAYLKE QCIETFLILG

ASQKRKEEKA MLAKLQRT
```

```
                                                SEQ ID NO: 2
IPPAAAMYNR RLLHNILPKD VAAHFLARER RNDELYYQSC

ECVAVMFASI ANFSEFYVEL EANNEGVECL RLLNEIIADF

DEIISEERFR QLEKIKTIGS TYMAASGLNA STYDQVGRSH

ITALADYAMR LMEQMKHINE HSFNNFQMKI GLNMGPVVAG

VIGARKPQYD IWGNTVNVSS RMDSTGVPDR IQVTTDLYQV

LAAKGYQLEC RGVVKVKGKG EMTTY
```

```
                                                SEQ ID NO: 3
Linker- RANSMEGAAAGG
```

C1-Linker-C2 DNA Sequence (SEQ ID NO: 4)

For purposes of illustration and clarity only, the separate domains of this single exemplary polypeptide-encoding nucleic acid are separated, below:

```
BOLD: 5' untranslated region
Italics: C1 start
UNDERLINE: Linker between C1 and C2 domains
BOLD/ITALICS: AU1 tag
GTCTCTCCTCCCAGCACGTTGCC

ATG

GAGATGAAAGAAGACATCAACACAAAAAAAGAGGACATGATGTTCCAT

AAGATCTACATCCAGAAGCATGATAATGTCAGCATCCTGTTTGCGGACA

TTGAGGGCTTCACCAGCCTGGCCTCCCAGTGCACTGCACAGGAACTGGT

CATGACCTTGAATGAGCTCTTTGCCCGGTTTGACAAGCTGGCTGCGGAG

AATCACTGTCTGAGGATCAAGATCTTAGGAGACTGTTACTACTGCGTGT

CAGGGCTGCCCGAGGCCCGGGCAGATCACGCCCACTGCTGTGTGGAGAT

GGGGGTAGACATGATCGAAGCCATCTCGCTGGTGCGTGAGGTAACAGGT

GTGAACGTGAACATGCGTGTGGGCATCCACAGCGGACGTGTGCATTGCG

GCGTCCTTGGCCTACGGAAATGGCAGTTTGATGTCTGGTCAAACGATGT

GACCCTGGCTAACCACATGGAGGCCGGGGCCGGGCCGGCCGCATCCA

CATCACTCGGGCTACACTGCAGTACTTGAACGGGGACTATGAGGTGGAG

CCAGGCCGTGGTGGTGAACGCAATGCGTACCTCAAGGAGCAGTGCATTG

AGACCTTCCTCATACTTGGCGCCAGCCAAAAACGGAAGAGGAGAAAG

CCATGCTGGCCAAGCTTCAGCGGACACGGGCCAACTCCATGGAAGGA

GCTGCAGCGGGTGGAATTCCTCCTGCGGCGGCAATG

TACAACCGGAGGTTGCTGCATAACATTCTTCCCAAGGACGTGGCCGCCC

ACTTCCTGGCCCGGGAACGCCGCAACGATGAGCTGTACTACCAGTCGTG

TGAATGTGTGGCTGTCATGTTTGCCTCCATCGCCAATTTCTCGGAGTTCT

ACGTGGAGCTCGAGGCAAACAACGAGGGCGTGGAGTGCCTGCGGCTGC

TCAATGAGATCATCGCAGACTTTGACGAGATCATCAGTGAGGAGAGATT

CCGGCAGTTGGAGAAGATCAAGACCATCGGTAGCACCTACATGGCCGCC

TCTGGGCTAAATGCCAGCACCTATGACCAGGTCGGCCGCTCACACATCA

CGGCGCTGGCTGACTATGCCATGCGGCTCATGGAGCAGATGAAACACAT

CAATGAACACTCTTTCAACAATTTCCAGATGAAGATCGGGTTGAACATG

GGTCCGGTTGTAGCAGGCGTCATTGGGGCCCGAAAGCCACAGTATGACA
```

-continued

```
TCTGGGGAAATACCGTGAATGTTTCCAGTCGTATGGACAGCACTGGAGT

TCCTGACCGAATACAGGTGACTACGGACCTATACCAGGTTCTAGCTGCC

AAGGGCTACCAGCTGGAGTGTCGAGGGGTGGTCAAGGTGAAGGGAAAG

GGGGAGATGACCACCTAC
```

GACACTTACCGGTACATT

C1-linker-C2 Amino Acid Sequence
(SEQ ID NO: 5)

```
  1  LSSQHVAMEM KEDINTKKED MMFHKIYIQK HDNVSILFAD IEGFTSLASQ
 51  CTAQELVMTL NELFARFDKL AAENHCLRIK ILGDCYYCVS GLPEARADHA
101  HCCVEMGVDM IEAISLVREV TGVNVNMRVG IHSGRVHCGV LGLRKWQFDV
151  WSNDVTLANH MEAGGRAGRI HITRATLQYL NGDYEVEPGR GGERNAYLKE
201  QCIETFLILG ASQKRKEEKA MLAKLQRTRA NSMEGAAAGG IPPAAAMYNR
251  RLLHNILPKD VAAHFLARER RNDELYYQSC ECVAVMFASI ANFSEFYVEL
301  EANNEGVECL RLLNEIIADF DEIISEERFR QLEKIKTIGS TYMAASGLNA
351  STYDQVGRSH ITALADYAMR LMEQMKHINE HSFNNFQMKI GLNMGPVVAG
401  VIGARKPQYD IWGNTVNVSS RMDSTGVPDR IQVTTDLYQV LAAKGYQLEC
451  RGVVKVKGKG EMTTYDTYRY I
```

(encoding SEQ ID NO: 1)
SEQ ID NO: 6
```
GAGATGAAAGAAGACATCAACACAAAAAAAGA GGACATGATGTTCCATAAGATCTAC

ATCCAGAAGCATGATAATGTCAGCATCCTGTTTGCGGACATTGAGGGCTTCACCAGCC

TGGCCTCCCAGTGCACTGCACAGGAACTGGTCATGACCTTGAATGAGCTCTTTGCCCG

GTTTGACAAGCTGGCTGCGGAGAATCACTGTCTGAGGATCAAGATCTTAGGAGACTGT

TACTACTGCGTGTCAGGGCTGCCCGAGGCCCGGGCAGATCACGCCCACTGCTGTGTG

GAGATGGGGGTAGACATGATCGAAGCCATCTCGCTGGTGCGTGAGGTAACAGGTGTG

AACGTGAACATGCGTGTGGGCATCCACAGCGGACGTGTGCATTGCGGCGTCCTTGGC

CTACGGAAATGGCAGTTTGATGTCTGGTCAAACGATGTGACCCTGGCTAACCACATGG

AGGCCGGGGGCCGGGCCGGCCGCATCCACATCACTCGGGCTACACTGCAGTACTTG

AACGGGGACTATGAGGTGGAGCCAGGCCGTGGTGGTAACGCAATGCGTACCTCAAG

GAGCAGTGCATTGAGACCTTCCTCATACTTGGCGCCAGCCAAAAACGGAAAGAGGAG

AAAGCCATGCTGGCCAAGCTTCAGCGGACACGGGCCAACTCCATGGAAGGA
```

(encoding SEQ ID NO: 2)
SEQ ID NO: 7
```
TACAACCGGAGGTTGCTGCATAACATTCTTCCCAAGGACGTGGCCGCCCACTTCCTGG

CCCGGGAACGCCGCAACGATGAGCTGTACTACCAGTCGTGTGAATGTGTGGCTGTCA

TGTTTGCCTCCATCGCCAATTTCTCGGAGTTCTACGTGGAGCTCGAGGCAAACAACGA

GGGCGTGGAGTGCCTGCGGCTGCTCAATGAGATCATCGCAGACTTTGACGAGATCAT

CAGTGAGGAGAGATTCCGGCAGTTGGAGAAGATCAAGACCATCGGTAGCACCTACAT

GGCCGCCTCTGGGCTAAATGCCAGCACCTATGACCAGGTCGGCCGCTCACACATCAC

GGCGCTGGCTGACTATGCCATGCGGCTCATGGAGCAGATGAAACACATCAATGAACA

CTCTTTCAACAATTTCCAGATGAAGATCGGGTTGAACATGGGTCCGGTTGTAGCAGGC

GTCATTGGGGCCCGAAAGCCACAGTATGACATCTGGGGAAATACCGTGAATGTTTCCA

GTCGTATGGACAGCACTGGAGTTCCTGACCGAATACAGGTGACTACGGACCTATACCA
```

-continued
GGTTCTAGCTGCCAAGGGCTACCAGCTGGAGTGTCGAGGGGTGGTCAAGGTGAAGG

GAAAGGGGAGATGACCACCTAC

In alternative embodiments, to practice the methods and compositions (e.g., kits, products of manufacture) as provided herein, provided are isolated, synthetic and/or recombinant nucleic acids or genes encoding, e.g., a C1 and a C2 domain of an adenylyl cylase (AC) (optionally a human or a murine AC) and optionally lacking all or substantially most AC transmembrane domains. In alternative embodiments, to practice the methods as provided herein, the invention provides nucleic acids or genes in recombinant form in an (e.g., spliced into) an expression vehicle for in vivo expression, e.g., in a vector or a recombinant virus. In other alternative embodiments, provided are, e.g., isolated, synthetic and/or recombinant nucleic acids encoding inhibitory nucleic acids (e.g., siRNA, microRNA, antisense, ribozyme) that can inhibit the expression of genes or messages (mRNAs) that inhibit the expression of the desired gene or nucleic acid, e.g., encoding a C1 and a C2 domain of an adenylyl cylase (AC), and lacking all AC transmembrane domains.

In alternative embodiments, nucleic acids as provided herein are made, isolated and/or manipulated by, e.g., cloning and expression of cDNA libraries, amplification of message or genomic DNA by PCR, and the like. The nucleic acids and genes used to practice compositions and methods as provided herein, including DNA, RNA, iRNA, antisense nucleic acid, cDNA, genomic DNA, vectors, viruses or hybrids thereof, can be isolated from a variety of sources, genetically engineered, amplified, and/or expressed/generated recombinantly. Recombinant polypeptides (e.g., chimeric proteins used to practice compositions and methods as provided herein) generated from these nucleic acids can be individually isolated or cloned and tested for a desired activity. Any recombinant expression system or gene therapy delivery vehicle can be used, including e.g., viral (e.g., AAV constructs or hybrids) bacterial, fungal, mammalian, yeast, insect or plant cell expression systems or expression vehicles.

Alternatively, nucleic acids used to practice compositions and methods as provided herein can be synthesized in vitro by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066.

Techniques for the manipulation of nucleic acids used to practice compositions and methods as provided herein, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

Another useful means of obtaining and manipulating nucleic acids used to practice the methods as provided herein is to clone from genomic samples, and, if desired, screen and re-clone inserts isolated or amplified from, e.g., genomic clones or cDNA clones. Sources of nucleic acid used in the methods as provided herein include genomic or cDNA libraries contained in, e.g., mammalian artificial chromosomes (MACs), see, e.g., U.S. Pat. Nos. 5,721,118; 6,025,155; human artificial chromosomes, see, e.g., Rosenfeld (1997) Nat. Genet. 15:333-335; yeast artificial chromosomes (YAC); bacterial artificial chromosomes (BAC); P1 artificial chromosomes, see, e.g., Woon (1998) Genomics 50:306-316; P1-derived vectors (PACs), see, e.g., Kern (1997) Biotechniques 23:120-124; cosmids, recombinant viruses, phages or plasmids.

In alternative embodiments, to practice the methods as provided herein, chimeric or fusion proteins and nucleic acids encoding them are used. In alternative embodiments, the chimeric or fusion protein is fused to a heterologous peptide or polypeptide, such as a peptide for targeting the polypeptide to a desired cell type, such a cardiac myocytes, or a lung cell.

In alternative embodiments, a heterologous peptide or polypeptide joined or fused to a protein used to practice compositions and methods as provided herein can be an N-terminal identification peptide which imparts a desired characteristic, such as fluorescent detection, increased stability and/or simplified purification. Peptides and polypeptides used to practice compositions and methods as provided herein can also be synthesized and expressed as fusion proteins with one or more additional domains linked thereto for, e.g., producing a more immunogenic peptide, to more readily isolate a recombinantly synthesized peptide, to identify and isolate antibodies and antibody-expressing B cells, and the like. Detection and purification facilitating domains include, e.g., metal chelating peptides such as polyhistidine tracts and histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor Xa or enterokinase (Invitrogen, San Diego Calif.) between a purification domain and the motif-comprising peptide or polypeptide to facilitate purification. For example, an expression vector can include an epitope-encoding nucleic acid sequence linked to six histidine residues followed by a thioredoxin and an enterokinase cleavage site (see e.g., Williams (1995) Biochemistry 34:1787-1797; Dobeli (1998) Protein Expr. Purif. 12:404-414). The histidine residues facilitate detection and purification while the enterokinase cleavage site provides a means for purifying the epitope from the remainder of the fusion protein. Technology pertaining to vectors encoding fusion proteins and application of fusion proteins are well described in the scientific and patent literature, see e.g., Kroll (1993) DNA Cell. Biol., 12:441-53.

Nucleic acids or nucleic acid sequences used to practice compositions and methods as provided herein can be an oligonucleotide, nucleotide, polynucleotide, or to a fragment of any of these, to DNA or RNA of genomic or synthetic origin which may be single-stranded or double-stranded and may represent a sense or antisense strand, to peptide nucleic acid (PNA), or to any DNA-like or RNA-like material, natural or synthetic in origin. Compounds use to practice compositions and methods as provided herein include "nucleic acids" or "nucleic acid sequences" including oligonucleotide, nucleotide, polynucleotide, or any fragment of any of these; and include DNA or RNA (e.g., mRNA, rRNA, tRNA, iRNA) of genomic or synthetic origin which may be single-stranded or double-stranded; and can be a sense or antisense strand, or a peptide nucleic acid (PNA), or any DNA-like or RNA-like material, natural or synthetic in origin, including, e.g., iRNA, ribonucleoproteins (e.g., e.g., double stranded iRNAs, e.g., iRNPs). Compounds use to practice compositions and methods as provided herein include nucleic acids, i.e., oligonucleotides, containing known analogues of natural nucleotides. Compounds use to practice compositions and methods as provided herein include nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156. Compounds use to practice compositions and methods as provided herein include "oligonucleotides" including a single stranded polydeoxynucleotide or two complementary polydeoxynucleotide strands that may be chemically synthesized. Compounds use to practice compositions and methods as provided herein include synthetic oligonucleotides having no 5' phosphate, and thus will not ligate to another oligonucleotide without adding a phosphate with an ATP in the presence of a kinase. A synthetic oligonucleotide can ligate to a fragment that has not been dephosphorylated.

In alternative aspects, compounds used to practice compositions and methods as provided herein include genes or any segment of DNA involved in producing a chimeric or fusion polypeptide as provided herein; it can include regions preceding and following the coding region (leader and trailer) as well as, where applicable, intervening sequences (introns) between individual coding segments (exons). "Operably linked" can refer to a functional relationship between two or more nucleic acid (e.g., DNA) segments. In alternative aspects, it can refer to the functional relationship of transcriptional regulatory sequence to a transcribed sequence. For example, a promoter can be operably linked to a coding sequence, such as a nucleic acid used to practice compositions and methods as provided herein, if it stimulates or modulates the transcription of the coding sequence in an appropriate host cell or other expression system. In alternative aspects, promoter transcriptional regulatory sequences can be operably linked to a transcribed sequence where they can be physically contiguous to the transcribed sequence, i.e., they can be cis-acting. In alternative aspects, transcriptional regulatory sequences, such as enhancers, need not be physically contiguous or located in close proximity to the coding sequences whose transcription they enhance.

In alternative aspects, the invention comprises use of "expression cassettes" comprising a nucleotide sequences used to practice compositions and methods as provided herein, which can be capable of affecting expression of the nucleic acid, e.g., a structural gene or a transcript (e.g., encoding a C1 and a C2 domain of an adenylyl cylase (AC), and lacking all AC transmembrane domains) in a host compatible with such sequences. Expression cassettes can include at least a promoter operably linked with the polypeptide coding sequence or inhibitory sequence; and, in one aspect, with other sequences, e.g., transcription termination signals. Additional factors necessary or helpful in effecting expression may also be used, e.g., enhancers.

In alternative aspects, expression cassettes used to practice compositions and methods as provided herein also include plasmids, expression vectors, recombinant viruses, any form of recombinant "naked DNA" vector, and the like. In alternative aspects, a "vector" used to practice compositions and methods as provided herein can comprise a nucleic acid that can infect, transfect, transiently or permanently transduce a cell. In alternative aspects, a vector used to practice compositions and methods as provided herein can be a naked nucleic acid, or a nucleic acid complexed with protein or lipid. In alternative aspects, vectors used to practice compositions and methods as provided herein can comprise viral or bacterial nucleic acids and/or proteins, and/or membranes (e.g., a cell membrane, a viral lipid envelope, etc.). In alternative aspects, vectors used to practice compositions and methods as provided herein can include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and can include both the expression and non-expression plasmids. In alternative aspects, the vector used to practice compositions and methods as provided herein can be stably replicated by the cells during mitosis as an autonomous structure, or can be incorporated within the host's genome.

In alternative aspects, "promoters" used to practice compositions and methods as provided herein include all sequences capable of driving transcription of a coding sequence in a cell, e.g., a mammalian cell such as a heart, lung, muscle, nerve or brain cell. Thus, promoters used in the constructs as provided herein include cis-acting transcriptional control elements and regulatory sequences that are involved in regulating or modulating the timing and/or rate of transcription of a gene. For example, a promoter used to practice compositions and methods as provided herein can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) transcription.

In alternative embodiments, "constitutive" promoters used to practice compositions and methods as provided herein can be those that drive expression continuously under most environmental conditions and states of development or cell differentiation. In alternative embodiments, "Inducible" or "regulatable" promoters used to practice compositions and methods as provided herein can direct expression of the nucleic acid as provided herein under the influence of environmental conditions, administered chemical agents, or developmental conditions.

Gene Therapy and Gene Delivery Vehicles

In alternative embodiments, methods as provided herein comprise use of nucleic acid (e.g., nucleic acid encoding a C1 and a C2 domain of an adenylyl cylase (AC), and lacking all AC transmembrane domains) delivery systems to deliver a payload of a nucleic acids or genes, or a C1C2-expressing nucleic acid, transcript or message, to a cell or cells in vitro, ex vivo, or in vivo, e.g., as gene therapy delivery vehicles.

In alternative embodiments, expression vehicle, vector, recombinant virus, or equivalents used to practice methods as provided herein are or comprise: an adeno-associated virus (AAV), a lentiviral vector or an adenovirus vector; an AAV serotype AAV5, AAV6, AAV8 or AAV9; a rhesus-derived AAV, or the rhesus-derived AAV AAVrh.10hCLN2; an organ-tropic AAV, or a cardiotropic AAV, or a cardiotropic AAVM41 mutant; and/or an AAV capsid mutant or AAV hybrid serotype. In alternative embodiments, the AAV is engineered to increase efficiency in targeting a specific cell type that is non-permissive to a wild type (wt) AAV and/or to improve efficacy in infecting only a cell type of interest. In alternative embodiments, the hybrid AAV is retargeted or engineered as a hybrid serotype by one or more modifications comprising: 1) a transcapsidation, 2) adsorption of a bi-specific antibody to a capsid surface, 3) engineering a mosaic capsid, and/or 4) engineering a chimeric capsid. It is well known in the art how to engineer an adeno-associated virus (AAV) capsid in order to increase efficiency in targeting specific cell types that are non-permissive to wild type (wt) viruses and to improve efficacy in infecting only the cell type of interest; see e.g., Wu et al., Mol. Ther. 2006 September; 14(3):316-27. Epub 2006 Jul. 7; Choi, et al., Curr. Gene Ther. 2005 June; 5(3):299-310.

For example, the rhesus-derived AAV AAVrh.10hCLN2 or equivalents thereof can be used, wherein the rhesus-derived AAV may not be inhibited by any pre-existing immunity in a human; see e.g., Sondhi, et al., Hum Gene Ther. Methods. 2012 October; 23(5):324-35, Epub 2012 Nov. 6; Sondhi, et al., Hum Gene Ther. Methods. 2012 Oct. 17; teaching that direct administration of AAVrh.10hCLN2 to the CNS of rats and non-human primates at doses scalable to humans has an acceptable safety profile and mediates significant payload expression in the CNS.

Also, for example, AAV vectors specifically designed for cardiac gene transfer (a cardiotropic AAV) can be used, e.g., the AAVM41 mutant having improved transduction efficiency and specificity in the myocardium, see, e.g., Yang, et al. Virol J. 2013 Feb. 11; 10(1):50.

Because adeno-associated viruses (AAVs) are common infective agents of primates, and as such, healthy primates carry a large pool of AAV-specific neutralizing antibodies (NAbs) which inhibit AAV-mediated gene transfer therapeutic strategies, the methods as provided herein comprise screening of patient candidates for AAV-specific NAbs prior to treatment, especially with the frequently used AAV8 capsid component, to facilitate individualized treatment design and enhance therapeutic efficacy; see, e.g., Sun, et al., J. Immunol. Methods. 2013 Jan. 31; 387(1-2):114-20, Epub 2012 Oct. 11.

Kits and Instructions

Provided are kits comprising compositions and methods as provided herein, including instructions for use thereof. As such, kits, cells, expression vehicles (e.g., recombinant viruses, vectors) and the like can also be provided.

For example, in alternative embodiments, provided are kits comprising compositions used to practice compositions and methods as provided herein, e.g., comprising a C1 and a C2 domain of an adenylyl cylase (AC), and lacking all AC transmembrane domains, (b) a liquid or aqueous formulation as provided herein, or (c) the vesicle, liposome, nanoparticle or nanolipid particle as provided herein. In one aspect, the kit further comprising instructions for practicing any methods as provided herein, e.g., in vitro or ex vivo methods for enhancing calcium handling in a cardiac myocyte.

Formulations

In alternative embodiments, provided are compositions and methods for use in treating heart failure in vivo. In alternative embodiments, these compositions comprise nucleic acids formulated for these purposes, e.g., expression vehicles or nucleic acids formulated in a buffer, in a saline solution, in a powder, an emulsion, in a vesicle, in a liposome, in a nanoparticle, in a nanolipoparticle and the like.

In alternative embodiments, provided are methods comprising administration of nucleic acids encoding a C1 and a C2 domain of an adenylyl cylase (AC), and lacking all AC transmembrane domains, to treat, ameliorate or prevent a heart failure. Accordingly, provided are the appropriate formulations and dosages of peptides or polypeptides as provided herein, or C1C2-encoding nucleic acids, for same.

In alternative embodiments, the compositions (including formulations of nucleic acids encoding a C1 and a C2 domain of an adenylyl cylase (AC)) can be formulated in any way and can be applied in a variety of concentrations and forms depending on the desired in vitro, in vivo or ex vivo conditions, including a desired in vivo or ex vivo method of administration and the like. Details on techniques for in vitro, in vivo or ex vivo formulations and administrations are well described in the scientific and patent literature.

Formulations and/or carriers used to practice compositions and methods as provided herein are well known in the art. Formulations and/or carriers used to practice compositions and methods as provided herein can be in forms such as tablets, pills, powders, capsules, liquids, gels, syrups, slurries, suspensions, etc., suitable for in vivo or ex vivo applications.

In alternative embodiments, peptides or polypeptides, or nucleic acids, used to practice compositions and methods as provided herein can be in admixture with an aqueous and/or buffer solution or as an aqueous and/or buffered suspension, e.g., including a suspending agent, such as sodium carboxymethylcellulose, methylcellulose, hydroxypropylmethylcellulose, sodium alginate, polyvinyl-pyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate. Formulations can be adjusted for osmolarity, e.g., by use of an appropriate buffer.

In practicing compositions and methods as provided herein, the compounds (e.g., formulations) as provided herein (e.g., nucleic acids encoding a C1 and a C2 domain of an adenylyl cylase (AC), comprise a solution dissolved in a pharmaceutically acceptable carrier, e.g., acceptable vehicles and solvents that can be employed include water and Ringer's solution, an isotonic sodium chloride. In addition, sterile fixed oils can be employed as a solvent or suspending medium. For this purpose any fixed oil can be employed including synthetic mono- or diglycerides, or fatty acids such as oleic acid. In one embodiment, solutions and formulations used to practice the invention are sterile and can be manufactured to be generally free of undesirable matter. In one embodiment, these solutions and formulations are sterilized by conventional, well known sterilization techniques.

The solutions and formulations used to practice the invention can comprise auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of active agent (e.g., C1C2-encoding nucleic acids or genes) in these formulations can vary widely, and can be selected primarily based on fluid volumes, viscosities and the like, in accordance with the particular mode of in vivo or ex vivo administration selected and the desired results, e.g., increasing in vivo C1C2 expression.

The solutions and formulations used to practice the invention can be lyophilized; for example, provided are a stable lyophilized formulation comprising C1C2-encoding nucleic acids or genes, or C1C2 peptides or polypeptides. In one aspect, this formulation is made by lyophilizing a solution comprising a C1C2-encoding nucleic acid or gene, or C1C2 peptides or polypeptides, and a bulking agent, e.g., mannitol, trehalose, raffinose, and sucrose or mixtures thereof. A process for preparing a stable lyophilized formulation can include lyophilizing a solution about 2.5 mg/mL protein, about 15 mg/mL sucrose, about 19 mg/mL NaCl, and a sodium citrate buffer having a pH greater than 5.5 but less than 6.5. See, e.g., U.S. patent app. no. 20040028670.

The compositions and formulations as provided herein can be delivered by the use of liposomes (see also discussion, below). By using liposomes, particularly where the liposome surface carries ligands specific for target cells, or are otherwise preferentially directed to a specific tissue or organ type, one can focus the delivery of the active agent into a target cells in an in vivo or ex vivo application.

Nanoparticles, Nanolipoparticles and Liposomes

The invention also provides nanoparticles, nanolipoparticles, vesicles and liposomal membranes comprising compounds used to practice the methods of compositions and methods as provided herein, e.g., to deliver a nucleic acid encoding a C1 and a C2 domain of an adenylyl cylase (AC), and lacking all AC transmembrane domains, to an individual, a patient or mammalian cells in vivo or ex vivo. In alternative embodiments, these compositions are designed to target specific molecules, including biologic molecules, such as polypeptides, including cell surface polypeptides, e.g., for targeting a desired cell type, e.g., a mammalian cardiac cell, a kidney cell, a lung cell, a nerve cell and the like.

Provided are multilayered liposomes comprising compounds used to practice compositions and methods as provided herein, e.g., as described in Park, et al., U.S. Pat. Pub. No. 20070082042. The multilayered liposomes can be prepared using a mixture of oil-phase components comprising squalane, sterols, ceramides, neutral lipids or oils, fatty acids and lecithins, to about 200 to 5000 nm in particle size, e.g., to entrap a C1C2-encoding nucleic acid or gene.

Liposomes can be made using any method, e.g., as described in Park, et al., U.S. Pat. Pub. No. 20070042031, including method of producing a liposome by encapsulating an active agent (e.g., C1C2-encoding nucleic acids or genes, or C1C2 peptides or polypeptides), the method comprising providing an aqueous solution in a first reservoir; providing an organic lipid solution in a second reservoir, and then mixing the aqueous solution with the organic lipid solution in a first mixing region to produce a liposome solution, where the organic lipid solution mixes with the aqueous solution to substantially instantaneously produce a liposome encapsulating the active agent; and immediately then mixing the liposome solution with a buffer solution to produce a diluted liposome solution.

In one embodiment, liposome compositions used to practice compositions and methods as provided herein comprise a substituted ammonium and/or polyanions, e.g., for targeting delivery of a compound (e.g., C1C2-encoding nucleic acids or genes) used to practice compositions and methods as provided herein to a desired cell type, as described e.g., in U.S. Pat. Pub. No. 20070110798.

The invention also provides nanoparticles comprising compounds used to practice compositions and methods as provided herein in the form of active agent-containing nanoparticles (e.g., a secondary nanoparticle), as described, e.g., in U.S. Pat. Pub. No. 20070077286. In one embodiment, provided are nanoparticles comprising a fat-soluble active agent of compositions and methods as provided herein or a fat-solubilized water-soluble active agent to act with a bivalent or trivalent metal salt.

In one embodiment, solid lipid suspensions can be used to formulate and to deliver C1C2-encoding nucleic acids or genes, or C1C2 peptides or polypeptides, used to practice the invention to a patient, an individual, or mammalian cell in vivo or ex vivo, as described, e.g., in U.S. Pat. Pub. No. 20050136121.

Delivery Vehicles

In alternative embodiments, any delivery vehicle can be used to practice the methods or compositions of compositions and methods as provided herein, e.g., to deliver C1C2 peptides or polypeptides, or to practice the methods as provided herein in vivo or ex vivo. For example, delivery vehicles comprising polycations, cationic polymers and/or cationic peptides, such as polyethyleneimine derivatives, can be used e.g. as described, e.g., in U.S. Pat. Pub. No. 20060083737.

In one embodiment, a dried polypeptide-surfactant complex is used to formulate a composition as provided herein, wherein a surfactant is associated with a nucleic acid via a non-covalent bond e.g. as described, e.g., in U.S. Pat. Pub. No. 20040151766.

In one embodiment, a nucleic acid or polypeptide used to practice compositions and methods as provided herein can be applied to cells as polymeric hydrogels or water-soluble copolymers, e.g., as described in U.S. Pat. No. 7,413,739; for example, a nucleic acid or protein can be polymerized through a reaction between a strong nucleophile and a conjugated unsaturated bond or a conjugated unsaturated group, by nucleophilic addition, wherein each precursor component comprises at least two strong nucleophiles or at least two conjugated unsaturated bonds or conjugated unsaturated groups.

In one embodiment, a nucleic acid or protein is applied to cells using vehicles with cell membrane-permeant peptide conjugates, e.g., as described in U.S. Pat. Nos. 7,306,783; 6,589,503. In one aspect, the nucleic acid itself is conjugated to a cell membrane-permeant peptide. In one embodiment, a nucleic acid, protein, and/or the delivery vehicle are conjugated to a transport-mediating peptide, e.g., as described in U.S. Pat. No. 5,846,743, describing transport-mediating peptides that are highly basic and bind to poly-phosphoinositides.

In one embodiment, electro-permeabilization is used as a primary or adjunctive means to deliver C1C2-encoding nucleic acids or genes to a cell, e.g., using any electroporation system as described e.g. in U.S. Pat. Nos. 7,109,034; 6,261,815; 5,874,268.

Products of Manufacture, Implants and Artificial Organs

The invention also provides products of manufacture comprising cells as provided herein (e.g., cells modified to express a C1 and a C2 domain of an adenylyl cylase (AC), and lacking all AC transmembrane domains, to practice the methods as provided herein), and use of cells made by methods of compositions and methods as provided herein, including for example implants and artificial organs, bioreactor systems, cell culture systems, plates, dishes, tubes, bottles and flasks comprising cells modified to express C1C2 proteins to practice the methods as provided herein. Any implant, artificial organ, bioreactor systems, cell culture system, cell culture plate, dish (e.g., petri dish), cell culture tube and/or cell culture flask (e.g., a roller bottle) can be used to practice compositions and methods as provided herein.

In alternative embodiments provided are a bioreactor, implant, stent, artificial organ or similar device comprising cells modified to express C1C2 proteins to practice the methods as provided herein; for example, including implants as described in U.S. Pat. Nos. 7,388,042; 7,381,418; 7,379,765; 7,361,332; 7,351,423; 6,886,568; 5,270,192; and U.S. Pat. App. Pub. Nos. 20040127987; 20080119909 (describing auricular implants); 20080118549 (describing ocular implants); 20080020015 (describing a bioactive wound dressing); 20070254005 (describing heart valve bio-prostheses, vascular grafts, meniscus implants); 20070059335; 20060128015 (describing liver implants).

Implanting Cells In Vivo

In alternative embodiments, the methods as provided herein also comprise implanting or engrafting cells, e.g., cardiac, lung or kidney cells, comprising or expressing a C1 and a C2 domain of an adenylyl cylase (AC), and lacking all AC transmembrane domains, used to practice the invention; and in one aspect, methods as provided herein comprise implanting or engrafting the nucleic acids or genes (or cells expressing them) encoding or expressing a C1 and a C2 domain of an adenylyl cylase (AC), and lacking all AC transmembrane domains, in a vessel, tissue or organ ex vivo or in vivo, or implanting or engrafting the re-programmed differentiated cell in an individual in need thereof.

Cells can be removed from an individual, treated using the compositions and/or methods of compositions and methods as provided herein, and reinserted (e.g., injected or engrafted) into a tissue, organ or into the individual, using any known technique or protocol. For example, de-differentiated re-programmed cells, or re-programmed differentiated cells, can be re-implanted (e.g., injected or engrafted) using microspheres e.g., as described in U.S. Pat. No. 7,442,389; e.g., in one aspect, the cell carrier comprises a bulking agent comprising round and smooth polymethyl-methacrylate microparticles preloaded within a mixing and delivery system and an autologous carrier comprising these cells. In another embodiment, the cells are re-administered to a tissue, an organ and/or an individual in need thereof in a biocompatible crosslinked matrix, as described e.g., in U.S. Pat. App. Pub. No. 20050027070.

In another embodiment, the cells as provided herein (e.g., cells made by practicing the methods of compositions and methods as provided herein) are re-administered (e.g., injected or engrafted) to a tissue, an organ and/or an individual in need thereof within, or protected by, a biocompatible, nonimmunogenic coating, e.g., as on the surface of a synthetic implant, e.g., as described in U.S. Pat. No. 6,969,400, describing e.g., a protocol where a cAMP-incompetent AC can be conjugated to a polyethylene glycol that has been modified to contain multiple nucleophilic groups, such as primary amino or thiol group.

In one embodiment, the cells as provided herein (e.g., cells made by practicing the methods of compositions and methods as provided herein) are re-administered (e.g., injected or engrafted) to a tissue, an organ and/or an individual in need thereof using grafting methods as described e.g. by U.S. Pat. Nos. 7,442,390; 5,733,542.

Any method for delivering polypeptides, nucleic acids and/or cells to a tissue or organ (e.g., a lung, kidney, heart) can be used, and these protocols are well known in the art, e.g., as described in U.S. Pat. No. 7,514,401, describing e.g., using intracoronary (IC), intravenous (IV), and/or local delivery (myocardial injection) of polypeptides, nucleic acids and/or cells to a heart in situ. For example, in alternative embodiments, aerosol drug particles into the lungs and into the bloodstream, gene therapy, continuous infusions, repeated injections and/or sustained release polymers can be used for delivering polypeptides, nucleic acids and/or cells to a tissue or organ (e.g., a lung, kidney, heart). In alternative embodiments, nucleic acids and/or cells can be given through a catheter into the coronary arteries or by direct injection into the left atrium or ventricular myocardium via a limited thoracotomy; or delivered into the myocardium via a catheter passed during cardiac catheterization; or delivered into the pericardial space.

In alternative embodiments, nucleic acids or proteins used to practice compositions and methods as provided herein, or a vector comprising a nucleic acid used to practice the invention (e.g., an AAV, or adenoviral gene therapy vector), or vesicle, liposome, nanoparticle or nanolipid particle (NLP) as provided herein, and the like, to a tissue or organ (e.g., a lung, kidney, heart); e.g. as described in U.S. Pat. No. 7,501,486, e.g., polypeptides as provided herein comprising an amino acid sequence CRPPR (SEQ ID NO:1), the amino acid sequence CARPAR (SEQ ID NO:2) or a peptidomimetic thereof, or amino acid sequence CPKRPR (SEQ ID NO:3) or a peptidomimetic thereof.

Compositions used to practice compositions and methods as provided herein can be used in combination with other therapeutic agents, e.g. angiogenic agents, anti-thrombotic agents, anti-inflammatory agents, immunosuppressive agents, anti-arrhythmic agents, tumor necrosis factor inhibitors, endothelin inhibitors, angiotensin-converting enzyme inhibitors, calcium antagonists, antibiotic agents, antiviral agents and viral vectors.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (1989) Molecular Cloning: A Laboratory Manual, Second Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

Example 1: Exemplary Compositions and Methods for Treating Heart Failure

This example demonstrates that methods and compositions as provided herein including C1C2 gene transfer has beneficial effects on the failing human heart, and is effective regardless of ejection fraction (preserved or reduced), and can be used to treat individuals with heart failure.

Methods

GENERATION OF C1C2 FUSION PROTEIN. C1C2 peptide was generated by ligating the cytoplasmic domain 1 (C1, amino acids 349-576) with cytoplasmic domain 2 (C2, amino acids 939-1157) of mouse adenylyl cyclase type 6 (AC6) using a linker (12 amino acids: AAAGGIPPAAAM) (SEQ ID NO:8) as illustrated in FIG. 1A. The C-terminus of C1C2 was linked with an AU1 epitope tag (DTYRYI) (SEQ ID NO:9) to facilitate detection.

GENERATION OF C1C2 TRANSGENIC MICE. Animals were used in accordance with Association for Assessment and Accreditation of Laboratory Animal Care guidelines and approved by the Institutional Animal Care and Use Committee of VA San Diego Healthcare System. To generate mice with cardiac-directed expression of C1C2, the murine C1C2 cDNA with an AU1 tag at the C terminus was subcloned between the a-myosin heavy chain promoter and SV40 poly(A). A 7.1-kb fragment containing the expression cassette was used for pronuclear injection, carried out in the transgenic mouse facility at University of California, San Diego (inbred C57BL/6). Founder mice were identified by polymerase chain reaction (PCR) of genomic DNA prepared from tail tips. The C1C2 gene was detected using a primer homologous to the α-MHC promoter (forward: 5'-CACAT-AGAAGCCTAGCCCA CACC-3') (SEQ ID NO:10) and another primer in the C1 region (5'-GTTAGCCAGGGTCA CATCGT-3') (SEQ ID NO:11). C1C2 mRNA was detected in reverse transcription quantitative PCR, using the forward primer 5'-TGGGCCTCTCTACTCTGCAT-3' (SEQ ID NO:12) and the reverse primer 5'-TGGATGTAACC-TCGGG TCTC-3' (SEQ ID NO:13), enabling quantification of fold increase of C1C2 mRNA relative to that of endogenous AC6 mRNA.

Founder animals were crossbred with normal mice of the same strain, and selected animals were used for analysis of cardiac transgene expression. We documented variable transgene mRNA expression but similar levels of C1C2 protein expression in 2 lines and used the line with a 23-fold increase in C1C2 mRNA expression (vs. endogenous AC6) in this study. C1C2 protein was detected using anti-AU1 antibody, which has a low background in LV homogenates from transgene negative mice. C1C2 protein was 13-fold increased relative to that of the AU1 signal in transgene negative mice. The study included 114 mice (68 male, 46 female), 4.4±0.1 months of age, weighing 23.9±0.6 g.

ECHOCARDIOGRAPHY. Echocardiography was performed prior to isoproterenol (Iso) infusion and on day 6 or 7 of sustained Iso infusion, using methods previously described (15). Anesthesia was induced with 5% isoflurane (at a flow rate of 1 L/min oxygen) and maintained with 1% isoflurane in oxygen.

LV SYSTOLIC AND DIASTOLIC FUNCTION. Mice were anesthetized by intraperitoneal injection of sodium pentobarbital (80 mg/kg), and a 1.4-F micromanometer catheter (Millar Instruments, Houston, Tex.) was advanced via the right carotid artery across the aortic valve and into the LV cavity. Left ventricular pressure was recorded and stored digitally for processing (IOX1.8; Emka Technologies, Christchurch, Va.) as previously reported (11). Data were acquired and analyzed without knowledge of group identity. Subsequently, tissue samples were obtained.

CARDIAC MYOCYTE ISOLATION. Cardiac myocytes were isolated as previously described (15,16).

$Ca^{2+}$ TRANSIENTS. Cytosolic $Ca^{2+}$ transients (Indo-1) were measured from cardiac myocytes isolated from transgenic mice as previously described (13,17).

CYCLIC AMP MEASUREMENT AND PKA ACTIVITY ASSAY. Isolated cardiac myocytes were stimulated with Iso (10 mM, 10 min) or the water-soluble forskolin analog NKH477 (10 mM, 10 min) Cyclic AMP was measured using the cAMP Biotrak EIA™ (GE Healthcare, Chalfont, United Kingdom) as previously reported (15). PKA activity was determined as previously described (17).

IMMUNOFLUORESCENCE. Isolated cardiac myocytes were attached to laminin-coated 2-well chamber slides for 1 h, washed, fixed (10% formalin, 15 min, 23° C.), blocked with normal goat serum (1 h), and incubated (4° C., overnight) with the following antibodies: anti-AU1 antibody (1:300 dilution; for detecting C1C2 transgene protein; Fitzgerald, Atlanta, Ga.) and anti-Cav3 antibody (1:100 dilution, for detecting caveolae; BD Pharmingen, San Jose, Calif.). Cardiac myocytes were washed with phosphate-buffered saline and then incubated with secondary antibodies (Alexa Fluor 488 or 594 conjugated; 1:1,000 dilution) for 1 h. To identify the nucleus, cells were incubated with Hoechst dye (1:1,000 dilution, 20 min) Then, cardiac myocytes were imaged as previously described (18).

ISOPROTERENOL INFUSION. Osmotic minipumps (Alzet; DuRECT Corp., Cupertino, Calif.) were filled with Iso or saline. The 7-day continuous infusion delivered 60 mg/d/kg as previously described (19). RT-PCR. Primers for detecting phosphatidylinositol-3,4,5-trisphosphate-dependent Rac exchange factor 2 (P-Rex2) included forward primer 5'-ATCATGTGCAGCAGTGGTGT-3' (SEQ ID NO:14) and reverse primer 5-CCTTGGAGCTGACT-GAGG AG-3' (SEQ ID NO:15). The absence of suitable AC type-specific antibodies precluded quantitative assessment of LV AC isoform protein content. Instead, we used quantitative real-time RT-PCR to determine whether cardiac-directed C1C2 expression altered the cardiac expression of other AC isoforms (AC3, AC4, AC5, AC6, AC7, AC8, and AC9). Details of PCR conditions and primer sequences can be found in our previous studies (20).

MICROARRAY, ANTIBODIES. Expression of adenylyl cyclase-related proteins were analyzed using the Agilent gene expression microarray technique (PhalanxBio Inc., San Diego, Calif.). C1C2 protein was detected by anti-AU1 antibody (1:2,000 dilution: Fitzgerald) or anti-AC5/6 antibody (1:200 dilution; Santa Cruz Biotechnology, Dallas, Tex.). Additional antibodies included GAPDH (1:20,000 dilution; Fitzgerald); cMLCK (1:1,000 dilution; Abgent, San Diego, Calif.); MLC2v (1:1,000 dilution; Synaptic Systems, Gottingen, Germany), PKA catalytic subunit (1:1,000 dilution; BD Transduction, San Jose, Calif.); p-ERK1/2, p38, p-PKARII a and b (1:200 dilution; Santa Cruz Biotechnology); PLB (1:5,000 dilution; Affinity Bioreagents, Rockford, Ill.); phospho-16-PLB (1:3,000 dilution; Badrilla, Leeds, United Kingdom); S100A1 (1:1,000 dilution; Acris); SERCA2a antibody (1:1,000 dilution; Enzo, Exeter, United Kingdom); phospho-aB-crystallin (CryAB) and total CryAB antibodies (1:1,000 dilution; Enzo); P-308-Akt, P-473-Akt, T-Akt, p-GSK3a/b, p-MDM2, P-p70S6K, p70S6K, and phospho-S22/23 troponin I (TnI) (1:1,000 dilution each; Cell Signaling, Danvers, Mass.); vinculin (1:100,1000 dilution; Sigma, Darmstadt, Germany).

NECROPSY. Body, liver, lung, and LV weight (including interventricular septum) were recorded and a short axis midwall LV ring was fixed in formalin and embedded in paraffin. The remaining LV was quickly frozen in liquid nitrogen and stored at −80° C.

HISTOLOGY. Transmural sections of the LV were formalin-fixed and paraffin-embedded. Sections (5 mm) were mounted and counterstained with hematoxylin and eosin and with Masson's trichrome. For quantitative assessment of LV fibrosis, images of a short-axis midwall LV ring stained with Picro Sirius red stain were obtained by using a NanoZoomer™ digital slide scanner (Hamamatsu, Hamamatsu, Japan). Blinded analysis of the degree of fibrosis was conducted using ImageJ software (U.S. National Institutes of Health, Bethesda, Md.).

STATISTICAL ANALYSIS. Data are mean±SE. Between-group comparisons were made using Stu-dent t-test (unpaired, 2-tailed). Interactions of C1C2 expression and Iso infusion on outcomes were tested for statistical significance using 2-way ANOVA followed by Bonferroni t-test. The null hypothesis was rejected when $p<0.05$.

Results

Figure 1B:
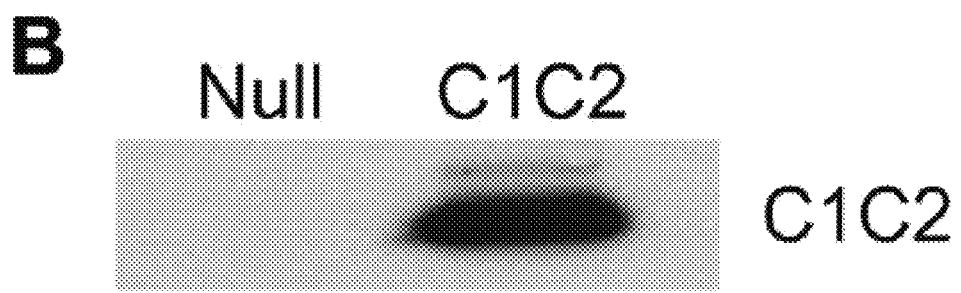
Figure 1C:
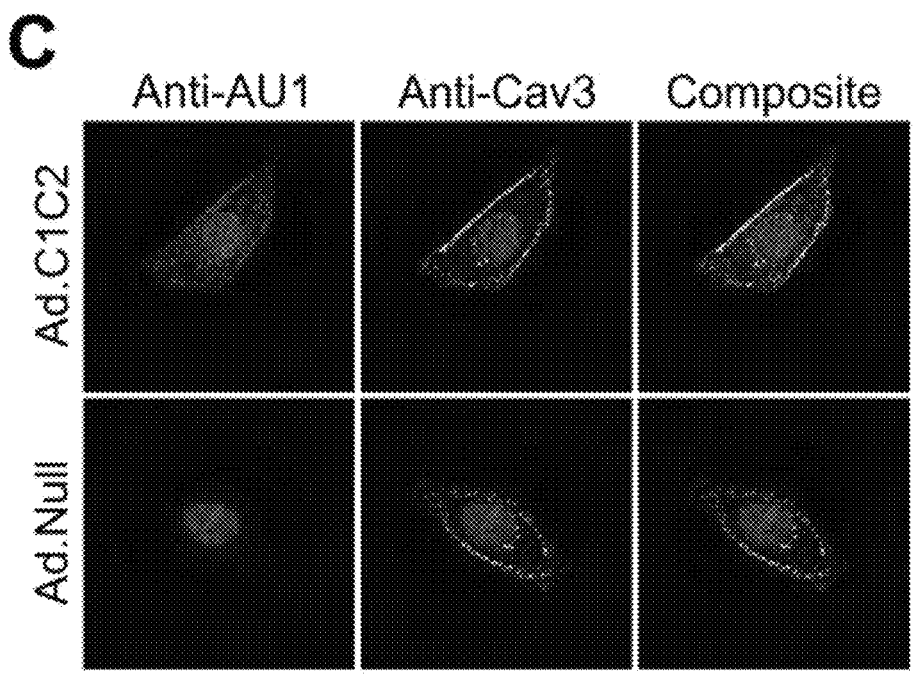
Figure 1D:
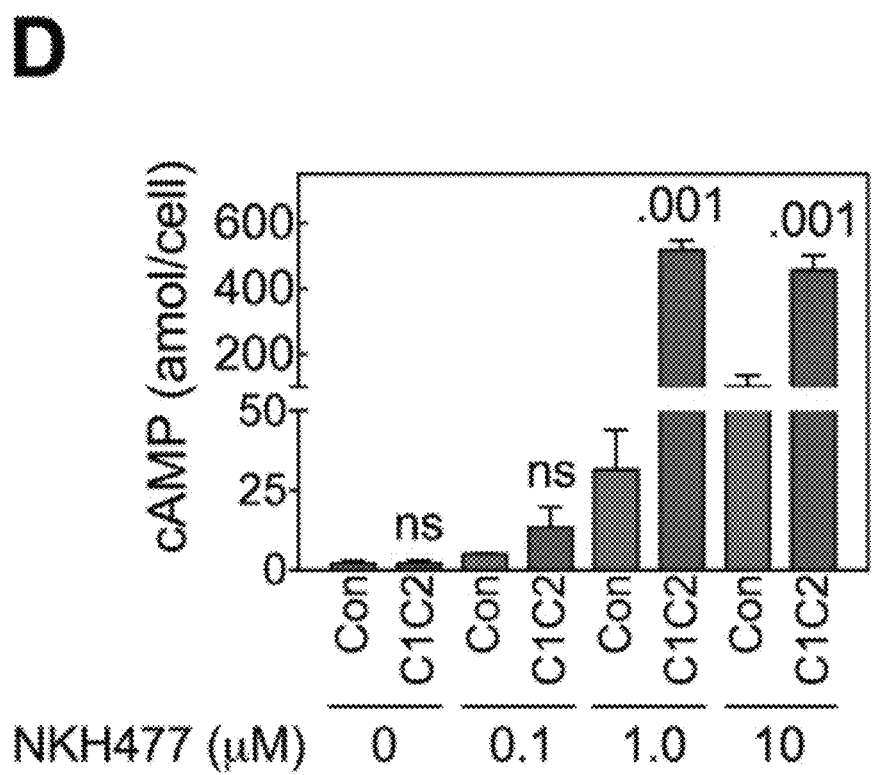
Figure 1E:
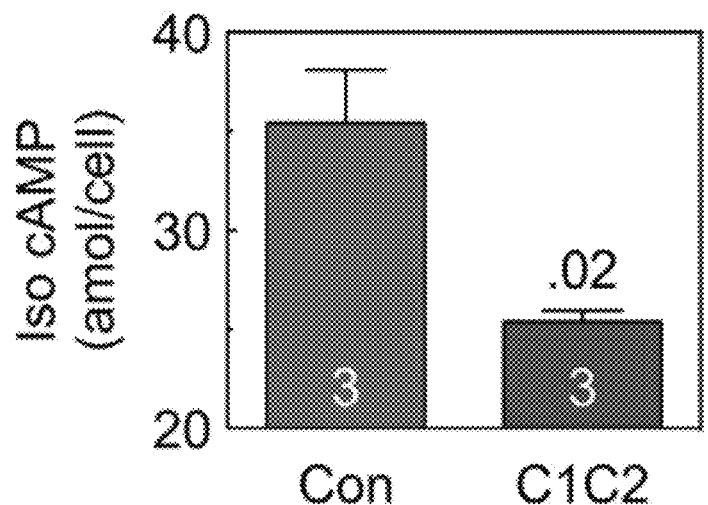
Figure 2B:
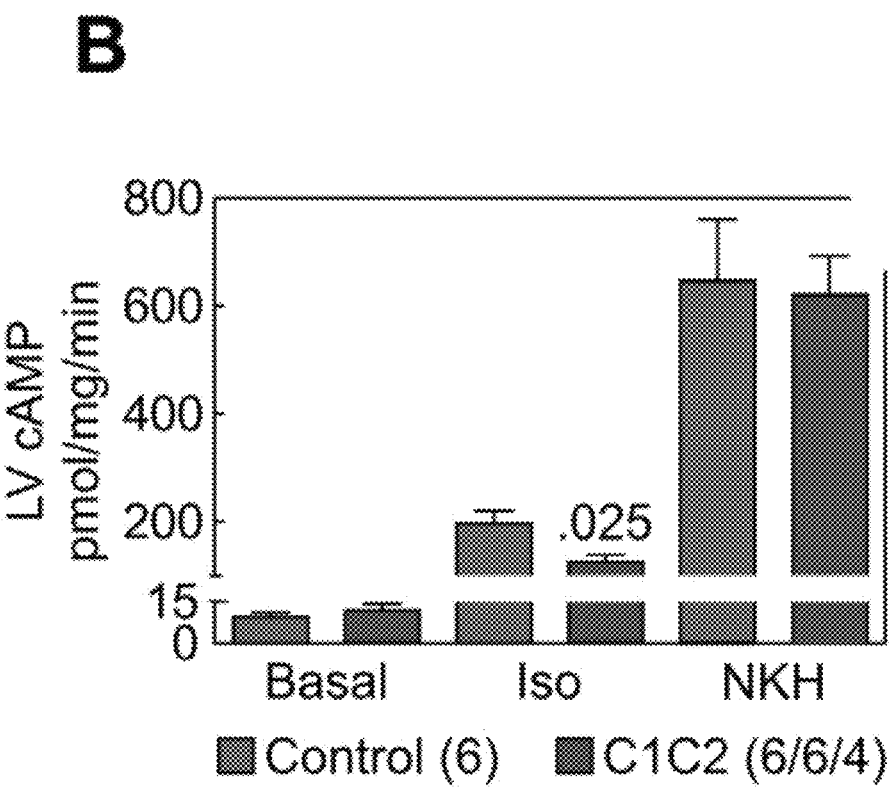
Figure 2C:
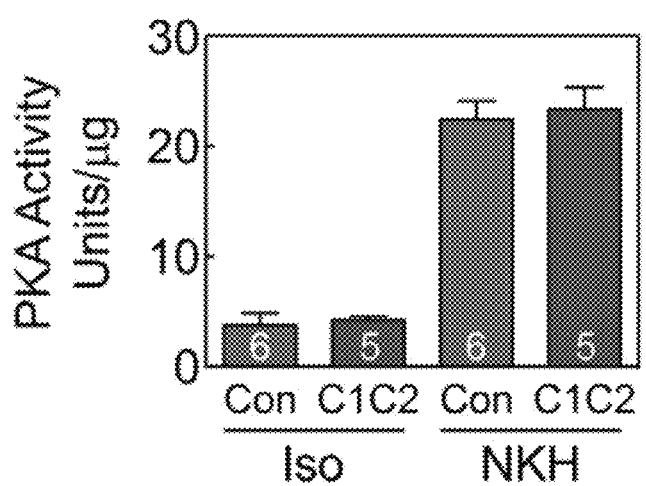

C1C2 GENE TRANSFER IN CARDIAC MYOCYTES. Location and AC activity. Anti-AU1 antibody was used to detect C1C2 expression in neonatal rat cardiac myocytes after Ad5.C1C2 infection (200 vp/cell) (FIG. 1B). Intracellular C1C2 transgene protein was detected in the cytosol and plasma membrane/caveolae (FIG. 1C) and exhibited dose-dependent augmentation in AC activity when stimulated with the water soluble forskolin analog NKH477 (FIG. 1D). Ad5-mediated C1C2 expression in neonatal rat cardiac myocytes reduced net Iso-stimulated cAMP generation (FIG. 1E), which was also seen in LV samples from control and C1C2 mice (FIG. 2B). In contrast, we did not see increased NKH477-stimulated cAMP in LV homogenates from C1C2 TG mice (FIG. 2B) as we saw after C1C2 gene transfer (FIG. 1D), which may reflect differences in amounts of C1C2 expressed (Ad5-mediated vs. transgenic line), species (rat vs. mice), or age (neonatal vs. adult cardiac myocytes). Although we saw reduced Iso-stimulated cAMP generation in cardiac myocytes from C1C2 mice compared to control (FIG. 2B), this decrement was not sufficient to reduce PKA activity (FIG. 2C).

Figure 1F:
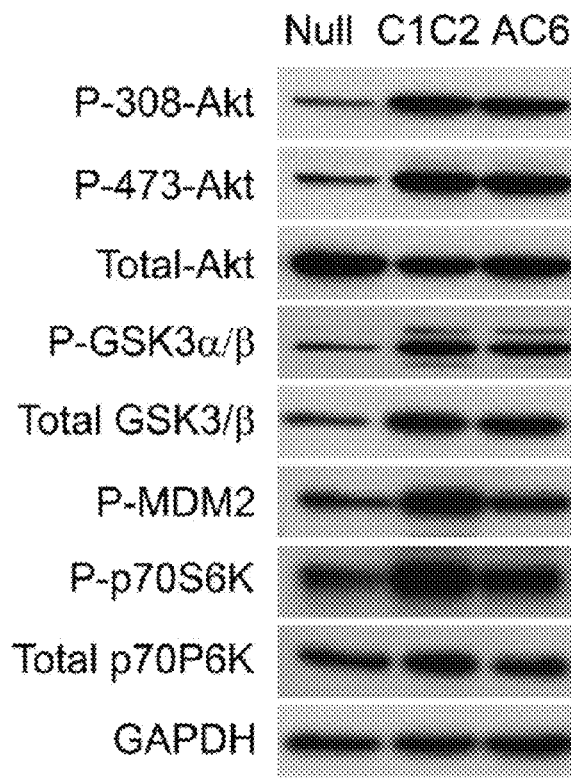

Akt Signaling. Adenovirus-mediated gene transfer of C1C2 or AC6 into cultured cardiac myocytes was performed to compare signaling events evoked by C1C2 versus AC6. Both C1C2 and AC6 expression activated PI3K/Akt signaling pathways, increased phosphorylation of Akt at Ser308 and Thr473, and increased phosphorylation of the downstream Akt target proteins GASK3a/b, murine double mutant 2 (MDM2), and p70S6K (FIG. 1F). Finally, C1C2 expression was associated with increased phosphorylation of ERK1/2, p38, and CryAB (aB-crystallin) at both S45 and S59 sites (FIG. 1G, upper). C1C2 protein was immunoprecipitated by anti-CryAB antibody and CryAB protein was immune-precipitated by anti-AC5/6 antibody (for pulldown and detecting C1C2) (FIG. 1G, lower), indicating that C1C2 interacts with CryAB in cardiac myocytes.

C1C2 TRANSGENIC LINES. Cardiac-directed expression of C1C2 increased LV C1C2 mRNA: one line 14-fold greater than endogenous AC6 mRNA, a second line 23-fold greater (FIG. 2A, lower). However, LV C1C2 protein, detected by AU1 antibody, was increased similar amounts in both lines (FIG. 2A, upper).

LV SYSTOLIC AND DIASTOLIC FUNCTION. Echocardiography. C1C2 mice had normal LV dimensions and fractional shortening prior to 7 days of Iso infusion (Table 1, No Iso). Fractional shortening was reduced after 7 days of Iso infusion with no between-group difference (Table 1, 7 days of Iso).

Figure 2D:
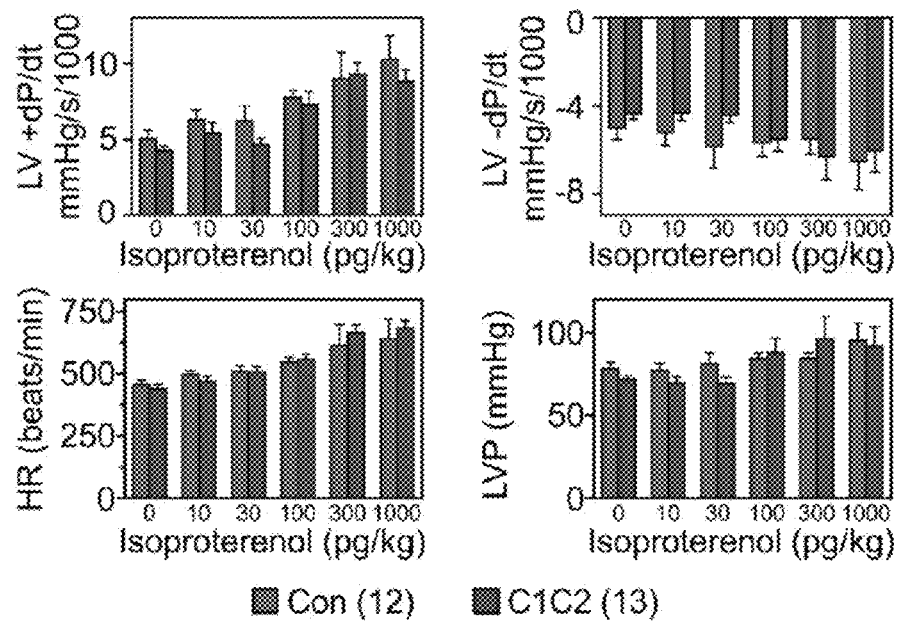

LV function prior to sustained isoproterenol infusion. In vivo assessment of rates of LV pressure development (+dP/dt) and decline (−dP/dt) showed no group differences in peak +dP/dt (control [Con] mice: 5,070±553 mm Hg/s, n = 12; C1C2 mice: 4,319±253 mm Hg/s, n = 13; p = 0.22) or in peak −dP/dt (Con: −5,003±527 mm Hg/s, n = 12; C1C2 mice: −4,362±248 mm Hg/s, n = 13; p = 0.27) (Table 2). In addition, there were no differences in LV peak +dP/dt, LV peak −dP/dt, LV developed pressure or heart rate through a wide range of brief graded doses of infused Iso (FIG. 2D). No baseline between-group differences were seen in LV developed pressure or heart rate (Table 2, No Iso).

LV function after 7 days of continuous isoproterenol infusion. The response to sustained Iso infusion was critically influenced by the presence of C1C2 for LV peak +dP/dt (p = 0.012), LV peak −dP/dt (p<0.001), and LV developed pressure (p<0.001), with no such interaction with heart rate (Table 2). In Con mice, 7 days of continuous Iso infusion tended to reduce LV peak +dP/dt (23% reduction; p = 0.24) and LV peak −dP/dt (30% reduction; p = 0.06) (FIGS. 3A and 3B, Table 2).

Figure 3A:
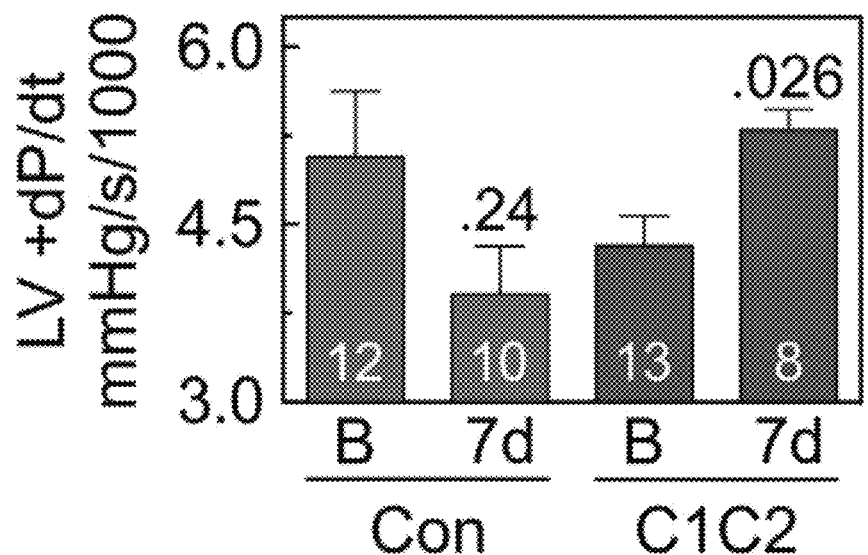
FIG. 3A-E.
Figure 3B:
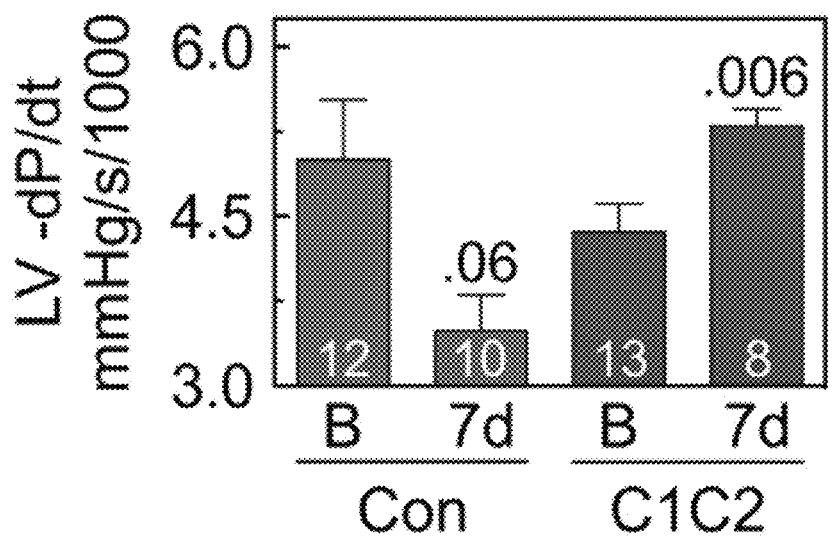
Figure 3C:
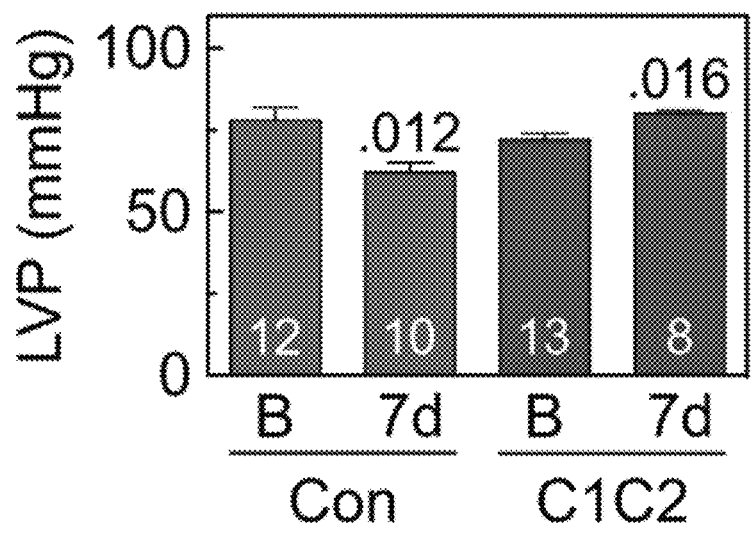
Figure 3D:
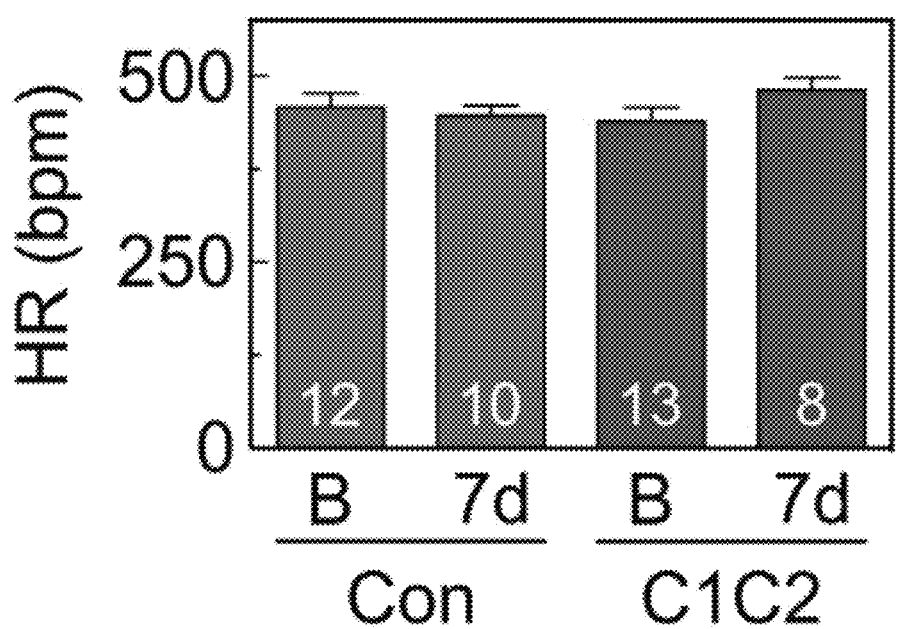

In contrast, continuous Iso infusion showed a directionally opposite effect on LV function in mice with cardiac-directed C1C2 expression, with increases in both LV peak +dP/dt (23% increase, p = 0.026) and LV peak −dP/dt (27% increase; p = 0.006) (FIGS. 3A and 3B, Table 2). In addition, Con mice showed reduced (p = 0.012) but C1C2 mice showed increased LV developed pressure (p = 0.016) (FIG. 3C) at similar heart rates (FIG. 3D).

NECROPSY. Table 3 shows that sustained Iso infusion was associated with similar increases in LV and liver weight in both groups.

Figure 2E:
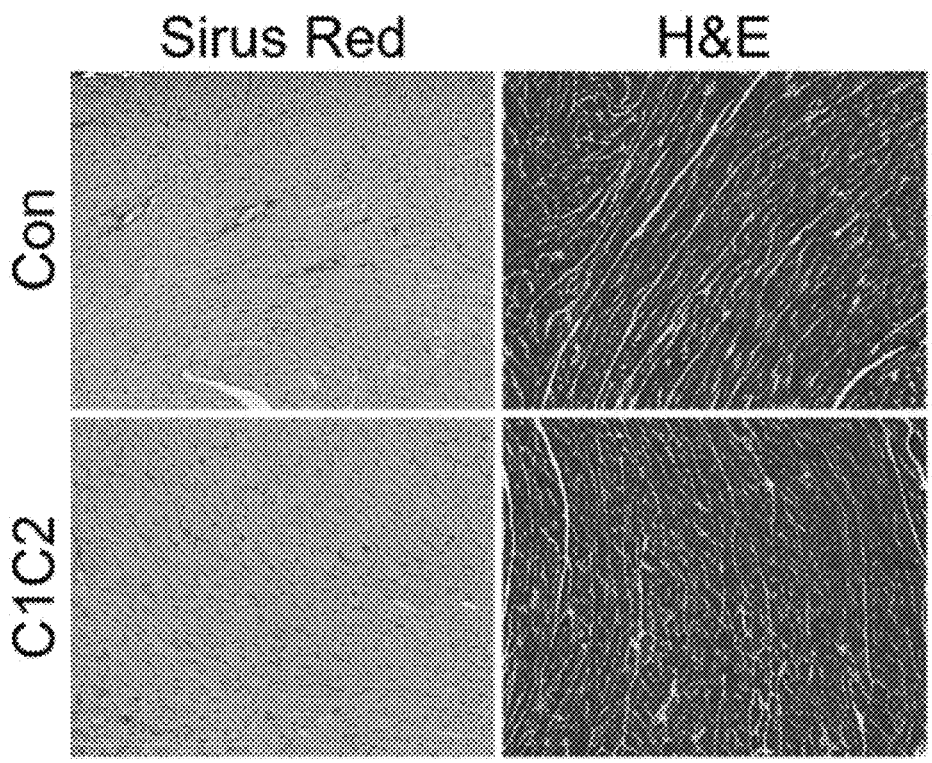
Figure 3E:
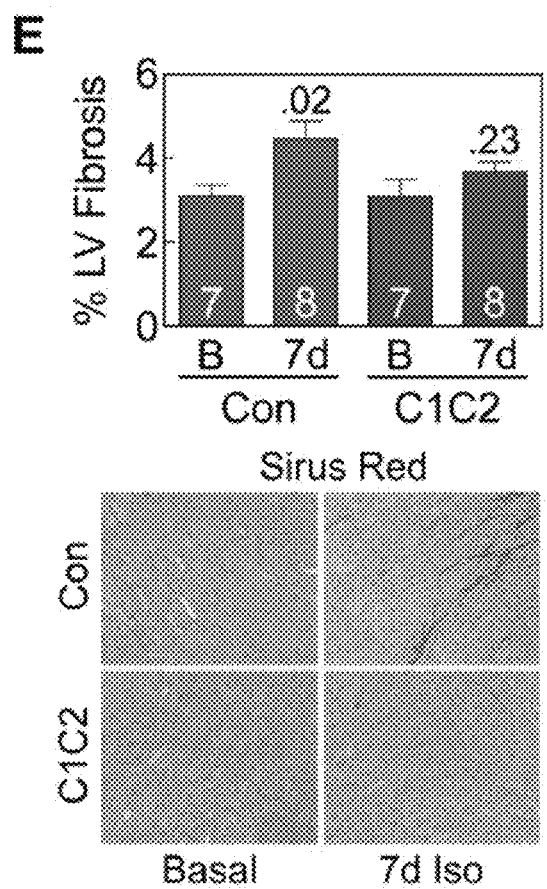

HISTOLOGY. Histological inspection showed normal morphology without group differences in fibrosis of C1C2 mice compared to control mice at 8 months of age (FIG. 2E). LV samples showed increased LV fibrosis (p = 0.02) in control mice (but not C1C2 mice) after 7 days of continuous Iso infusion (FIG. 3E).

CYCLIC AMP GENERATION AND PKA ACTIVITY. Before sustained Iso infusion, transmural LV samples showed no group differences (C1C2 vs. control mice) in basal cAMP, but Iso-stimulated cAMP production was reduced in LV samples from C1C2 mice (FIG. 2B). Stimulation of cAMP by NKH477, a forskolin analog that directly activates AC, showed no group differences (FIG. 2B). LV PKA activity in response to brief Iso or AC stimulation with NKH477 showed no group differences (FIG. 2B). Cardiac-directed expression of C1C2 did not alter mRNA expression of AC3, AC4, AC5, AC6, AC7, AC8, or AC9. AC isoform expression ranged from a 14% increase (AC6) to a 13% decrease (AC7), but none was statistically significant.

TABLE 1

Echocardiography

|  | No Infusion | | 7-Is Infusion | | pValue | | |
| --- | --- | --- | --- | --- | --- | --- | --- |
|  | Iso | C1C2 | d o | C1C2 |  | Iso |  |
| Heart rate, | 530± | 521 ± | 508 | 499 ± | 0.99 | 0.31 | 0.68 |
| End-diastolic | 3.9± | 4.0 ± | 4.0 ± | 3.9 ± | 0.56 | 0.91 | 0.88 |
| End-systolic | 2.5± | 2.6 ± | 2.7 ± | 2.7 ± | 0.68 | 0.25 | 0.90 |
| % Fractional | 38± 2 | 36 ± 2 | 32 ± | 31 ± 2 | 0.85 | 0.04 | 0.70 |

Values are mean ± SE; (group size), p values are from 2-way ANOVA.
7-day Iso ¼ 7 days continuous isoproterenol infusion; C1C2 ¼ transgenic mice with cardiac-directed C1C2 expression; Con ¼ transgene-negative sibling mice used as controls.

TABLE 2

LV Pressure Development and Decline

|  | No Iso Infusion | 7-d Iso Infusion | p Value | | |
| --- | --- | --- | --- | --- | --- |
| LV peak | 5,070 ± 553 | 3,911 ± 406 5,298 | 0.012 | 0.83 | 0.44 |
| LV peak − | −5,003 ± 527 | −3,485 ± 321 − | <0.0 | 0.64 | 0.07 |
| LV pressure, | 78 ± 4 72 ± | 62 ± 3‡ 80 ± | <0.0 | 0.05 | 0.19 |
| Heart Rate, beats/min | 458 ± 19 439 ± 19 | 447 ± 10 481 ± 17 | 0.16 | 0.40 | 0.68 |

Values are mean ± SE, (group size). There were no baseline between-group differences (Con vs. C1C2) in LV peak +dP/dt (p ¼ 0.22), LV peak −dP/dt (p ¼ 0.27), LVP (p ¼ 0.18) or heart rate (p ¼ 0.49).
*p ¼ 0.026 vs. C1C2 No Iso;
†p ¼ 0.006 vs. C1C2 No Iso;
‡p ¼ 0.012 vs. Con No Iso;
§p ¼ 0.016 vs. C1C2 No Iso (post hoc within-group comparisons using Student's t-tests with Bonferroni correction for multiple testing).
LV ¼ left ventricle; other abbreviations as in Table 1.

TABLE 3

Necropsy

|  | No Iso Infusion | 7-d Iso Infusion | p Value Iso | | |
| --- | --- | --- | --- | --- | --- |
| BW, g | 27.2 ± 3.028.2 ± 2.5 | 29.5 ± 1.126.8 ± 0.8 | 0.47 | 0.86 | 0.74 |
| LV, mg | 92 ± 8 95 ± 8 | 118 ± 6 102 ± 4 | 0.24 | 0.044 | 0.42 |
| LV/BW, | 3.5 ± 0.1 3.4 ± 0.1 | 4.0 ± 0.1 3.8 ± 0.1 | 0.65 | 0.000 | 0.17 |
| Liver/BW, | 46.0 ± 1.9 48.6 ± | 57.3 ± 1.759.3 ± 1.0 | 0.91 | <0.00 | 0.37 |
| Lung/BW, mg/g | 5.8 ± 0.4 6.2 ± 0.4 | 6.2 ± 0.2 6.3 ± 0.1 | 0.70 | 0.52 | 0.52 |

Values are mean ± SE (group size).
BW ¼ body weight; kpo ¼ 7 d; other abbreviations as in Tables 1 and 2.

Figure 4A:
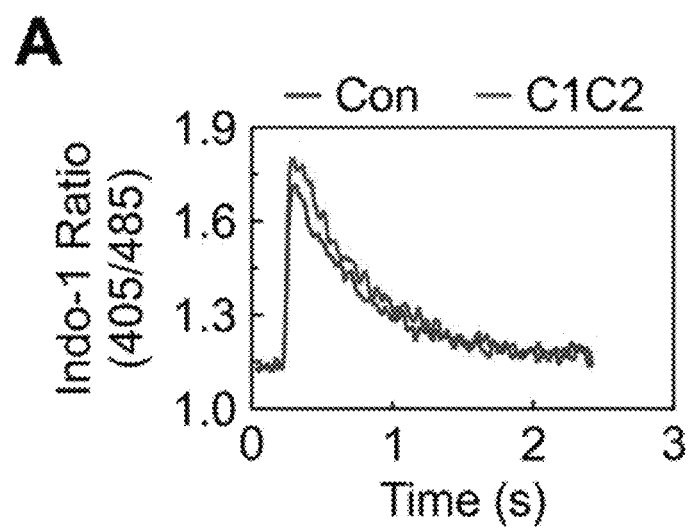
FIG. 4A-F.
Figure 4B:
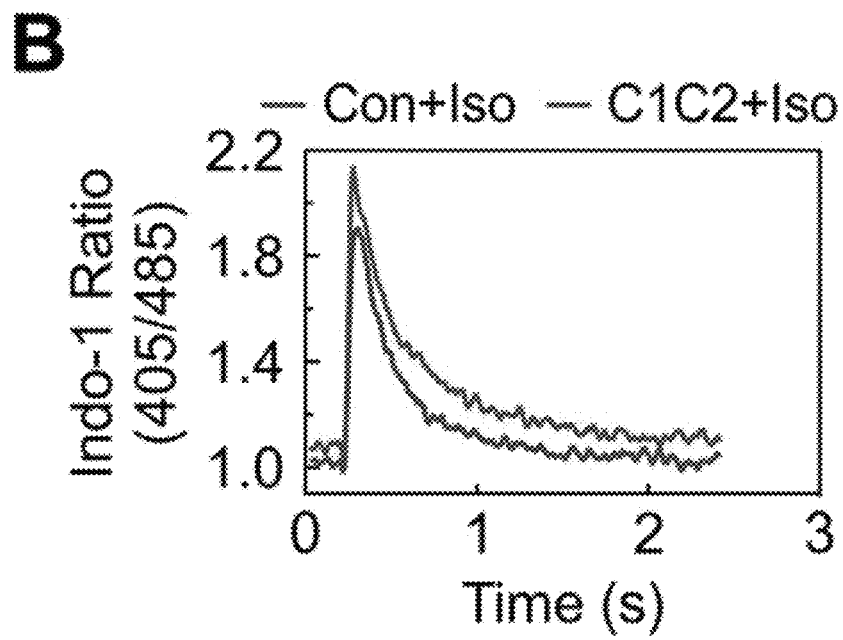
Figure 4C:
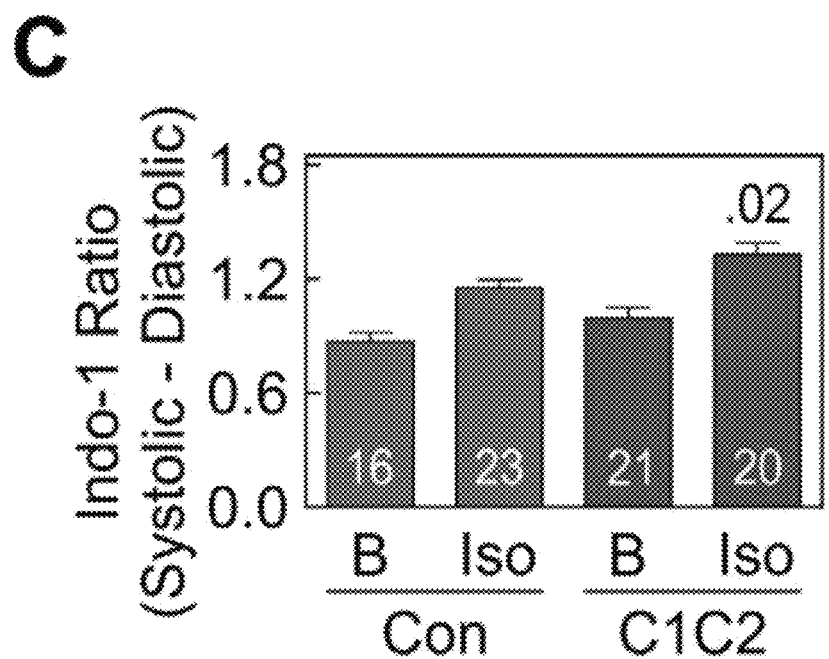

$Ca^{2+}$ TRANSIENT AND $Ca^{2+}$ HANDLING PROTEINS. Before sustained isoproterenol infusion. Basal $Ca^{2+}$ released during contraction (systolic-diastolic $Ca^{2+}$) was not affected by C1C2 expression (FIG. 4A), but peak systolic $Ca^{2+}$ transient amplitude during brief Iso stimulation was increased (p ¼ 0.02) (FIGS. 4B and 4C).

Figure 4D:
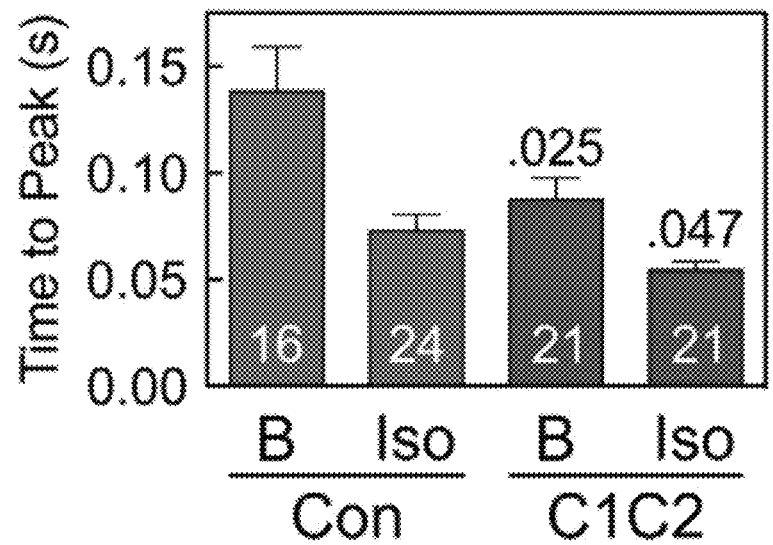
Figure 4E:
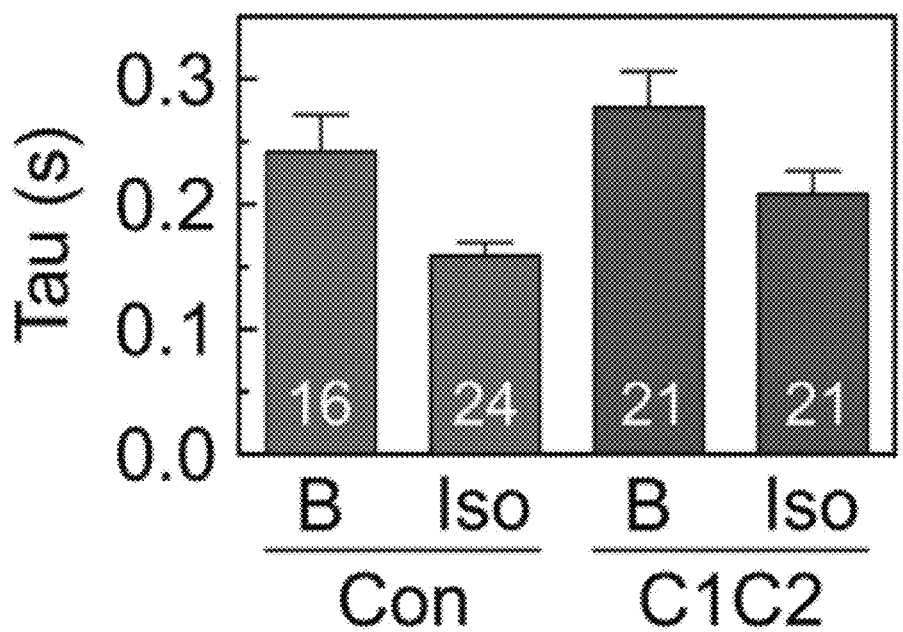
Figure 4F:
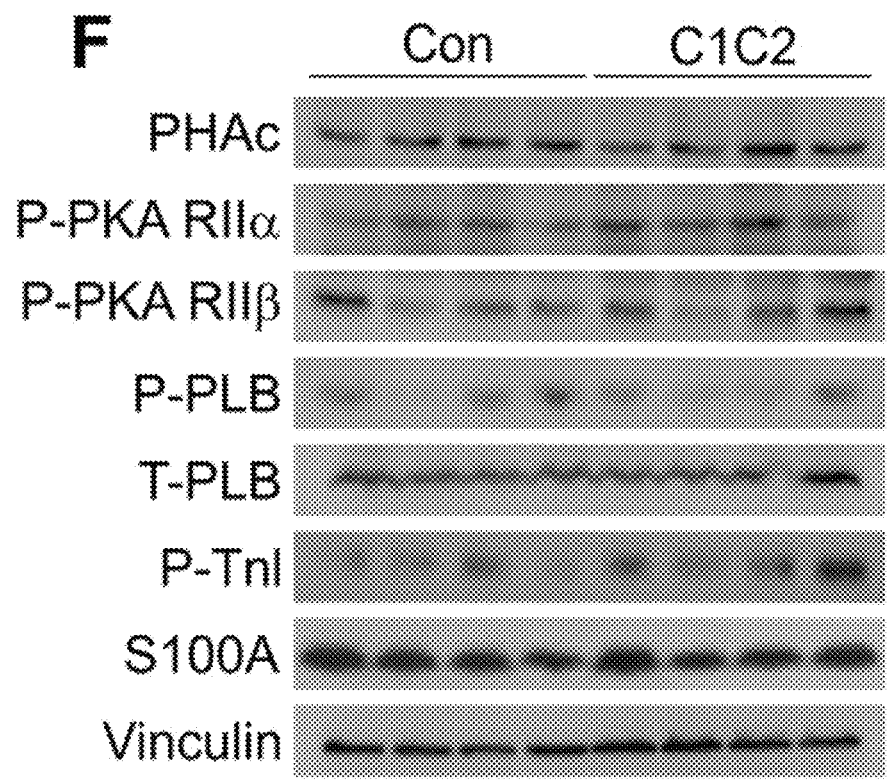

C1C2 expression reduced time to peak $Ca^{2+}$ release before (p ¼ 0.025) and during brief Iso stimulation (p ¼ 0.047) (FIG. 4D). Finally, $Ca^{2+}$ decline time (t ½, Tau) was reduced in both groups similarly after brief Iso stimulation (FIG. 4E).

Figure 5A:
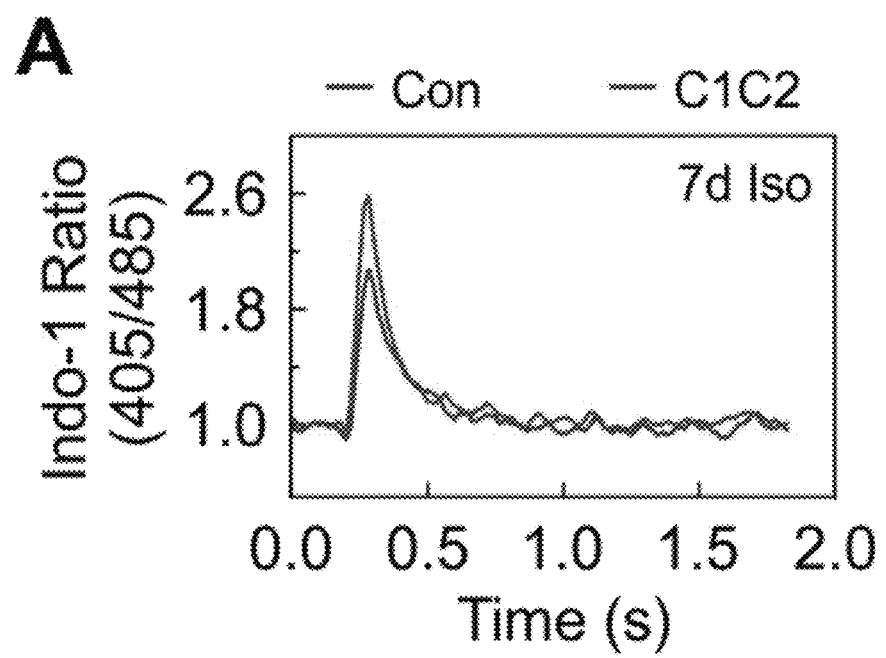
FIG. 5A-G.
Figure 5B:
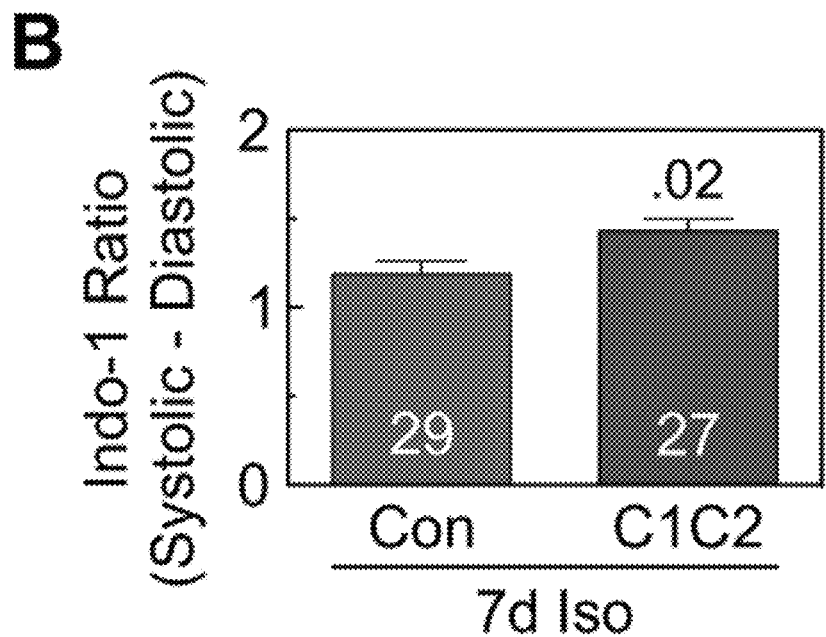
Figure 5C:
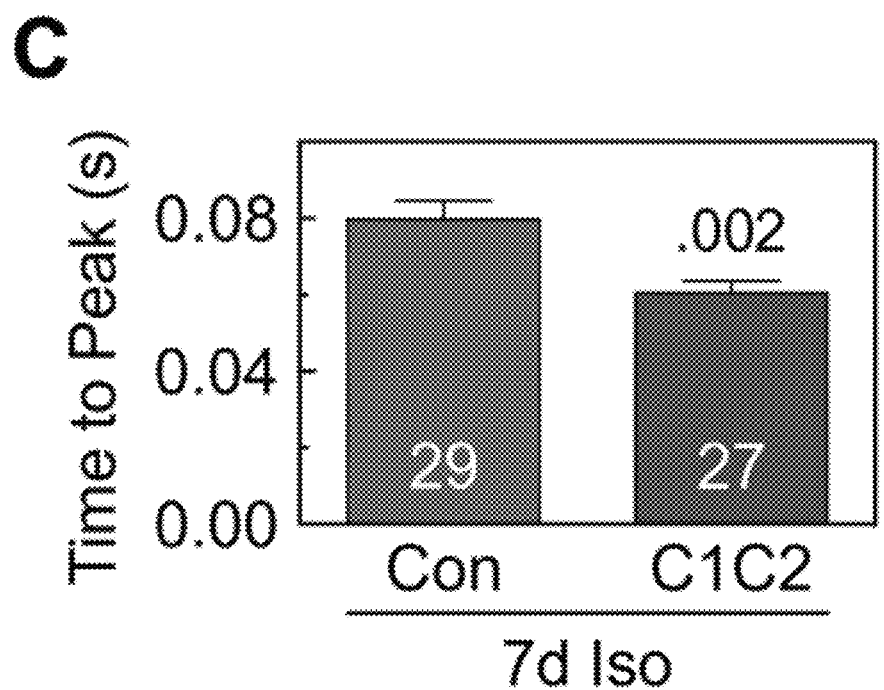
Figure 5D:
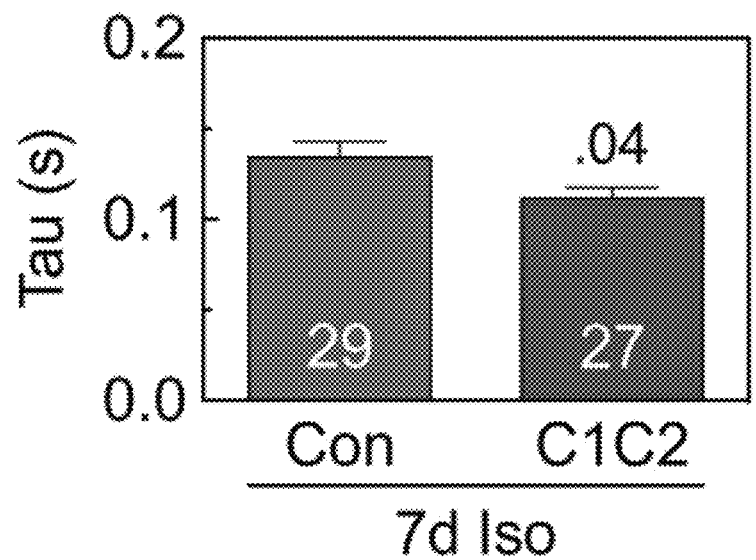
Figure 5E:
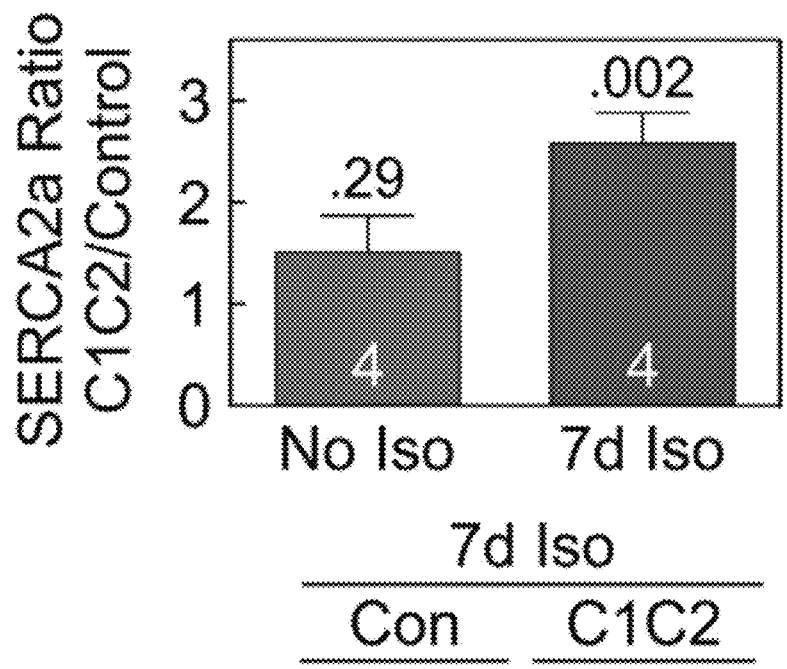
Figure 5F:
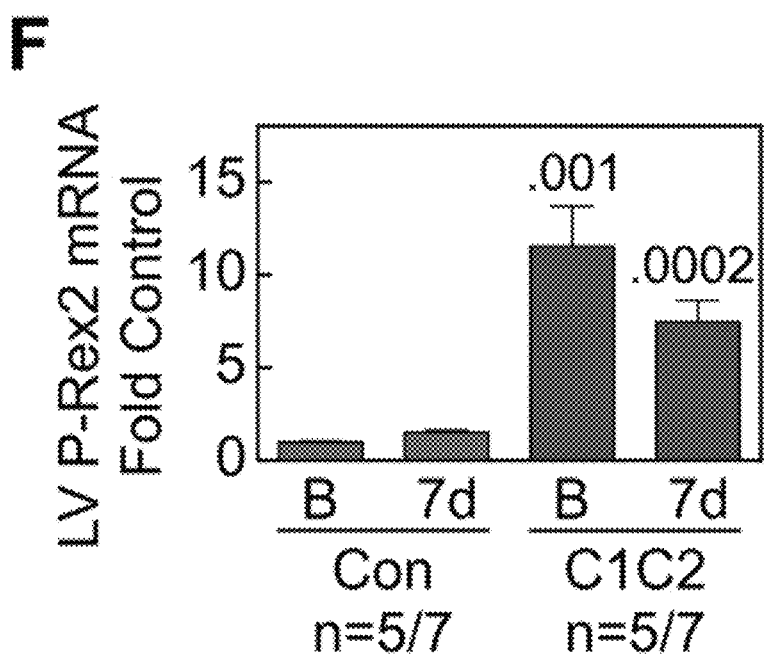
Figure 5G:
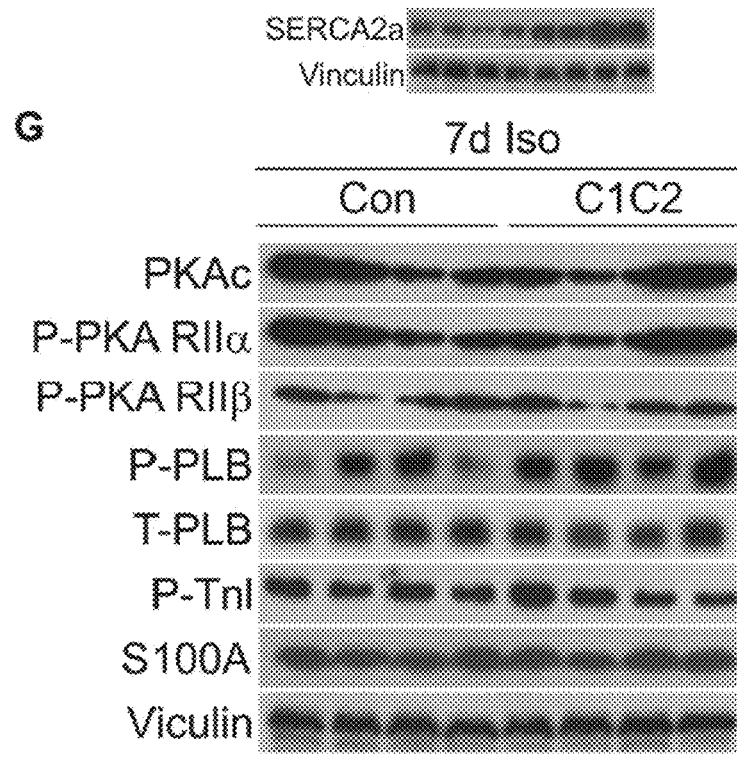

After sustained isoproterenol infusion. After 7 days of Iso infusion, C1C2 expression was associated with increased peak $Ca^{2+}$ release (FIGS. 5A and 5B) and more rapid $Ca^{2+}$ rise and decline (FIGS. 5C and 5D). The LV SERCA2a protein expression showed no group differences prior to sustained Iso infusion. However, after 7 days of Iso infusion, LV samples from C1C2 mice showed a 2.6-fold increase in SERCA2a protein content compared to control mice (p ¼ 0.002) (FIG. 5E). In vivo expression of C1C2 increased expression of P-Rex2 mRNA by 11.5-fold (p ¼ 0.001) (FIG. 5F), which remained 7.5-fold increased versus control after sustained Iso infusion (p ¼ 0.0002) (FIG. 5F). Expression or phosphorylation of other signaling proteins that modulate intracellular $Ca^{2+}$ transients (S100A1, PLB, TnI) were not altered in C1C2 LV either before (FIG. 4F) or after 7 days of Iso (FIG. 5G).

Discussion

The most important finding of this study is that, in mice with cardiac-directed expression of C1C2, sustained Iso infusion increases LV function. Seven days of continuous Iso infusion increased $Ca^{2+}$ release, reduced time to peak $Ca^{2+}$ release, and reduced rate of $Ca^{2+}$ decline (Tau) in cardiac myocytes from C1C2 mice, and LV SERCA2a content from C1C2 mice was increased. These favorable alterations in $Ca^{2+}$ handling provide mechanistic underpinnings for this interesting and unexpected LV response to catecholamine infusion.

LV FUNCTION. There were 2 lines of evidence for C1C2's favorable effects on LV function. First, despite reduced Iso-stimulated cAMP generation in LV from C1C2 transgenic mice, LV systolic and diastolic function were preserved through a wide range of Iso concentrations (FIG. 2D). This paradox reflects effects on elements that increase contractile performance independent of increases in cAMP generation.

For example, we saw increased Iso-stimulated $Ca^{2+}$ release (FIG. 4C) and increased expression of SERCA2a (FIG. 5E), events also seen with alterations in AC6 content in previous studies (20-22). The current data indicate that increased cAMP is not a requirement for beneficial alterations in $Ca^{2+}$ handling. Second, the C1C2 line not only resisted Iso-induced cardiomyopathy, but LV systolic and diastolic function was increased. After the 7-day Iso infusion, C1C2 mice showed increases in LV peak +dP/dt and peak −dP/dt (FIGS. 3A and 3B, Table 2). In normal animals, the stress of 7 days of Iso was associated with a propensity for both measurements to decline. The beneficial physiological changes seen in C1C2 mice were associated with increases in rates of $Ca^{2+}$ release and decline in cardiac myocytes from C1C2 mice (FIGS. 5A to 5D). Also seen was a 2.6-fold increase in LV SERCA2a content (FIG. 5E), which likely was of mechanistic importance in the enhancement of $Ca^{2+}$ handling. Indeed, other studies have reported that cardiac-directed expression of SERCA2a increases $Ca^{2+}$ transient amplitude (23). If these effects were also to occur in clinical settings, one would predict protection of the heart against sustained catecholamine stimulation, a common feature of clinical HF, and one thought to be responsible, at least in part, for the inexorable decline of cardiac function frequently seen in HF.

However, increased Ca$^{2+}$ uptake and release were seen in cardiac myocytes from C1C2 animals prior to 7 days of Iso infusion (FIGS. 4C and 4D), even though LV SERCA2a content was unchanged (FIG. 5E, left). However, there were no group differences in Tau before (FIG. 4E) but improved Tau after 7 days of Iso infusion (FIG. 5D), which correlated well with LV SERCA2a content, which had increased after Iso infusion (FIG. 5E, right). C1C2 expression is associated with changes in multiple intracellular events aside from SERCA2a, including an 11.5-fold increase in LV expression of P-Rex2 (FIG. 5F). P-Rex2 inhibits the activity of phosphatase and tensin homolog (PTEN), which increases Akt activation (24). PTEN deletion increases cardiac L-type Ca$^{2+}$ currents via increased Akt activation (25). Increased P-Rex2 expression and subsequent Akt activation would be predicted to increase Ca$^{2+}$ uptake and release in cardiac myocytes. C1C2 gene transfer activated Akt in cultured cardiac myocytes (FIG. 1F), supporting this idea. However, LV homogenates showed no group differences in Akt activation (data not shown). What one sees in cultured cell studies does not always reflect what one sees in LV homogenates, so linking Akt activation with Ca$^{2+}$ handling will require additional studies.

Why was the increase in LV peak +dP/dt in the C1C2 mice after sustained Iso infusion (FIG. 3A) not also seen in LV fractional shortening in the echocardio-graphic studies (Table 1)? Fractional shortening is an ejection-phase index of LV contractile function, and is therefore susceptible to alterations in afterload, an effect that does not alter LV peak +dP/dt, which occurs prior to aortic valve opening. Therefore, peak +dP/dt is a more reliable measurement of LV contractility (26). The C1C2 group showed higher LV pressure (afterload) after sustained Iso infusion (FIG. 3C), which would be predicted to lower fractional shortening.

The beneficial effects of C1C2 on LV SER-CA2a expression (FIG. 5E) and Ca$^{2+}$ release (FIGS. 5A to 5D) provide plausible underpinnings for the beneficial effects of C1C2 on LV contractile function. CARDIAC cAMP GENERATION. C1C2 expression reduced Iso-stimulated cAMP generation in LV homogenates and in cardiac myocytes, but did not reduce LV AC6 expression, or the expression of AC types 3-9. Absent the transmembrane domains of AC6, C1C2 distribution was predominantly cytoplasmic and less efficiently recruited for participation in cAMP generation following bAR stimulation. Our data indicate that C1C2 may act as a dominant negative mutant by interacting with Gas to reduce the effects of Gas on endogenous AC responsiveness. Such protection against cAMP generation while fostering increased Ca$^{2+}$ handling and more efficient myofilament activation constitutes an appealing profile for a HF therapeutic drug.

Typically, LV cAMP generating capacity is tightly linked with LV contractile function. In severe HF, LV cAMP production is 50% reduced, and LV contractile function is similarly reduced (3,8). Targeted deletion of AC6 is associated with a 60% reduction in LV cAMP generating capacity, and a proportional reduction in LV contractile function (20). In contrast, C1C2 expression was associated with preserved LV function in response to sustained bAR stimulation despite reduction in cAMP generation. In the present study, C1C2 had favorable effects on SERCA2a expression and Ca$^{2+}$ release, effects that may have increased LV function, counterbalancing decreased cAMP generation. C1C2 expression did not increase phosphorylation of PLB, troponin I (FIGS. 4F and 5G) or CREB protein (data not shown).

C1C2 AND INTRACELLULAR SIGNALING PATHWAYS. C1C2 influences other intracellular signaling pathways such as CryAB, Akt, ERK1/2 and p38 MAPK pathways (FIGS. 1F and 1G). We do not know the precise pathway by which C1C2 affects intracellular signaling and protein expression and phosphorylation. C1C2 interacts with G-protein coupled receptors, Gas, Gbg and A-kinase anchoring proteins (AKAPs), and could thereby influence intracellular signaling. Previous studies indicate that the C1C2 portion of AC6 enables AC6 targeting to lipid rafts (14).

C1C2 expression was associated with increased LV P-Rex2 expression detected by gene array and confirmed by RT-PCR (FIG. 5F). P-Rex2 inhibits the activity of PTEN and increases Akt activation (24). Activation of Akt signaling pathways by C1C2 was detected in cultured cardiac myocytes after Ad5.C1C2 gene transfer (FIG. 1F), which was quantitatively similar to effects seen with AC6. In previous studies we established that this is one of the mechanisms by which AC6 expression has beneficial effects on cardiac function (21). C1C2 mimics this property of AC6, confirming the mechanism does not require increased LV cAMP.

C1C2 expression increased phosphorylation of CryAB at S45 and S59 sites and C1C2 protein, based on co-immunoprecipitation, is physically associated with CryAB (FIG. 1G). CryAB, a member of the small heat shock protein (HSPs) family, is expressed at high levels in cardiac myocytes, and its expression protects against ischemia-reperfusion injury (27). The role of CryAB-C1C2 association will require additional studies, but it underscores the importance that protein-protein interactions play in mechanisms by which C1C2 affects cardiac function. The study of C1C2-interacting proteins is a focus of study in our laboratory.

Because of the complexity of multiple signaling pathways that are relevant in the failing heart, no single study can establish precise molecular pathways for every favorable adaptation. Despite this generic limitation, it is encouraging that cardiac-directed expression of C1C2 has a favorable impact on function of the intact heart in the setting of conditions that mimic aspects of clinical heart failure. The present study examines Iso-stimulated cardio-myopathy only at 7 days, and it remains to be seen whether these protective effects of C1C2 will persist for longer periods and in other models of heart failure.

Conclusions

Increased expression of C1C2 in cardiac myocytes and heart mimics some of the beneficial cardiac effects of AC6. C1C2 enhances Ca$^{2+}$ handling, which is of mechanistic importance in its beneficial effects. Sustained Iso infusion decreases LV function in control mice, as expected, but increases LV function in C1C2 mice. If these benefits of C1C2 expression translate to clinical settings, one would predict protection of the heart against catecholamine stimulation, a common feature in clinical HF.

Finally, C1C2 is sufficiently small to be inserted in an AAV vector with a regulated expression system. It will be interesting to determine whether transgene delivery of C1C2 via AAV can increase function of the failing heart.

Example 2: Exemplary Compositions and Methods for Treating Heart Failure

This example demonstrates that methods and compositions as provided herein including C1C2 gene transfer has beneficial effects on the failing human heart, and is effective regardless of ejection fraction (preserved or reduced), and can be used to treat individuals with heart failure.

A fusion protein (C1C2) constructed by fusing the intracellular C1 and C2 segments of adenylyl cyclase type 6 (AC6), retains beneficial effects of AC6 expression, without increasing cAMP generation. For example, transgenic mice with cardiac-directed C1C2 expression have normal left ventricular (LV) function despite reduced cAMP generation. Sustained isoproterenol (Iso) infusion reduces LV function in normal mice. In contrast, C1C2 mice show increased LV function with sustained Iso infusion. The effects of C1C2 expression in pressure-overload is unknown.

METHODS: LV pressure overload was induced by transaortic constriction (TAC) in C1C2 mice and in transgene negative mice. Three weeks after TAC, LV systolic and diastolic function were measured, and Ca2+ handling was assessed in isolated cardiac myocytes.

RESULTS: C1C2 expression reduced LV hypertrophy (p=0.017), increased LV peak pressure development (+dP/dt, p=0.018), and improved LV peak pressure decay (−dP/dt, p=0.038) in the pressure-overload. Cytosolic peak Ca2+ concentration was increased (p=0.047), and time to peak Ca2+ transient and Tau were decreased (p=0.002 and p=0.003, respectively) in cardiac myocytes isolated from pressure-overloaded hearts.

CONCLUSIONS: Cardiac-directed expression of C1C2 improves Ca2+ handling and LV systolic and diastolic function in pressure-overload. These data provide a rationale for further exploration of C1C2 gene transfer as a potential treatment for heart failure.

peak +dP/dt. LV peak +dP/dt in C1C2 mice was statistically indistinguishable from that of normal mice and was higher than that seen in TG negative mice 4 w after TAC (p=0.02), despite similar and substantial cardiac hypertrophy. In addition to higher LV peak +dP/dt in vivo, cardiac myocytes from C1C2 mice showed shorter time to peak Ca2+ transient (p=0.002) and a reduced time constant of cytosolic Ca2+ decline (Tau; p=0.003). Sarcomere shortening fraction (p=0.03) and the rate of sarcomere shortening (p<0.02) were increased in C1C2 cardiac myocytes. Myofilament sensitivity to Ca2+ was increased in systole (p=0.02) and diastole (p=0.04) in C1C2 myocytes. These findings indicate enhanced Ca2+ handling associated with C1C2 expression. Favorable effects on Ca2+ handling and LV function were associated with increased LV SERCA2a protein content (p<0.007) and reduced LV fibrosis (p=0.008). Cardiac-directed C1C2 expression improved Ca2+ handling and increased LV contractile function in pressure-overload.

Adenylyl cyclase (AC), a membrane protein in cardiac myocytes and other cells, is the effector molecule in the ß-adrenergic receptor signaling pathway, catalyzing conversion of ATP to cyclic adenosine monophosphate (cAMP). Mammalian AC consists of two transmembrane domains and two cytoplasmic domains (C1 and C2). The C1 and C2 domains form the catalytic core of AC. Many of the beneficial effects of AC6 that we previously have described are independent of cAMP generation and appear, instead, to involve intracellular AC6-protein interactions (3,4). By

|  | TAC for 3 weeks | | |
|---|---|---|---|
|  | Con | C1C2 | p |
| Effects of Cardiac-directed C1C2 Expression in Pressure-overload (3 weeks after TAC) | | | |
| BW, g | 23.3 ± 0.7 (25) | 23.3 ± 0.8 (17) | 0.99 |
| LV, mg | 173.1 ± 2.6 (25) | 152.7 ± 9.1 (17) | 0.016 |
| LV/BW, mg/g | 7.6 ± 0.23 (25) | 6.6 ± 0.4 (17) | 0.017 |
| IV +dP/dt (mmHg/s) | 4,070 ± 271 (13) | 5,609 ± 651 (6) | 0.018 |
| LV −dP/dt (mmHg/s) | −4,641 ± 347 (13) | −6,298 ± 799 (6) | 0.038 |
| Ca2+ Transient Studies (isolated cardiac myocytes) | | | |
| [Ca2+ ] Indo-1 Ratio | 0.201 ± 0.008 (26) | 0.226 ± 0.009 (23) | 0.047 |
| Time to Peak, s | 0.065 ± 0.002 (26) | 0.056 ± 0.002 (23) | 0.002 |
| Tau, s | 0.148 ± 0.006 (26) | 0.121 ± 0.006 (23) | 0.003 |

LV/BW ratio in normal C57B6 mice: 3.5 ± 0.1 mg/g;
Values are mean ± SE (group size);
p values from Student's t-test (unpaired, 2-tailed)

Example 3: Exemplary Compositions and Methods for Treating Heart Failure

This example demonstrates that methods and compositions as provided herein including C1C2 gene transfer has beneficial effects on the failing human heart, and cardiac-directed C1C2 expression improves Ca2+ handling and increases LV contractile function in pressure-overload.

Summary:

A fusion protein (C1C2) constructed by fusing the intracellular C1 and C2 segments of adenylyl cyclase type 6 (AC6) retained beneficial effects of AC6 expression, without increasing cAMP generation. The effects of cardiac-directed C1C2 expression in pressure-overload is unknown. LV pressure overload was induced by transverse aortic constriction (TAC) in C1C2 mice and in transgene negative (TG−) mice. Four weeks after TAC, LV systolic and diastolic function were measured, and Ca2+ handling was assessed. Four weeks after TAC, TG− animals showed reduced LV removal of the two transmembrane domains of AC6 and fusing the two cytoplasmic domains, as illustrated in FIG. 1A, we generated a smaller protein with an intact catalytic core that is not responsive to membrane-associated ß-adrenergic receptor stimulation, but with increased likelihood for interactions with intracellular signaling proteins. Its smaller size (compared to AC6) and its solubility in cytoplasm (16) facilitates such intracellular interactions. The smaller size would also facilitate expression in adeno-associated virus vectors. C1C2 retains binding sites for Gα, forskolin, ATP, Mg2+, as well as for some important regulatory proteins, such as snapin, A-kinase-anchoring protein (AKAP), PH domain leucine-rich protein phosphatase 2 (PHLPP2), and the phosphorylation or dephosphorylation sites for protein kinase A (PKA) (14).

These characteristics of C1C2—small size, solubility, retention of regulatory binding sites, and disengagement from cell-surface ß-adrenergic receptor stimulation—make it an attractive way to safely and effectively increase function of the failing heart. A phase 2 randomized clinical trial in patients with symptomatic heart failure (HF) showed that AC6 gene transfer is safe and potentially effective, and not associated with increased cardiac arrhythmias (8). However, a modified AC6 that circumvents production of cAMP could have advantages and is a motivation for the current studies. Indeed, we recently showed that, in mice with cardiac-directed expression of C1C2, sustained isoproterenol infusion increases rather than decreases LV function despite attenuated cAMP generation (5).

Although the isoproterenol infusion model of cardiomyopathy is useful and mimics aspects of clinical HF, to obtain a more complete picture of the potential benefits of LV C1C2 expression, we conducted studies in pressure overload—a major cause of clinical HF. Indeed, before advancing a new therapy to clinical trials, it is imperative to be certain that the strategy is safe and effective in more than a single model of disease. There are striking differences between sustained isoproterenol infusion vs pressure overload—especially when using a transgene expected to reduce cAMP generation, which would not be expected to influence response to pressure stress. In the present study we tested the hypothesis that cardiac-directed expression of C1C2, through adaptations in cytosolic Ca2+ handling, would preserve LV contractile function in the setting of severe pressure stress.

Material and Methods

Generation of C1C2 Fusion Protein:

C1C2 peptide was generated as previously described (5). Briefly, cytoplasmic domain 1 (C1, amino acids 349-576) and cytoplasmic domain 2 (C2, amino acids 939-1157) of mouse adenylyl cyclase type 6 (AC6) were ligated using a linker (12 amino acids: AAAGGIPPAAAM) (SEQ ID NO:8). The C-terminus of the generated C1C2 peptide was linked with an AU1 epitope tag (DTYRYI) (SEQ ID NO:9) to facilitate detection.

Generation of C1C2 Transgenic Mice:

Animals were used with approval by the Institutional Animal Care and Use Committee of VA San Diego Healthcare System. The generation and characterization of the cardiac-directed C1C2 murine lines were described previously (5). We documented variable transgene mRNA expression in 2 lines and used a line with a 23-fold increase in C1C2 mRNA expression (vs. endogenous AC6) in this study. C1C2 protein was 13-fold increased relative to that of the AU1 signal in transgene negative mice. We used 84 mice (40M, 44F) mean age 9±0.1 months, mean weight 31±0.6 grams. To determine mortality, we set aside 34 mice (17 per group) and did no interventions after TAC.

Transverse Aortic Constriction (TAC):

Mice were anesthetized with 5% isoflurane in oxygen (1 L/min), intubated, and ventilated (pressure-controlled). Anesthesia was maintained with 1% isoflurane in oxygen. The chest was entered at the second intercostal space at the left upper sternal border, and a segment of the aortic arch between the innominate and left carotid arteries dissected. A 7-0 silk suture was tied against a 26-gauge needle, which yields a substantial aortic constriction. Collaborators at our institution using these methods documented mean pressure gradients across the constriction of >45 mmHg (9).

Study Design:

Three groups of mice were studied: 1) control mice that did not receive TAC; 2) mice with cardiac-directed C1C2 expression that were studied 4 w after TAC; 3) transgene negative mice that were studied 4 w after TAC.

Echocardiography:

Echocardiography was performed 28±1 days after TAC, using a Vevo 3100™ system with a MX550s (32-56 MHz) transducer (Visualsonics, Toronto, Canada), as previously described (5). Transgene negative mice with no TAC (n=7) served as controls. We previously showed no baseline echocardiographic differences in C1C2 vs transgene negative mice (5). For anesthesia we used 5% isoflurane at a flow rate of 1 L/min oxygen and maintained with 1% isoflurane in oxygen.

Left Ventricular Systolic and Diastolic Function:

Mice were anesthetized by intraperitoneal injection of sodium pentobarbital (80 mg/kg). A 1.4 F micromanometer catheter (SPR 839, Millar Instruments, Houston, Tex.) was advanced via the right carotid artery across the aortic valve and into the LV to measure the left ventricular pressure. The data were recorded and analyzed using software IOX 2.9 (Emka Technologies, Christchurch, Va.) as previously reported (6).

Cardiac Myocyte Isolation:

Cardiac myocytes were isolated with the use of modified methods as previously reported (6,11)

Ca2+ Transients and Sarcomere Shortening:

Cytosolic Ca2+ transients in isolated cardiac myocytes were measured using indo-1 AM, as previously described (2,7) with modifications. Cardiac myocytes were plated onto laminin pre-coated glass cover slips and loaded with indo-1 AM (5 µM, Life Technologies, Carlsbad, Calif.) and dispersing agent, pluronic F-127™ (0.02 mg/ml, Life Technologies, Carlsbad, Calif.) for 20 minutes. After dye loading, cover slips were placed in a field stimulation superfusion chamber, and then mounted on an inverted microscope (Nikon TMD, Japan) equipped with a photomultiplier tube-based fluorescence imaging system (PTI, Edison, N.J.). During the measurements, cardiac myocytes were continuously perfused with KRH solution (125 mM NaCl, 5 mM KCl, 1.2 mM $NaH_2PO_4$, 6 mM glucose, 1.2 mM $MgCl_2$ and 25 mM HEPES, pH 7.37-7.38) containing 2 mM $CaCl_2$). Cardiac myocytes were field-stimulated at 0.3 Hz with amplitude of 10 volts and pulse width of 10 msec. Excitation wave length was set to 365 nm via a monochromator. Fluorescence emission was slit and directed to two photomultiplier tubes through 20 nm band-pass filters centered at 405 and 485 nm, respectively. The ratio F405/485 represents a measure for $[Ca2+]_i$, and EC50 for sarcomere shortening is calculated based on this ratio. Focusing on a region including several consecutive sarcomeres, simultaneous fractional shortening of sarcomere length was measured using a video edge camera (Flare 2M360-CL™, IO Industries, London, Canada) attached to the fluorescence imaging system. Ca2+ transients and sarcomere length shortening data were analyzed using FelixGX™ software (PTI, Edison, N.J.) and Clampfit™ software (Molecular Devices, Sunnyvale, Calif.).

RT-PCR:

Quantitative reverse transcription polymerase chain reaction (RT-PCR) was conducted to detect the expression level of mRNA of hypertrophy and fibrosis related proteins, as previously described (15).

Immunoblotting:

Western blots were performed to assess the expression of total or phosphorylated proteins from frozen LV samples. Antibodies were used including: SERCA2a (1:500 dilution; ENZO, Exeter, UK); p16-PLB (1:5000 dilution; Badrilla, Leeds, UK); p17-PLB (1:5000 dilution; Badrilla, Leeds, UK); p-TnI (1:500 dilution; Cell Signaling, Danvers, Mass.); p-CaMKII (1:200 dilution; Santa Cruz Biotechnology, Dallas, Tex.); p-PKA (1:1000 dilution; Cell Signaling, Danvers, Mass.); p-PKC (1:1000 dilution; Cell Signaling, Danvers, Mass.); p-Akt (1:1000 dilution; Cell Signaling, Danvers, Mass.); GAPDH (1:20000 dilution; Fitzgerald, Acton, Mass.). Protein quantification was conducted using Image Lab™ software (BIO-RAD, Hercules, Calif.).

Necropsy and Histology:

Body, liver, lung and LV weight (including interventricular septum) were recorded. Transmural sections of the LV were fixed in 10% formalin (Sigma-Aldrich), paraffin-embedded, sliced into 5-μm sections, mounted, and then counterstained with picrosirius red (to evaluate fibrosis) and hematoxylin and eosin. The slides were scanned using an Axio Scan Z1™ slide scanner (Zeiss, Oberkochen, Germany). Quantitative assessment of fibrosis, conducted on picrosirius red-stained sections, was performed using ImageJ™ software (NIH, Bethesda, Md.). The remaining LV was quickly frozen in liquid nitrogen and stored at −80° C.

Statistical Analysis:

Data acquisition and analysis were done without knowledge of group identity. Group sizes were determined by power calculations, and male and female mice were used in equal proportions. The hypothesis was that cardiac-directed expression of C1C2, through adaptations in cytosolic Ca2+ handling, would preserve LV contractile function in the setting of severe pressure stress. Therefore, the key statistical comparison was between C1C2 and TG− mice 4 weeks after TAC, and group differences were tested via Student's t-test (unpaired, two-tailed). In order to confirm that the intervention (TAC) was successful in inducing the expected alterations in LV structure and function, we also included an age- and sex-matched control group of TG− mice that did not undergo TAC. Analyses were performed using GraphPad Prism™ (GraphPad Software, Inc., San Diego, Calif.). The null hypothesis was rejected when $p<0.05$.

Results:

LV Function and Dimensions

Echocardiography (Table 1).

Ejection fraction fell and LV ESD increased 4 w after TAC to similar degrees in TG− and C1C2 mice. End-diastolic thickness of the posterior wall (p=0.0002) and the interventricular septum (p=0.06) were increased 4 w after TAC, with no between-group differences (TG− vs C1C2).

TABLE 1

Echocardiography

| | | 4 w TAC | | p |
|---|---|---|---|---|
| | No TAC (7) | TG− (19) | C1C2 (26) | TG− vs C1C2 |
| EF (%) | 64 ± 4 | 41 ± 3[A] | 40 ± 2 | .8 |
| EDD (mm) | 4.1 ± .1 | 4.5 ± .1[B] | 4.5 ± .1 | 1.0 |
| ESD (mm) | 2.7 ± .2 | 3.6 ± .2[C] | 3.6 ± .1 | 1.0 |
| PW (mm) | .7 ± .04 | 1.0 ± .03[D] | .9 ± .02 | <.02 |
| IVS (mm) | .8 ± .03 | .9 ± .03 | .9 ± .02 | 1.0 |
| HR (bpm) | 550 ± 6 | 526 ± 7 | 536 ± 4 | .4 |

For Table 1: Echocardiographic measures of LV dimension and function.

No TAC, transgene negative (n = 7) and no transverse aortic constriction (TAC); TG−, mice without C1C2 expression that underwent TAC; C1C2, transgenic mice with cardiac-directed C1C2 expression that underwent TAC; 4 w, 4 weeks after TAC; EF, ejection fraction; EDD, end-diastolic diameter; ESD, end-systolic diameter; PW, posterior wall thickness (end-diastole); IVS, interventricular wall thickness (end-diastole); HR, heart rate.

Values are mean ± SE. P values are from Student's t-test (unpaired, two tails) comparing TG− vs C1C2 4 w after TAC.

To confirm expected changes after TAC, Student's t-test was used to compare No TAC vs TG− TAC: [A]p < .001; [B]p = .06; [C]p < .04; [D]p = .0002; p values corrected for multiple comparisons (Bonferroni).

LV Pressure Development and Decay (Table 2)

It was important to obtain a measure of LV function less load-dependent than ejection fraction—especially in the setting of LV obstruction to ejection imposed by transverse aortic constriction. We therefore measured, using micromanometer catheters, peak LV pressure development, which is less load-sensitive than ejection phase indices of LV function such as ejection fraction. Four weeks after TAC, compared to control mice (no TAC) TG− animals showed reductions in LV peak +dP/dt (p=0.04), while C1C2 mice showed no such reductions (Table 2). These results indicate that C1C2 expression enabled the LV to maintain normal function despite marked pressure overload and LV hypertrophy. Consequently, LV peak +dP/dt was 19% higher than that in TG− mice (p=0.02; Table 2). LV peak −dP/dt showed no group differences, although it tended to be lower after TAC in TG− mice than in C1C2 mice (p=0.09). C1C2 mice tended to have higher LV developed pressure than TG− mice after TAC (p<0.06) (Table 2). There was no group difference in mortality 4 w after TAC placement: TG−: 3 of 17 died; C1C2: 4 of 17 died; p=0.76). The deaths were unwitnessed, and likely cardiac in nature, with pleural fluid observed in most mice.

TABLE 2

LV Function

| | | 4 w TAC | | p |
|---|---|---|---|---|
| | No TAC (11) | TG− (21) | C1C2 (19) | TG− vs C1C2 |
| LV peak +dP/dt (mmHg/s) | 4875 ± 209 | 4025 ± 231[A] | 4803 ± 170 | .02 |
| LV peak −dP/dt (mmHg/s) | −4816 ± 213 | −4378 ± 325 | −5097 ± 249 | .09 |
| LV Pressure (mmHg) | 85 ± 3 | 105 ± 5[B] | 120 ± 4 | <.06 |
| HR (bpm) | 429 ± 13 | 399 ± 8 | 426 ± 17 | .15 |

For Table 2: Left ventricular function 4 weeks (4 w) after transverse aortic constriction (TAC).

The No TAC group is TG− mice. C1C2 expression did not alter Pre-TAC values. C1C2, mice with cardiac-directed C1C2 expression; LV, left ventricular; +dP/dt, peak rate of LV pressure development; −dP/dt, peak rate of LV pressure decline; HR, heart rate; LV function was superior in C1C2 vs TG− mice: LV peak +dP/dt and LV developed pressure were increased, and LV peak −dP/dt tended to increase, reaching normal levels.

Values are mean ± SE. P values are from Student's t-test (unpaired, 2-tailed).

To determine changes after TAC, Student's t-test was used to compare No TAC vs TG− TAC: [A]p = .04; [B]p = .02; p values corrected for multiple comparisons (Bonferroni).

Ca2+ Handling

Ca2+ transients. To investigate the underlying Ca2+ handling changes, we measured Ca2+ transients in cardiac myocytes isolated 4 w after TAC from C1C2 and TG− mice and from TG− mice that had not undergone TAC. Four weeks after TAC cardiac myocytes from C1C2 mice showed superior Ca2+ handling vs TG− mice. Ca2+ transient amplitude was higher (FIGS. 7A and 7B; p=0.04'7), time to peak Ca2+ transient was shorter (FIG. 7C; p=0.002 vs TG−), and the time constant of cytosolic Ca2+ decline (Tau) was more rapid (FIG. 7D; p=0.003 vs TG−). These favorable effects of cardiac-directed C1C2 indicate superior Ca2+ handling after TAC.

Sarcomere shortening. As an additional means to assess cardiac function, we measured sarcomere shortening in cardiac myocytes 4 w after TAC (FIG. 8). Cardiac myocytes isolated from mice with cardiac-directed C1C2 showed less deterioration in performance vs TG− mice. Sarcomere fractional shortening (FIGS. 8A and 8B; p=0.03) and the peak rate of sarcomere shortening (+dL/dt) (FIG. 3C; p<0.02) were both higher. The peak rate of sarcomere shortening (−dL/dt) tended to be more rapid in cardiac myocytes from C1C2 mice (FIG. 8D; p=0.08). These favorable effects of cardiac-directed C1C2 indicate superior cardiac myocyte function after TAC.

Myofilament sensitivity to Ca2+. Using Ca2+ transient measurements and sarcomere shortening, we analyzed myofilament sensitivity to Ca2+. We used Indo-1 F405/485 ratio as an estimate of $[Ca2+]_i$. Cardiac myocytes from mice with cardiac-directed C1C2 expression showed higher Ca2+ sensitivity, defined as reduced Ca2+ concentration required to attain 50% of maximal sarcomere shortening (EC50).

In cardiac myocytes isolated from C1C2 mice 4 w after TAC, EC50 for Ca2+ was lower during contraction (FIGS. 9A and 9B; p=0.02) and relaxation (FIGS. 9A and 9C; p=0.04) compared with TG− mice.

LV Ca2+ Handling Protein Expression

To determine potential mechanisms underlying the favorable effects of cardiac-directed C1C2 expression in the setting of pressure overload, we used immunoblotting to assess key signaling proteins. Four weeks after TAC, LV samples from C1C2 mice showed a 2.3-fold higher sarco/endoplasmic reticulum Ca2+-ATPase (SERCA2a) protein content vs TG− mice (p<0.007; FIG. 10 and Table 3). There were no group differences in LV expression of phosphorylated forms of phospholamban, troponin I, CaMKII, PKA, PKC, RyR2 or Akt (FIG. 10 and Table 3).

TABLE 3

Ca2+ Handling and Related Proteins

|  | 4 w TAC | | |
|---|---|---|---|
|  | TG- (4) | C1C2 (4) | p |
| SERCA2a | .9 ± .2 | 2.2 ± .3 | .007 |
| p16-PLB | .4 ± .1 | .6 ± .1 | .5 |
| p17-PLB | 1.1 ± .1 | 1.1 ± .1 | .8 |
| p-ThI | .9 ± .1 | .9 ± .1 | .7 |
| p-CaMKII | 1.6 ± .4 | 2.2 ± .3 | .3 |
| p-PKA | .7 ± .1 | .7 ± .03 | .5 |
| p-PKC | .1 ± .02 | .1 ± .03 | .2 |
| p-RyR2 | 1.5 ± .1 | 1.2 ± .1 | .2 |
| p-Akt | .3 ± .05 | .3 ± .06 | .5 |

For Table 3: Immunoblotting analysis of LV Ca2+ handling proteins 4 w TAC, 4 weeks after transverse aortic constriction; TG-, transgene negative mice; C1C2, transgenic mice with cardiac-directed C1C2 expression. PLB, phospholamban; TnI, troponin I; CaMKII, Ca2+/Calmodulin-dependent protein kinase-II; PKA, protein kinase A; PKC, protein kinase C; RyR2, ryanodine receptor-2.
Values are mean ± SE and reflect relative expression vs GAPDH; p values from Student's t-test (unpaired, two-tailed).
See FIG. 10 for immunoblots.

TABLE 4

LV mRNA Expression of Markers of Hypertrophy and Fibrosis

|  | No TAC | 4 w TAC | | p |
|---|---|---|---|---|
|  | (5) | TG- (6) | C1C2 (6) | TG- vs C1C2 |
| ANF | 19 ± 2 | 178 ± 63 | 100 ± 22 | .27 |
| BNP | 27 ± 2 | 237 ± 53 | 231 ± 62 | .94 |
| β-MHC | .4 ± .1 | 8 ± 2 | 4 ± 1 | .10 |
| α-sk actin | 23 ± 7 | 97 ± 17 | 103 ± 23 | .84 |
| Collagen1α1 | .21 ± .03 | .58 ± .06 | .58 ± .06 | 1.0 |
| Collagen3α1 | .19 ± .02 | .43 ± .04 | .35 ± .05 | .24 |

For Table 4: LV mRNA Expression of Markers of Hypertrophy and Fibrosis As anticipated, there were increases in LV mRNA expression of multiple markers of LV stress 4 w after TAC: atrial natriuretic factor (ANF; p = .05), brain natriuretic peptide (BNP; p = .02), β-myosin heavy chain (β-MHC; p = .003) and α-skeletal actin (α-sk actin; p = .015).
However, only β-MHC showed a between-group difference, with C1C2 mice showing lower expression than TG- mice (p = .03).
Four weeks after TAC, LV collagen1α1 and collagen3α1 mRNA expression were increased overall (p = .002, for both).

In Table 4: TAC, transverse aortic constriction; No TAC, transgene negative mice; C1C2, transgenic mice with cardiac-directed C1C2 expression; TG−, transgene negative mice; 4 w, 4 weeks. Values are relative expression from LV samples. These data were normalized to expression of the housekeeping gene, hypoxanthine guanine phosphoribosyl transferase (HPRT). Values are mean±SE and reflect relative expression vs control gene; p values from Student's t-test (unpaired, two-tailed).

Histology: Transmural LV samples from C1C2 mice 4 w after TAC showed less fibrosis in C1C2 as compared with TG− mice (FIG. 11; p=0.008).

Necropsy (see Table 5): Although there was marked LV hypertrophy associated with TAC (80% increases in LV weight; p<0.0002 vs No TAC), no differences were observed between C1C2 and TG− mice 4 w after TAC. There also was trend toward an increase in lung to body weight ratio of 52% (p=0.06 vs No TAC), but with no C1C2 vs TG− differences (see Table 5).

TABLE 5

Necropsy

|  | No TAC | 4 w TAC | | P |
|---|---|---|---|---|
|  | (12) | TG- (14) | C1C2 (12) | TG- vs C1C2 |
| Body Weight (g) | 32 ± 2 | 31 ± 1 | 31 ± 1 | 1.0 |
| LV (mg) | 96 ± 5 | 173 ± 10$^A$ | 182 ± 13 | .58 |
| LV/BW (mg/g) | 3 ± .1 | 5.6 ± .4$^A$ | 6 ± .4 | .49 |
| RV (mg) | 27 ± 1 | 31 ± 2 | 30 ± 3 | .78 |
| Liver/BW (mg/g) | 43 ± 1 | 41 ± 1 | 41 ± 1 | 1.0 |
| Lung/BW (mg/g) | 4.8 ± .3 | 7.3 ± 1$^B$ | 7.1 ± .7 | .88 |

Values are mean ± SE. No TAC, TG negative mice without transverse aortic constriction; TG-, transgene negative mice; C1C2, transgenic mice with cardiac-directed C1C2 expression; 4 w, 4 weeks; BW, body weight; LV, left ventricle (includes septum).
P values from Student's t-test (unpaired, two-tailed).
Student's t-test was used to compare No TAC vs TG- TAC: $^A$p < .0002; $^B$p = .06; p values corrected for multiple comparisons (Bonferroni).

FIGURE LEGENDS

FIG. 1. C1C2 Design. The diagram depicts the C1C2 construct that forms the catalytic core. M1 and M2, transmembrane domains of AC6; C1 and C2, cytoplasmic domains of AC6; Linker, 12 amino acids.

FIG. 7A-D. Ca2+ transients. Cardiomyocytes were isolated from control mice (Con: no TAC no C1C2 expression) and from transgene negative (TG−) and C1C2 mice four weeks (4 w) after TAC. Cytosolic Ca2+ transients were measured with a fluorescence microscope using the Ca2+ indicator, Indo-1 AM. A. Representative Indo-1 Ca2+ transient recordings from cardiomyocytes. B. Ca2+ transient amplitude tended to be lower (p=0.06) TG− mice 4 w after TAC, but with relative preservation of Ca2+ transient amplitude in cardiac myocytes from C1C2 mice. C. Time to peak Ca2+ transient showed an overall difference (p=0.016) and cardiac myocytes from C1C2 mice had more rapid cytosolic Ca2+ increase 4 w after TAC (p=0.007). D. Time constant of cytosolic Ca2+ decline (Tau) showed an overall difference (p=0.0045) and cardiac myocytes from C1C2 mice had more rapid cytosolic Ca2+ decline (p=0.0015). Data are mean +SE. Numbers in bars denote the number of cardiomyocytes per group, obtained from 6 mice per group (2-5 cells per mouse, blinded to group identity). P value is from 1-Way ANOVA (result in upper left corner of each panel); TG− vs C1C2 p value from Sidak's multiple comparison test with correction.

FIG. 8A-D. Sarcomere shortening. Cardiomyocytes were isolated from control mice (Con: no TAC or C1C2 expression) and from transgene negative (TG−) and C1C2 mice four weeks (4 w) after TAC. Sarcomere length and shortening were measured using edge detection.

A. Representative sarcomere shortening traces recorded from cardiomyocytes from C1C2 and TG− mice 4 w after TAC. B. Fractional shortening (FS) showed overall differences (p=0.01) and was higher (p<0.03) in cardiac myocytes from C1C2 mice vs TG− mice 4 w after TAC. C. Peak rate of cardiac myocyte sarcomere shortening (+dL/dt) showed overall differences (p=0.002) and a between-group difference (p<0.02) favoring mice with cardiac-directed C1C2 expression. D. Peak rate of sarcomere relaxation (−dL/dt) showed an overall difference (p=0.009) and tended to be more rapid in cardiac myocytes from TG− vs C1C2 mice 4 w after TAC (p=0.06). Data are mean +SE. Numbers in bars denote the number of cardiomyocytes, obtained from 6 mice per group (4-6 cells per mouse, blinded to group identity). P value (upper left corner of each panel) is from 1-Way ANOVA; TG− vs C1C2 p value from Sidak's multiple comparison test with correction.

FIG. 9A-C. Myofilament sensitivity. Myofilament sensitivity to Ca2+ was analyzed based on Ca2+ transients and simultaneous sarcomere shortening in cardiomyocytes from C1C2 mice and TG negative mice 4 weeks after TAC. A. Mean phase loops from cardiomyocytes from each group. Arrows indicate loop direction. The loop from cardiac myocytes isolated from C1C2 mice 4 w after TAC shows a leftward shift vs the TG negative group, indicating increased myofilament sensitivity to cytosolic Ca2+. B. During contraction, EC50 for cytosolic Ca2+(Indo-1 ratio) was reduced in C1C2 group (p=0.03) confirming increased myofilament Ca2+ sensitivity. C. During relaxation, EC50 was lower in cardiac myocytes from the C1C2 mice (p=0.04), which indicates increased myofilament Ca2+ sensitivity in diastole. Error bars denote mean±SE from 16-21 cardiomyocytes per group, isolated from 6 mice per group (2-4 cells per mouse, blinded to group identity). P value is from Student's t-test (unpaired, two-tailed).

FIG. 10A-B. Immunoblotting. A. No group differences in LV phosphorylated PLB (p16 or p17), TnI, CaMKII, PKA, PKC, RyR2 or Akt were seen 4 w after TAC. B. LV SERCA2a content was 2.3-fold higher in C1C2 4 weeks after TAC (p<0.007). Data in B are standardized to GAPDH and show relative group differences. Error bars denote mean±SE. P value is from Student's t-test (unpaired, two-tailed).

FIG. 11A-B. LV fibrosis. Upper image: Representative images of transmural LV samples stained with picrosirius red and hematoxylin and eosin (H&E), 4 w after TAC (10× magnification); lower image: Evaluation of fibrosis using ImageJ showed less fibrosis in LV from C1C2 mice (p=0.008). Error bars denote mean±SE. P value is from Student's t-test (unpaired, two-tailed).

Discussion

The most important finding of this study is that cardiac-directed expression of C1C2 protects the heart against the deleterious effects of pressure stress. For example, 4 w after TAC, cardiac expression of C1C2 preserved LV systolic function as measured by LV peak +dP/dt. Four weeks after TAC, LV peak +dP/dt was statistically indistinguishable from that of normal mice without TAC and was 19% higher than that seen in TG negative mice 4 w after TAC (p=0.02; Table 2). Thus, despite severe mechanical hindrance to LV ejection, contractile function in C1C2 mice was preserved.

Measurement of the peak rate of pressure development is particularly germane in the setting of aortic constriction because the peak rate occurs prior to opening of the aortic valve and provides information on intrinsic contractile function relatively isolated from the effects of the mechanical obstruction—something that ejection fraction—an ejection-phase index of LV function—does not provide (10). These data suggest an inherent increase in LV contractile function that should be of utility in clinical settings associated with pressure overload such as systemic hypertension. We did not see (nor did we expect) reduction in LV hypertrophy following aortic constriction, because C1C2 expression is not known to influence hypertrophic signaling pathways.

The preservation of LV function in C1C2 mice revealed by the rate of LV pressure development was also demonstrated by other measures. For example, studies of isolated cardiac myocytes showed that the time to peak Ca2+ transient amplitude was shorter in cardiac myocytes from C1C2 mice (p=0.002; FIG. 7C). In the Ca2+ transient studies, we also saw preservation of the rate of cytosolic Ca2+ decline (Tau; p=0.003; FIG. 7D) among C1C2 cardiac myocytes—a feature that would be expected to benefit LV diastolic function. Unstimulated (basal) peak Ca2+ release and Tau showed no differences in cardiac myocytes from TG− and C1C2 mice (no TAC), as we reported previously (5).

As a further means to explore C1C2's effects, we measured sarcomere shortening in cardiac myocytes isolated 4 w after TAC. These data showed higher fractional shortening (p=0.03; FIGS. 8A and 8B) and higher rates of sarcomere shortening (+dL/dt; p<0.02; FIG. 8C). Although C1C2 tended to increase −dL/dt after TAC (vs TG− after TAC), it did not reach criteria for significance (p=0.08; FIG. 8D). In general, the benefits of C1C2 in pressure overload seen in the intact heart were also seen in isolated cardiac myocytes.

Previous studies indicated that C1C2 improves Ca2+ handling (5). However, no previous studies included measures of myofilament Ca2+ sensitivity. By examining the relationship between Ca2+ transients and sarcomere shortening at different cytoplasmic Ca2+ concentrations, we determined the effective concentration for 50% of maximal shortening and relaxation. These data show a leftward shift in C1C2 cardiac myocyte compared with cardiac myocytes from TG negative mice, indicating higher myofilament sensitivity to cytosolic Ca2+(FIG. 9A). During contraction, EC50 for cytosolic Ca2+ was lower in C1C2 group (p=0.02; FIG. 9B) confirming increased myofilament Ca2+ sensitivity. During relaxation, EC50 was reduced in cardiac myocytes from the C1C2 mice (p=0.04; FIG. 9C), which indicates increased myofilament Ca2+ sensitivity also occurs in diastole. These data provide a potential mechanistic underpinning for the beneficial effects of C1C2 expression—an increase in myofilament Ca2+ sensitivity. This makes sense, because the intracellular distribution of C1C2 enables protein-protein interactions which enhance Ca2+ handling (5).

Regarding the molecular mechanism by which C1C2 affects Ca2+ handling, we found increased LV SERCA2a protein content in C1C2 vs TG negative mice (FIGS. 10A and 10B). In diastole, a reduced time constant of Ca2+ decline (Tau) indicates improved Ca2+ uptake. The sodium-Ca2+ exchanger (NCX) and sarcoplasmic reticulum (SR) are the primary means for Ca2+ reuptake in diastole (1). In mice, NCX accounts for only 5% of the Ca2+ uptake, and SERCA2a for 95% (2). Our finding of increased LV SERCA2a protein content in samples from C1C2 mice 4 w after TAC provides a plausible mechanism for improved LV Ca2+ handling.

SERCA2a activity can be regulated by phospholamban (PLB). However, we found no group differences in p16-PLB, p17-PLB, and no change in p-PKA. We previously have shown that cardiac-directed C1C2 increased LV SERCA2a content in the absence of increasing cAMP generation or PLB expression in the setting of sustained ß-adrenergic receptor stimulation (5).
The precise molecular pathway by which C1C2 expression regulates SERCA2a expression will require additional cell-based studies.

Cardiac-directed expression of AC6 in TAC (13), unlike C1C2, increased LV PLB phosphorylation at Ser16. This difference between C1C2 and AC6 expression in TAC may reflect the relative disengagement of C1C2 from the influence of cell-surface β-adrenergic receptor stimulation and reduced cAMP generation—a potential advantage conferred by C1C2 expression over AC6 expression. We previously reported that C1C2 expression reduces isoproterenol-stimulated cAMP generation in LV membranes and in cardiac myocytes (5). C1C2 is found predominantly in the cytoplasm of cardiac myocytes and is, therefore, less accessible to stimulation via cell surface βARs. It is noteworthy that even though LV AC6 expression (and other AC types) is unaltered in C1C2 mice (5), ß-adrenergic receptor mediated cAMP production is impaired, presumably through a dominant negative effect of C1C2 interacting with Gαs to reduce endogenous AC responsiveness. An appealing profile for a heart failure therapeutic would include limitation of cAMP generation while promoting more efficient myofilament Ca2+ sensitivity, an effect that we have shown in the present studies (FIG. 9).

We previously showed in cultured cardiac myocytes that C1C2 gene transfer affects intracellular signaling pathways such as CryAB, Akt, ERK1/2 and p38 MAPK (5). C1C2 may influence intracellular signaling by interacting with G-protein coupled receptors, Gαs, Gßγ and A-kinase anchoring proteins. Indeed, the C1C2 portion of AC6 is important in targeting AC6 to lipid rafts (17). We reported previously that C1C2 expression in isolated cardiac myocytes increases phosphorylation of Akt at Ser308 and Thr473 and phosphorylation of downstream Akt target proteins (5). However, we did not find increased Akt activation in LV homogenates from C1C2 mice in the present study, which may reflect the inherent limitations of defining signaling events in LV homogenates vs cells or may represent model differences (isoproterenol infusion vs TAC).

There were 10-fold increases compared with normal mice in molecular markers of hypertrophy 4 w after TAC (Table 4), but only ß-MHC showed a C1C2 vs TG– difference, with C1C2 LV samples showing 50% lower values than TG– (p=0.03). Necropsy revealed the expected severe LV hypertrophy (Table 5), similar in both experimental groups. However, LV samples from C1C2 mice 4 w after TAC showed less fibrosis than TG negative mice (p=0.008; FIG. 11). LV collagen1α1 and collagen3α1 mRNA expression were increased similarly in both groups (Table 4). A reduction in LV fibrosis in clinical settings would be anticipated to enhance diastolic function. Although the increase in contractile function conferred by C1C2 appears to be a consequence of enhanced Ca2+ handling, reduced fibrosis may reflect the disengagement of C1C2 from cell surface ß-adrenergic receptor stimulation. Thus, fibrosis induced by sustained ß-adrenergic receptor stimulation would be reduced. The mechanism by which cardiac-directed C1C2 expression reduces LV fibrosis in response to pressure overload will require additional studies. However, the improved contractile function indicates that C1C2 withstood the stress of increased pressure in a superior manner. Similarly, in our previous study of isoproterenol-induced cardiomyopathy, fibrosis was seen in transgene negative mice, but not in C1C2 mice (5). Thus, C1C2 appears to reduce fibrosis in a variety of pathophysiological settings, increasing the likelihood it could do so in clinical settings.

Although we found increased LV SERCA2a in C1C2 mice after TAC, SERCA2a may not be the sole molecular signaling event that gave rise to such striking increases in Ca2+ handling. The failing heart manifests multiple signaling abnormalities, and there is always unavoidable uncertainty using animal models to test therapies that will be useful in clinical settings. Despite these inescapable limitations, it is promising that cardiac-directed expression of C1C2 has such a favorable impact on function of the intact heart in pressure overload, a pathophysiological context frequently encountered in clinical HF. The present study examined pressure overload at 4 weeks. Whether the protective effects of C1C2 will persist for longer periods and in other models of heart failure remains to be seen.

Limitations.

Despite favorable alterations in Ca2+ handling and LV contractile function in C1C2 mice after TAC, no group difference was seen in ejection fraction. However, the model under study uses a mechanical obstruction to LV ejection (aortic constriction), so we did not expect to alter the degree of obstruction by the intervention. The rationale was to determine whether C1C2 expression would change Ca2+ handling and LV contractile function in the setting of pressure overload. Just as severe clinical aortic stenosis has no remedy other than replacement of the aortic valve (surgically or via transcatheter aortic valve replacement), it is not expected that other interventions would remedy a mechanical obstruction to LV outflow.

In conclusion, cardiac-directed C1C2 expression increases LV systolic function and measures of diastolic function in pressure-overload. The mechanism for these benefits resides in increases in many aspects of Ca2+ handling, which result in direct effects on sarcomere shortening and myofilament Ca2+ sensitivity, associated with increased expression of LV SERCA2a. These studies, taken together with the previous demonstration that C1C2 protects the heart from isoproterenol-induced cardiomyopathy, indicate that increasing cardiac content of C1C2 is likely to be of benefit in HF of diverse causes.

REFERENCES—EXAMPLE 1

1. Tang W J, Gilman A G. Construction of a soluble adenylyl cyclase activated by Gs alpha and for-skolin. Science 1995; 268:1769-72.
2. Sunahara R K, Dessauer C W, Whisnant R E, Kleuss C, Gilman A G. Interaction of Gsa with the cytosolic domains of mammalian adenylyl cyclase. J Biol Chem 1997; 272:22265-71.
3. Ping P, Anzai T, Gao M, Hammond H K. Adenylyl cyclase and G protein receptor kinase expression during development of heart failure. Am J Physiol 1997; 273:H707-17.
4. Roth D M, Bayat H, Drumm J D, et al. Adenylyl cyclase increases survival in cardiomyopathy. Cir-culation 2002; 105:1989-94.
5. Takahashi T, Tang T, Lai N C, et al. Increased cardiac adenylyl cyclase expression is associated with increased survival after myocardial infarction. Circulation 2006; 114:388-96.
6. Timofeyev V, He Y, Tutej a D, et al. Cardiac-directed expression of adenylyl cyclase reverses electrical remodeling in cardiomyopathy. J Mol Cell Cardiol 2006; 41:170-81.
7. Sastry A, Arnold E, Gurji H, et al. Cardiac-directed expression of adenylyl cyclase VI fa-cilitates atrioventricular nodal conduction. J Am Coll Cardiol 2006; 48:559-65.
8. Lai N C, Roth D M, Gao M H, et al. Intracoronary adenovirus encoding adenylyl cyclase VI increases left ventricular function in heart failure. Circula-tion 2004; 110:330-6.
9. Tang T, Gao M R, Roth D M, Guo T, Hammond H K. Adenylyl cyclase type VI corrects cardiac sarcoplasmic reticulum calcium uptake defects in cardiomyopathy. Am J Physiol Heart Circ Physiol 2004; 287:H1906-12.
10. Gao M R, Tang T, Guo T, Sun S Q, Feramisco J R, Hammond H K. Adenylyl cyclase type VI gene transfer reduces phospholamban expression in cardiac myocytes via activating transcription factor 3. J Biol Chem 2004; 279: 38797-802.
11. Lai N C, Tang T, Gao M H, et al. Activation of cardiac adenylyl cyclase expression increases function of the failing ischemic heart in mice. J Am Coll Cardiol 2008; 51:1490-7.
12. Hammond H K, Penny W F, Traverse J H, et al. Intracoronary gene transfer of adenylyl cyclase 6 in patients with heart failure: a randomized clinical trial. JAMA Cardiol 2016; 1(2):163-71.
13. Gao M H, Lai N C, Tang T, et al. Preserved car-diac function despite marked impairment of cAMP generation. PLoS One 2013; 8:e72151.
14. Ostrom R S. The C1 and C2 domains target human type 6 adenylyl cyclase to lipid rafts and caveolae. Cell Signal 2009; 21:301-8.
15. Gao M H, Lai N C, Roth D M, et al. Adenylylcy-clase increases responsiveness to catecholamine stimulation in transgenic mice. Circulation 1999; 99:1618-22.
16. O'Connell T D, Rodrigo M C, Simpson P C. Isolation and culture of adult mouse cardiac myocytes. Methods Mol Biol 2007; 357:271-96.
17. Gao M H, Lai N C, Miyanohara A, et al. Intrave-nous adeno-associated virus serotype 8 encoding urocortin-2 provides sustained augmentation of left ventricular function in mice. Hum Gene Ther 2013; 24:777-85.
18. Gao M H, Tang T, Miyanohara A, Feramisco J R, Hammond H K. Beta(1)-adrenergic receptor vs. adenylyl cyclase 6 expression in cardiac myo-cytes: differences in transgene localization and intracellular signaling. Cell Signal 2010; 22: 584-9.
19. Tang T, Lai N C, Wright A T, et al. Adenylyl cyclase 6 deletion increases mortality during sus-tained beta-adrenergic receptor stimulation. J Mol Cell Cardiol 2013; 60:60-7.
20. Tang T, Gao M H, Lai N C, et al. Adenylyl cyclase type 6 deletion decreases left ventricular function via impaired calcium handling. Circulation 2008; 117:61-9.
21. Gao M H, Tang T, Guo T, et al. Adenylyl cyclase type VI increases Akt activity and phospholamban phospho-rylation in cardiac myocytes. J Biol Chem 2008; 283: 33527-35.
22. Tang T, Hammond H K, Firth A, et al. Adenylyl cyclase 6 improves calcium uptake and left ven-tricular function in aged hearts. J Am Cell Cardiol 2011; 57:1846-55.
23. Baker D L, Hashimoto K, Grupp I L, et al. Targeted overexpression of the sarcoplasmic reticulum $Ca^{2+}$ ATPase increases cardiac contractility in transgenic mouse hearts. Circ Res 1998; 83:1205-14.
24. Fine B, Hodakoski C, Koujak S, et al. Activation of the PI3K pathway in cancer through inhibition of PTEN by exchange factor P-REX2a. Science 2009; 325:1261-5.
25. Sun H, Kerfant B G, Zhao D, et al. Insulin-like growth factor-1 and PTEN deletion enhance cardiac L-type $Ca^{2+}$ currents via increased PI3Kal-pha/PKB signaling. Circ Res 2006; 98:1390-7.
26. Kass D A, Maughan W L, Guo Z M, Kono A, Sunagawa K, Sagawa K. Comparative influence of load versus inotropic states on indexes of ventricular contractility: experimental and theoretical analysis based on pressure-volume relationships. Circulation 1987; 76:1422-36.
27. Velotta J B, Kimura N, Chang S H, et al. Alpha-B-crystallin improves murine cardiac function and attenuates apoptosis in human endothelial cells exposed to ischemia-reperfusion. Ann Thorac Surg 2011; 91:1907-13.

REFERENCES—EXAMPLE 3

1. Barry W H, Bridge J H. Intracellular calcium homeostasis in cardiac myocytes. Circulation 87: 1806-1815, 1993.
2. Bers D M. Calcium cycling and signaling in cardiac myocytes. Annu Rev Physiol 70: 23-49, 2008.
3. Gao M R, Tang T, Guo T, Sun S Q, Feramisco J R, Hammond H K. Adenylyl cyclase type VI gene transfer reduces phospholamban expression in cardiac myocytes via activating transcription factor 3. J Biol Chem 279: 38797-38802, 2004.
4. Gao M R, Lai N C, Tang T, Guo T, Tang R, Chun B J, Wang H, Dalton N N, Suarez J, Dillmann W H, Hammond H K. Preserved cardiac function despite marked impairment of cAMP generation. PLoS One 8:e72151, 2013.
5. Gao M H, Lai N C, Giamouridis D, Kim Y C, Tan Z, Guo T, Dillman W H, Suarez J, Hammond H K. Cardiac-directed expression of adenylyl cyclase domain reverses cardiac dysfunction caused by sustained beta-adrenergic receptor stimulation. JACC Basic Transl Sci 1: 617-629, 2016.

6. Gao M R, Lai N C, Roth D M, Zhou J, Zhu J, Anzai T, Dalton N, Hammond H K. Adenylyl cyclase increases responsiveness to catecholamine stimulation in transgenic mice. Circulation 99: 1618-1622, 1999.
7. Gao M R, Lai N C, Miyanohara A, Schilling J M, Suarez J, Tang T, Guo T, Tang R, Parikh J, Giamouridis D, Dillmann W H, Patel H H, Roth D M, Dalton N D, Hammond H K. Intravenous adeno-associated virus serotype 8 encoding urocortin-2 provides sustained augmentation of left ventricular function in mice. Hum Gene Ther 24: 777-785, 2013
8. Hammond H K, Penny W F, Traverse J H, Henry T D, Watkins M W, Yancy C W, Sweis R N, Adler E D, Patel A N, Murray D R, Ross R S1, Bhargava V, Maisel A, Barnard D D, Lai N C, Dalton N D, Lee M L, Narayan S M, Blanchard D G, Gao M H. Intracoronary gene transfer of adenylyl cyclase 6 in patients with heart failure: a randomized clinical trial. JAMA Cardiol 1: 163-171, 2016.
9. Horikawa Y T, Panneerselvam M, Kawaraguchi Y, Tsutsumi Y M, Ali S S, Balijepalli R C, Murray F, Head B P, Niesman I R, Rieg T, Vallon V, Insel P A, Patel H H, Roth D M. Cardiac-specific overexpression of caveolin-3 attenuates cardiac hypertrophy and increases natriuretic peptide expression and signaling. J Am Coll Cardiol 57: 2273-2283, 2011.
10. Kass D A, Maughan W L, Guo Z M, Kono A, Sunagawa K, Sagawa K. Comparative influence of load versus inotropic states on indexes of ventricular contractility: experimental and theoretical analysis based on pressure-volume relationships. Circulation 76: 1422-1436, 1987.
11. O'Connell T D, Rodrigo M C, Simpson P C. Isolation and culture of adult mouse cardiac myocytes. Methods Mol Biol 357: 271-296, 2007.
12. Roger V L. Epidemiology of the heart failure. Circ Res 113: 646-659, 2004.
13. Sugano Y, Lai N C, Gao M H, Firth A L, Yuan J X, Lew W Y, Hammond H K. Activated expression of cardiac adenylyl cyclase 6 reduces dilation and dysfunction of the pressure-overloaded heart. Biochem Biophys Res Commun. 405: 349-355, 2011.
14. Sunahara R K, Dessauer C W, Whisnant R E, Kleuss C, Gilman A G. Interaction of Gsα with the cytosolic domains of mammalian adenylyl cyclase. J Biol Chem 272: 22265-22271, 1997.
15. Tang T, Gao M H, Lai N C, Firth A L, Takahashi T, Guo T, Yuan J X, Roth D M, Hammond H K. Adenylyl cyclase type 6 deletion decreases left ventricular function via impaired calcium handling. Circulation 117: 61-69, 2008
16. Tang W J, Gilman A G. Construction of a soluble adenylyl cyclase activated by Gs alpha and forskolin. Science 268:1769-1772, 1995.
17. Thangavel M, Liu X, Sun S Q, Kaminsky J, Ostrom R S. The C1 and C2 domains target human type 6 adenylyl cyclase to lipid rafts and caveolae. Cell Signal 21: 301-308, 2009

A number of embodiments as provided herein have been described. Nevertheless, it can be understood that various modifications may be made without departing from the spirit and scope of the invention. Accordingly, other embodiments are within the scope of the following claims.

---

What is claimed is:

1. An isolated or recombinant, or chimeric, polypeptide comprising:
   (a) a first peptide sequence; and
   (b) a second peptide sequence, wherein the first peptide sequence is linked to the amino terminus of the second peptide sequence via a peptide linker,
   wherein
   (i) the first peptide sequence comprises the sequence as set forth in SEQ ID NO:1 and the second peptide sequence comprises a sequence comprising amino acids 939 to 1157 of mouse adenylyl cyclase type 6(AC6), and the peptide linker comprises the amino acid sequence AAAGGIPPAAAM (SEQ ID NO:8), or
   (ii) the isolated or recombinant, or chimeric, polypeptide is encoded by a nucleic acid sequence comprising the sequence as set forth in SEQ ID NO:4, and/or has the amino acid sequence as set forth in SEQ ID NO:5,
   wherein the first peptide sequence and the second peptide sequence are operably linked.

2. The isolated or recombinant, or chimeric, polypeptide of claim 1, wherein the linker peptide consists of the amino acid sequence AAAGGIPPAAAM (SEQ ID NO:8).

3. An isolated or recombinant nucleic acid or nucleic acid sequence encoding the isolated or recombinant, or chimeric, polypeptide of claim 1.

4. The isolated or recombinant nucleic acid, or nucleic acid sequence, of claim 3, wherein the nucleic acid sequence consists of the sequence as set forth in SEQ ID NO:4, or the polypeptide consists of the sequence as set forth in SEQ ID NO:5.

5. A vector or expression construct having contained therein a nucleic acid having the sequence as set forth in claim 3, wherein the nucleic acid is operably linked to a transcriptional regulatory sequence, or a promoter.

6. The vector or expression construct of claim 5, wherein the vector is selected from the group consisting of an adeno-associated virus (AAV), a lentivirus, an adenovirus, and a plasmid.

7. The vector or expression construct of claim 6, wherein the AAV is selected from the group consisting of AAV1, AAV2, AAV3, AAV4, AAV5, AAV6, AAV7, AAV8, AAV9, AAV10 AAV11, AAV12, pseudotyped AAV, a rhesus-derived AAV, AAVrh8, AAVrh10 and AAV-DJan AAV capsid mutant, an AAV hybrid serotype, an organ-tropic AAV, a cardiotropic AAV, and a cardiotropic AAVM41 mutant.

8. An isolated, recombinant or engineered cell or host cell, comprising the vector or expression construct of claim 5.

9. A non-human transgenic animal having contained therein the host cell of claim 8.

10. The isolated or recombinant, or chimeric, polypeptide of claim 1, further comprising an epitope tag.

11. The isolated or recombinant, or chimeric, polypeptide of claim 10, wherein the epitope tag comprises an amino acid sequence DTYRYI (SEQ ID NO:9).

* * * * *